US010975147B2

(12) United States Patent
Keyt et al.

(10) Patent No.: US 10,975,147 B2
(45) Date of Patent: *Apr. 13, 2021

(54) MODIFIED J-CHAIN

(71) Applicant: IGM Biosciences, Inc., Mountain View, CA (US)

(72) Inventors: Bruce Keyt, Hillsborough, CA (US); Leonard George Presta, San Francisco, CA (US); Fen Zhang, San Francisco, CA (US); Ramesh Baliga, Redwood City, CA (US)

(73) Assignee: IGM Biosciences, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/803,745

(22) Filed: Feb. 27, 2020

(65) Prior Publication Data

US 2020/0190190 A1 Jun. 18, 2020

Related U.S. Application Data

(63) Continuation of application No. 16/136,049, filed on Sep. 19, 2018, which is a continuation of application No. 15/301,366, filed as application No. PCT/US2015/024149 on Apr. 2, 2015, now Pat. No. 10,400,038.

(60) Provisional application No. 61/974,738, filed on Apr. 3, 2014.

(51) Int. Cl.
*C07K 16/28* (2006.01)
*C07K 16/46* (2006.01)
*C07K 16/18* (2006.01)
*A61K 39/00* (2006.01)

(52) U.S. Cl.
CPC .......... *C07K 16/2809* (2013.01); *C07K 16/18* (2013.01); *C07K 16/28* (2013.01); *C07K 16/283* (2013.01); *C07K 16/2887* (2013.01); *C07K 16/468* (2013.01); *A61K 2039/505* (2013.01); *C07K 2317/22* (2013.01); *C07K 2317/31* (2013.01); *C07K 2317/52* (2013.01); *C07K 2317/569* (2013.01); *C07K 2317/622* (2013.01); *C07K 2317/73* (2013.01)

(58) Field of Classification Search
CPC ...... C07K 16/28; C07K 16/468; C07K 16/18; C07K 16/283; A61K 2039/505
See application file for complete search history.

(56) References Cited

U.S. PATENT DOCUMENTS

| 4,816,567 | A  | 3/1989  | Cabilly      |
|-----------|----|---------|--------------|
| 5,434,340 | A  | 7/1995  | Krimpenfort  |
| 5,798,229 | A  | 8/1998  | Strittmatter |
| 5,831,034 | A  | 11/1998 | Katinger     |
| 5,911,989 | A  | 6/1999  | Katinger     |
| 6,165,463 | A  | 12/2000 | Platz        |
| 6,284,536 | B1 | 9/2001  | Morrison     |
| 6,476,198 | B1 | 11/2002 | Kang         |
| 6,676,924 | B2 | 1/2004  | Hansen       |
| 7,074,403 | B1 | 7/2006  | Goldenberg   |
| 7,109,304 | B2 | 9/2006  | Hansen       |
| 7,138,496 | B2 | 11/2006 | Hua          |
| 7,151,164 | B2 | 12/2006 | Hansen       |
| 7,238,785 | B2 | 7/2007  | Govindan     |
| 7,282,567 | B2 | 10/2007 | Goldenberg   |
| 7,300,655 | B2 | 11/2007 | Hansen       |
| 7,311,912 | B1 | 12/2007 | Hein         |
| 7,312,318 | B2 | 12/2007 | Hansen       |
| 7,387,773 | B2 | 6/2008  | Murray       |
| 7,402,312 | B2 | 7/2008  | Rosen        |
| 7,541,440 | B2 | 6/2009  | Goldenberg   |
| 7,601,351 | B1 | 10/2009 | Rosen        |
| 7,612,180 | B2 | 11/2009 | Goldenberg   |
| 7,709,615 | B2 | 5/2010  | Irie         |
| 7,932,360 | B2 | 4/2011  | Van Berkel   |
| 7,951,378 | B2 | 5/2011  | Larrick      |
| 8,114,965 | B2 | 2/2012  | Maddon       |
| 8,153,125 | B2 | 4/2012  | Watkins      |
| 8,257,703 | B2 | 9/2012  | Irie         |
| 8,333,971 | B2 | 12/2012 | Goldenberg   |
| 8,337,844 | B2 | 12/2012 | Carr         |
| 8,377,435 | B2 | 2/2013  | Bhat         |
| 9,173,961 | B2 | 11/2015 | Deckert      |
| 9,409,976 | B2 | 8/2016  | Teng         |
| 9,458,241 | B2 | 10/2016 | Bhat         |
| 9,938,347 | B2 | 4/2018  | Wang         |
| 9,951,134 | B2 | 4/2018  | Keyt         |
| 10,351,631 | B2 | 7/2019  | Keyt        |
| 10,400,038 | B2 | 9/2019  | Keyt        |

(Continued)

FOREIGN PATENT DOCUMENTS

| AU | 697387 | 3/1996 |
|----|--------|--------|
| AU | 708301 | 5/1996 |

(Continued)

OTHER PUBLICATIONS

Arnold, J., et al., (2005), "Human serum IgM glycosylation: identification of glycoforms that can bind to mannan-binding lectin", The Journal of Biological Chemistry, vol. 280(32): 29080-29087.

Bacac, M., et al., (2018), "CD20-TCB with Obinutuzumab Pretreatment as Next-Generation Treatment of Hematologic Malignancies", Clinical Cancer Research, 24(19): 4785-4797, includes supplementary methods, Binding to CD20- and CD3-expressing cells, 24 additional pages.

(Continued)

*Primary Examiner* — Lei Yao

(57) ABSTRACT

The present invention concerns modified recombinant J-chain polypeptides, binding molecules, such as antibodies comprising the same, and their uses.

28 Claims, 21 Drawing Sheets

Specification includes a Sequence Listing.

(56) References Cited

U.S. PATENT DOCUMENTS

| | | |
|---|---|---|
| 10,604,559 B2 | 3/2020 | Carroll |
| 10,618,978 B2 | 4/2020 | Keyt |
| 10,689,449 B2 | 6/2020 | Wang |
| 10,787,520 B2 | 9/2020 | Keyt |
| 10,899,835 B2 | 1/2021 | Baliga |
| 2002/0006630 A1 | 1/2002 | Sirbasku |
| 2003/0224443 A1 | 12/2003 | Hiatt |
| 2004/0005318 A1 | 1/2004 | Davis |
| 2004/0137001 A1 | 7/2004 | Schreiber |
| 2004/0156826 A1 | 8/2004 | Dangond |
| 2005/0003431 A1 | 1/2005 | Wucherpfennig |
| 2005/0129616 A1 | 6/2005 | Salcedo |
| 2005/0202026 A1 | 9/2005 | Hiatt |
| 2005/0287153 A1 | 12/2005 | Dennis |
| 2006/0063234 A1 | 3/2006 | Jones |
| 2006/0153854 A1 | 7/2006 | Bhat |
| 2007/0014720 A1 | 1/2007 | Gazit-Bornstein |
| 2007/0154469 A1 | 7/2007 | Irie |
| 2007/0248601 A1 | 10/2007 | Cogne |
| 2007/0249812 A1 | 10/2007 | Hayasaka |
| 2008/0044413 A1 | 2/2008 | Hammond |
| 2008/0145420 A1 | 6/2008 | Simon |
| 2009/0022738 A1 | 1/2009 | Hofmeister |
| 2009/0130089 A9 | 5/2009 | Smith |
| 2009/0291899 A1 | 11/2009 | Ferrante |
| 2010/0093979 A1 | 4/2010 | Lazar |
| 2010/0172899 A1 | 7/2010 | Irie |
| 2010/0184959 A1 | 7/2010 | Guler-Gane |
| 2010/0279932 A1 | 11/2010 | Ledbetter |
| 2010/0279939 A1 | 11/2010 | Fries |
| 2011/0110852 A1 | 5/2011 | Miller |
| 2011/0129412 A1 | 6/2011 | Gazit-Bornstein |
| 2011/0318339 A1 | 12/2011 | Smider |
| 2012/0039870 A9 | 2/2012 | Dolk |
| 2012/0045432 A9 | 2/2012 | Yu |
| 2012/0258126 A1 | 10/2012 | Scholler et al. |
| 2012/0269830 A1 | 10/2012 | Horowitz |
| 2013/0095097 A1 | 4/2013 | Blankenship |
| 2013/0164283 A1 | 6/2013 | Bhat |
| 2013/0189258 A1 | 7/2013 | Rother |
| 2013/0280167 A1 | 10/2013 | Rodriguez |
| 2014/0010809 A1 | 1/2014 | Ledbetter |
| 2014/0044739 A1 | 2/2014 | Teng |
| 2014/0088295 A1 | 3/2014 | Smith et al. |
| 2014/0154252 A1 | 6/2014 | Thompson |
| 2014/0249044 A1 | 9/2014 | Braz Gonçalves |
| 2015/0004167 A1 | 1/2015 | Wu |
| 2015/0038682 A1 | 2/2015 | Tsurushita |
| 2015/0259420 A1 | 9/2015 | Triebel |
| 2016/0222132 A1 | 8/2016 | Keyt |
| 2016/0326233 A1 | 11/2016 | Mondelli |
| 2016/0368971 A1 | 12/2016 | Keyt |
| 2017/0183409 A1 | 6/2017 | Keyt |
| 2017/0283510 A1 | 10/2017 | Keyt |
| 2017/0320955 A1 | 11/2017 | Wang |
| 2018/0009897 A1 | 1/2018 | Wang |
| 2018/0118814 A1 | 5/2018 | Carroll |
| 2018/0118816 A1 | 5/2018 | Keyt |
| 2018/0265596 A1 | 9/2018 | Keyt |
| 2019/0002566 A1 | 1/2019 | Keyt |
| 2019/0100597 A1 | 4/2019 | Keyt |
| 2019/0185570 A1 | 6/2019 | Keyt |
| 2019/0330360 A1 | 10/2019 | Wang |
| 2019/0330374 A1 | 10/2019 | Wang |
| 2019/0338031 A1 | 11/2019 | Keyt |
| 2019/0338040 A1 | 11/2019 | Keyt |
| 2019/0338041 A1 | 11/2019 | Baliga |
| 2020/0239572 A1 | 7/2020 | Baliga |
| 2020/0255546 A1 | 8/2020 | Keyt |
| 2020/0377577 A1 | 12/2020 | Keyt |
| 2021/0032357 A1 | 2/2021 | Keyt |

FOREIGN PATENT DOCUMENTS

| | | | |
|---|---|---|---|
| AU | 2004297218 | | 6/2005 |
| CA | 2358520 | | 7/2000 |
| CA | 2662701 | | 10/2008 |
| EP | 642585 | | 3/1995 |
| EP | 1169352 | | 1/2002 |
| EP | 1301541 | | 4/2003 |
| EP | 1617870 | | 1/2006 |
| EP | 1833848 | | 9/2007 |
| EP | 2219458 | | 8/2010 |
| EP | 2254592 | | 12/2010 |
| EP | 2264163 | | 12/2010 |
| EP | 2300498 | | 3/2011 |
| EP | 2465871 | | 6/2012 |
| EP | 2649184 | | 10/2013 |
| EP | 2655415 | | 10/2013 |
| EP | 2771361 | | 9/2014 |
| EP | 2962103 | | 1/2016 |
| WO | 1989001975 | | 3/1989 |
| WO | 1998030591 | | 7/1998 |
| WO | 1998030592 | | 7/1998 |
| WO | 2001012820 | | 2/2001 |
| WO | 2001014424 | | 3/2001 |
| WO | 2004110143 | | 12/2004 |
| WO | 2005103081 | | 11/2005 |
| WO | 2006052641 | | 5/2006 |
| WO | 2006130458 | | 12/2006 |
| WO | 2008140477 | | 11/2008 |
| WO | 2009013620 | | 1/2009 |
| WO | 2009130575 | | 10/2009 |
| WO | 2010105256 | | 9/2010 |
| WO | WO2013158748 | * | 4/2013 |
| WO | 2013061098 | | 5/2013 |
| WO | 2013087913 | | 6/2013 |
| WO | 2013120012 | | 8/2013 |
| WO | 2013158748 | | 10/2013 |
| WO | 2013188870 | | 12/2013 |
| WO | 2014022592 | | 2/2014 |
| WO | 2014124457 | | 8/2014 |
| WO | 2014207064 | | 12/2014 |
| WO | 2015037000 | | 3/2015 |
| WO | 2015053887 | | 4/2015 |
| WO | 2015103072 | | 7/2015 |
| WO | 2015120474 | | 8/2015 |
| WO | 2015151081 | | 10/2015 |
| WO | 2015153912 | | 10/2015 |
| WO | 2016118641 | | 7/2016 |
| WO | 2016141303 | | 9/2016 |
| WO | 2016154593 | | 9/2016 |
| WO | 2016168758 | | 10/2016 |
| WO | 2017059380 | | 4/2017 |
| WO | 2017059387 | | 4/2017 |
| WO | 2017196867 | | 11/2017 |
| WO | 2018017761 | | 1/2018 |
| WO | 2018017763 | | 1/2018 |
| WO | 2018017888 | | 1/2018 |
| WO | 2018017889 | | 1/2018 |
| WO | 2018187702 | | 10/2018 |
| WO | 2019165340 | | 8/2019 |
| WO | 2019169314 | | 9/2019 |
| WO | 2020086745 | | 4/2020 |
| WO | 2020163646 | | 8/2020 |

OTHER PUBLICATIONS

Baliga, R., et al, (2019), "IGM-2323: High Avidity IgM-based CD20 x CD3 Bispecific Antibody for Enhanced T-Cell Dependent Kiling with Minimal Cytokine Release", Abstract 1574 at American Society of Hematology Annual Meeting, Dec. 7-10, 2019, Orlando, FL.

Beers, S., et al., (2010), "Antigenic modulation limits the efficacy of anti-CD20 antibodies: implications for antibody selection", Blood, 115(25): 5191-5201.

Bornstein, G., et al., (2010), "Development of a new fully human anti-CD20 monoclonal antibody for the treatment of B-cell malignancies", Invest New Drugs, 28:561-574.

(56) References Cited

OTHER PUBLICATIONS

Bortoletto, N., et al., (2002), "Optimizing anti-CD3 affinity for effective T cell targeting against tumor cells", Eur. J. Immunol, 32: 3102-3107.
Bowles, J., et al., (2006), "Anti-CD20 monoclonal antibody with enhanced affinity for CD16 activates NK cells at lower concentrations and more effectively than rituximab", Blood, 108(8): 2648-2654.
Brüggemann M., et al., (1987), "Comparison of the effector functions of human immunoglobulins using a matched set of chimeric antibodies", J. Exp. Med, 166: 1351-1361.
Castro, C., et al., (2014), "Putting J chain back on the map: how might its expression define plasma cell development?", The Journal of Immunology, 193: 3248-3255.
Chu, S., et al., (2014), "Immunotherapy with Long-Lived Anti-CD20 x Anti-CD3 Bispecific Antibodies Stimulates Potent T Cell-mediated Killing of Human B Cell lines and Circulating and Lymphoid B Cells in Monkeys: A Potential Therapy for B Cell Lymphomas and Leukemias", Xencor, Inc., Monrovia, California 91016 USA, Poster.
Cregger, M., et al., (2006), "Immunohistochemistry and Quantitative Analysis of Protein Expression", Arch Pathol Lab Med., 130: 1026-1030.
Czuczman, M., et al., (2008), "Acquirement of rituximab resistance in lymphoma cell lines is associated with both global CD20 gene and protein down-regulation regulated at the pretranscriptional and posttranscriptional levels", Clin Cancer Res, 14(5): 1561-1570.
Davis, T., et al., (1999), "Single-agent monoclonal antibody efficacy in bulky non-Hodgkin's lymphoma: results of a phase II trial of rituximab", J. Clin Oncol. 17: 1851-1857.
Davis, T., et al., (2000), "Rituximab anti-CD20 monoclonal antibody therapy in non-Hodgkin's lymphoma: safety and efficacy of re-treatment", Journal of Clinical Oncology, 18(17): 3135-3143.
Ghielmini, M., (2004), "Prolonged treatment with rituximab in patients with follicular lymphoma significantly increases event-free survival and response duration compared with the standard weekly x 4 schedule", Blood, 103(12): 4416-4423.
Hagenbeek, A., et al., (2009), "Evaluation of Ofatumumab, a Novel Human CD20 Monoclonal Antibody, as Single Agent Therapy in Rituximab-Refractory Follicular Lymphoma", Blood, 114: 935, 6 pages.
Haidar, JH., et al., (2003), "Loss of CD20 expression in relapsed lymphomas after rituximab therapy", Eur J. Haematol, 70: 330-332.
Hensel, F., et al., (2013), "Early development of PAT-SM6 for the treatment of melanoma", 23(4): 264-275.
Hsu, D., et al., (1999), "A humanized anti-CD3 antibody, HuM291, with low mitogenic activity, mediates complete and reversible T-cell depletion in chimpanzees", Transplantation, 68(4): 545-554.
Klimovich, V. B., (2011), "IgM and Its Receptors: Structural and Functional Aspects", Biochemistry, 76(5): 534-549.
Liu, X., et al., (2005), "Recombinant of J chain-HNP-1 cDNA and the construction of expression vector", Di-San Junyi Daxue Xuebao, 27(8), 697-699. English Abstract Only Available.
Maloney, D., et al., (1997), "IDEC-C2B8 (Rituximab) anti-CD20 monoclonal antibody therapy in patients with relapsed low-grade non-Hodgkin's lymphoma", Blood, 90(6): 2188-2195.
Mandikian, D., et al., (2018), "Relative Target Affinities of T Cell-Dependent Bispecific Antibodies Determine Biodistribution in a Solid Tumor Mouse Model", Mol Cancer Ther., 17(4): 776-785, doi: 10.1158/1535-7163. MCT-17-0657.
Marcus, R., et al., (2017), "Obinutuzumab for the First-Line Treatment of Follicular Lymphoma", N Engl. J. Med. 377(14): 1331-44.
Mølhøj, M., et al., (2007), "CD19-/CD3-bispecific antibody of the BiTE class is far superior to tandem diabody with respect to redirected tumor cell lysis", Molecular Immunology 44: 1935-1943.
Niles, M., et al., (1995), "Polymer IgM assembly and secretion in lymphoid and nonlymphoid cell lines: evidence that J chain is required for pentamer IgM synthesis", Proc. Natl. Acad. Sci. USA, 92: 2884-2888.

Rasche, L., et al., (2015), "GRP78-directed immunotherapy in relapsed or refractory multiple myeloma—results from a phase 1 trial with the monoclonal immunoglobulin M antibody PAT-SM6", Haematologica, J. Mol. Biol, 100(3): 377-384.
Rezvani, A., et al., (2011), "Rituximab Resistance", Best Pract Res Clin Haematol, 24(2): 203-216.
Saber, H., et al., (2017), "An FDA oncology analysis of CD3 bispecific constructs and first-in-human dose selection", Regulatory Toxicology and Pharmacology, 90: 144-152.
Smith, E., et al., (2015), "A novel, native-format bispecific antibody triggering T-cell killing of B-cells is robustly active in mouse tumor models and cynomolgus monkeys", Scientific Reports, 5: 17943, 12 pages.
Sun, L., et al., (2015), "Anti-CD20/CD3 T cell-dependent bispecific antibody for the treatment of B cell malignancies", Immunotherapy, vol. 7(287), 287ra70, 11 pages.
Teachey, D., et al., (2013), "Cytokine release syndrome after blinatumomab treatment related to abnormal macrophage activation and ameliorated with cytokine directed therapy", Blood Journal, DOI 10.1182/blood-2013-02-485623.
Van Imhoff, G., et al., (2017), "Ofatumumab Versus Rituximab Salvage Chemoimmunotherapy in Relapsed or Refractory Diffuse Large B-Cell Lymphoma: The ORCHARRD Study", Journal of Clinical Oncology, 35(5): 544-551.
Vitolo, U., et al., (2017), "Obinutuzumab or Rituximab Plus Cyclophosphamide, Doxorubicin, Vincristine, and Prednisone in Previously Untreated Diffuse Large B-Cell Lymphoma", Journal of Clinical Oncology, 35(31): 3529-3537.
Wing, M., (2008), "Monoclonal Antibody First Dose Cytokine Release Syndromes—Mechanisms and Prediction", Journal of Immunotoxicology, 5: 11-18.
Wu, J., et al., (2015), "Blinatumomab: a bispecific T cell engager (BiTE) antibody against CD19/CD3 for refractory acute lymphoid leukemia", Journal of Hematology & Oncology, 8:104, DOI 10.1186/s13045-015-0195-4, 7 pages.
Klein, J., et al., (2014,) "Design and characterization of structured protein linkers with differing flexibilities" Protein Eng Des Sel 27, 325-330.
Kohler et al., "Continuous cultures of fused cells secreting antibody of predefined specificity," Nature 1975, vol. 256, No. 495-7.
Kragten, E., et al., (1995), "Site-specific analysis of the N-Glycans on Murine Polymeric Immunoglobulin A. Using Liquid Chromatography/Electrospray Mass Spectrometry", vol. 30, 1679-1686.
Krugmann, S., et al. (1997), "Structural Requirements for Assembly of Dimeric IgA Probed by Site-Directed Mutagenesis of J Chain and a Cysteine Residue of the α-chain CH2 Domain", The Journal of Immunology, 159: 244-249.
Ksiezak-Reding, H., et al., 1988, "Alz 50, a monoclonal antibody to Alzheimer's disease antigen, cross-reacts with tau proteins from bovine and normal human brain", J. Biol. Chem. 263, 7943-7947.
Lamminmäki, U. et al., (2001), "Crystal Structure of a Recombinant Anti-estradiol Fab Fragment in Complex with 17ß Estradiol", The Journal of Biological Chemistry, vol. 276(39): 36687-36694.
Lewis, A.K. et al., 2014, "Open and Closed Conformations of the Isolated Transmembrane Domain of Death Receptor 5 Support a New Model of Activation" Biophys J 106, L21-L24.
Liedtke, M., et al., (2012), "Phase I trial of a novel human monoclonal antibody mAb216 in patients with relapsed or refractory B-cell acute lymphoblastic leukemia" Haematologica 97, 30-37.
Lines, J., et al, (2014), "VISTA Is an Immune Checkpoint Molecule for Human T Cells", Cancer Research 74(7): 1924-1932.
Liu, X. et al., (2005), "Preliminary study on recombination of J-HNP-1 and its antibacterial effect in vitro" Shijie Huaren Xiaohua Zazhi, 13(22), 2640-2644, English Abstract Only Available.
Liu, Xianhua, et al. 2006, "Expression Detection of the gene of α-defensin-1 with J chain in the transfected COS-7 cells", Chin Crit Care Med, vol. 18, No. 2, pp. 71 to 73 with Full English translation.
MacCallum R., et al. (1996), "Antibody-antigen Interactions: Contact Analysis and binding Site Topography", J. Mol. Biol. 262: 732-745.

(56) References Cited

OTHER PUBLICATIONS

Maekawa, N., et al., (2014), "Expression of PD-L1 on Canine Tumor Cells and Enhancement of IFN-γ Production from Tumor-Infiltrating Cells by PD-L1 Blockade", PLOS One, vol. 9(6), e98415.
Mariuzza, R. A., (1987), "The Structural Basis of Antigen-Antibody Recognition", vol. 16: 139-159.
Marks et al., "By-passing immunization. Human antibodies from V-gene libraries displayed on phage," J. Mol. Biol. 1991, vol. 222, pp. 582-597.
Mestecky, J., et al., (1973), "J-chain of polymeric IgA myeloma proteins", Protides of the Biological Fluids, vol. 20: 279-283, Abstract Only Available.
Meyer et al., "Improved In Vivo Anti-Tumor Effects of IgA-Her2 Antibodies Through Half-Life Extension and Serum Exposure Enhancement by FcRn Targeting", mAbs, Jan. 2016, pp. 87-98, vol. 8, Issue 1.
Mordenti, J., et al. (1999), "Intraocular Pharmacokinetics and Safety of a Humanized Monoclonal Antibody in Rabbits after Intravitreal Administration of a Solution or a PLGA Microsphere Formulation", Toxicological Sciences, 52: 101-106.
Mordenti, J., et al., (1999), "Comparisons of the Intraocular Tissue Distribution, Pharmacokinetics, and Safety of 125I-Labeled Full-Length and Fab Antibodies in Rhesus Monkeys Following Intravitreal Administration", Investigative Pathology, vol. 27, No. 5, pp. 536-544.
Morrison et al, "Chimeric human antibody molecules: mouse antigen-binding domains with human constant region domains," PNAS 1984, vol. 81, pp. 6851-6855.
Mosmann, T.R., et al. (1978), "Modification and Fate of J. Chain in myeloma cells in the presence and absence of polymeric immunoglobulin secretion", Eur. J. Immunol. 8: 84-101.
Müller, M. et al., (2012), "Improving the pharmacokinetic properties of biologics by fusion to an anti-HSA shark VNAR domain" MAbs 4, 673-685.
NCBI Reference Sequence: NP_653247.1,17.04.2013, Immunoglobulin J chain precursor [*Homo sapiens*].
Niwa, H., Yamamura, K., Miyazaki, J., 1991. Efficient selection for high-expression transfectants with a novel eukaryotic vector. Gene 108, 193-199.
Nocentini, G., et al., (1997), "A new member of the tumor necrosis factor/nerve growth factor receptor family inhibits T cell receptor-induced apoptosis", Proc. Natl. Acad. Sci. U.S.A. 94, 6216-6221.
Noren et al., "A general method for site-specific incorporation of unnatural amino acids into proteins," Science 1989, vol. 244, p. 182-188.
Ofei et al., "Effects of an engineered human anti-TNF-a antibody (CDP571) on insulin sensitivity and glycemic control inpatients with NIDDM," Diabetes 1996, vol. 45, pp. 881-885.
Office Action dated Sep. 27, 2019 in U.S. Appl. No. 15/764,870.
Padlan, E., et al.., (1989), "Structure of an antibody-antigen complex: crystal structure of the HyHel-10 Fab-lysozyme complex;", Proc. Natl. Acad. Sci. USA, vol. 86: 5938-5942.
Palanichamy Arumugam et al, "Rituximab efficiently depletes increased CD20-expressing T cells in multiple sclerosis patients.", Journal of Immunology (Baltimore, MD.: 1950) Jul. 15, 2014, (Jul. 15, 2014), vol. 193, No. 2, pp. 580-586.
Pardoll, D.M., (2012), "The blockade of immune checkpoints in cancer immunotherapy" Nat. Rev. Cancer 12(4): 252-264.
Pascal, V., et al. (2012) "Anti-CD20 IgA can protect mice against lymphoma development: evaluation of the direct impact of IgA and cytotoxic effector recruitment on CD20 Target cells", Haematologica, the Hematology Journal, vol. 97(11), pp. 1686-1694.
Paterson, J., et al., (2006), "The differential expression of LCK and BAFF-receptor and their role in apoptosis in human lymphomas", Haematologica 91: 772-780.
Paulik et al., "Drug-antibody conjugates with anti-HIV activity," Biochem. Pharmacol. 1999, vol. 58, pp. 1781-1790.
Ponders and Richards, "Tertiary templates for proteins. Use of packing criteria in the enumeration of allowed sequences for different structural classes," J. Mol. Biol. 1987, vol. 193, pp. 775-791.
Postow, M., et al., (2015), "Immune Checkpoint Blockade in Cancer Therapy", J. Clin. Oncol. 33(17): 1974-1982.
Presta, "Antibody engineering," Curr. Op. Struct. Biol. 1992, vol. 2, pp. 593-596.
Babbitts et al. "Human immunoglobulin heavy chain genes: evolutionary comparisons of C mu, C delta and C gamma genes and associated switch sequences," GenBank Accession No. CAB37838, Nucleic Acids Research 1981 vol. 9, No. 18, pp. 4509-4524.
Raju et al., "Potential therapeutic roles for antibody mixtures," Exp. Op. Biol. Ther. 2013, vol. 13, No. 10, pp. 1347-1352.
Randall, T., et al., (1992), "Direct Evidence That J Chain Regulates the Polymeric Structure of IgM in Antibody-secreting B Cells", The Journal of Biological Chemistry, vol. 267(25), 18002-18007.
Redwan, E., et al. (2006), "Recombinant human J-chain: fix the protein aggregations and yield maximize" Human Antibodies 15, 95-102.
Riechmann et al., "Reshaping human antibodies for therapy," Nature 1988, vol. 332, pp. 323-329.
Roopenian, D., et al., (2007), "FcRn: the neonatal Fc receptor comes of age", Nature Reviews, vol. 7, 715-725.
Rossi, E., et al. (2008) "Novel Designs of Multivalent Anti-CD20 Humanized Antibodies as Improved Lymphoma Therapeutics", Cancer Res, vol. 68(20), pp. 8384-8392.
Rudikoff, S., et al., (1982), "Single amino acid substitution altering antigen-binding specificity", Proc. Natl. Acad. Sci. USA, 79: 1979-1983.
Seifert, O., et al., (2012), "The IgM CH2 domain as covalently linked homodimerization module for the generation of fusion proteins with dual specificty", Protein engineering, Design & Selection, vol. 25(10): 603-612.
Singer, M., et al., "Genes and Genomes", Moscow, "Mir", 1998, vol. 1: 63-64, no translation available, reference is believed to be a standard textbook reference on antibody structure.
Smith, R. et al., (1995), "Addition of a mu-tailpiece to IgG results in polymeric antibodies with enhanced effector functions including complement-mediated cytolysis by IgG4" The Journal of Immunology 154, 2226-2236.
Sørensen, V., et al., (2000), "Structural requirements for incorporation of J chain into human IgM and IgA.", Int. Immunol. 12, 19-27.
Symersky, J., et al., (2000), "Expression of the recombinant human immunoglobulin J Chain in *Escherichia coli*", Molecular Immunology, 37: 133-140.
Tabrizi, M., et al. (2010), "Biodistribution Mechanisms of Therapeutic Monoclonal Antibodies in Health and Disease", The AAPS Journal, vol. 12, No. 1, pp. 33-43.
Tavolaro, S., et al al. (2013), "IgD cross-linking induces gene expression profiling changes and enhances apoptosis in chronic lymphocytic leukemia cells", Leukemia Research, 37: 455-462.
Tchoudakova, A., et al., 2009, "High level expression of functional human IgMs in human PER.C6 cells", MAbs 1, 163-171.
Tussiwand, R., et al., (2012), "BAFF-R expression correlates with positive selection of immature B cells", European Journal of Immunology, 42: 206-216.
Vajdos, F., et al., (2002), "Comprehensive Functional Maps of the Antigen-binding Site of an Anti-ErbB2 Antibody Obtained with Shotgun Scanning Mutagenesis", J. Mol. Biol. 320: 415-428.
Valley, C., et al, "Tumor Necrosis Factor-related Apoptosis-inducing Ligand (TRAIL) Induces Death Receptor 5 Networks That Are Highly Organized", The Journal of Biological chemistry, vol. 287, No. 25, pp. 21265-21278.
Vasquez, K., et al., (2011), "Quantitative Whole Body biodistribution of fluorescent-labeled Agents by Non-Invasive Tomographic Imaging", PLOS one, vol. 6, Issue 6, e20594.
Vcelar et al., "Reassessment of autoreactivity of the broadly neutralizing HIV antibodies 4E10 and 2F5 and retrospective analysis of clinical safety data," AIDS 2007, vol. 21, No. 16, pp. 2161-2170.
Wajant, H. (2015), "Principles of antibody-mediated TNF receptor activation", Cell Death and Differentiation, 22: 1727-1741.

(56) References Cited

OTHER PUBLICATIONS

Wang, W., et al. (2008), "Monoclonal Antibody Pharmacokinetis and Pharmacodynamics", State of the Art, vol. 84, No. 5, pp. 548-558.

Wang, Y. et al., (2007), "The design, construction and function of a new chimeric anti-CD20 antibody", Journal of Biotechnology, 129: 726-731.

Weiskopf, K., et al. (2013) "Engineered SIRPa Variants as Immunotherapeutic Adjuvants to Anticancer Antibodies", Science Express, vol. 341, pp. 89-91 with supplemental materials, 36 pages.

Wood, C.R., et al., (1990), "High level synthesis of immunoglobulins in Chinese hamster ovary cells". J. Immunol. 145, 3011-3016.

Woof et al.,"Structure and Function Relationships in IgA", Mucosal Immunology, Nov. 2011, pp. 590-597, vol. 4 No. 6.

Wu, H., et al., (1999), "Humanization of a Murine Monoclonal Antibody by simultaneous Optimization of Framework and CDR Residues", J. Mol. Biol. 294: 151-162.

Yoo et al., "Structural requirements for polymeric immunoglobulin assembly and association with J chain," J. Biol. Chem. 1999, vol. 274, No. 47, pp. 33771-33777.

Yu, X., et al., 2009, "The surface protein TIGIT suppresses T cell activation by promoting the generation of mature immunoregulatory dendritic cells," Nat. Immunol. 10, 48-57.

Yu, Y., et al. (2014), "Therapeutic bispecific antibodies cross the blood-brain barier in nonhuman primates", Antibody Therapeutics, vol. 6, Issue 261, 261ra154, 11 pages.

Zuchero Y. et al., (2015), "Discovery of Novel Blood-Brain Barrier Targets to Enhance Brain Uptake of Therapeutic Antibodies", Neuron 89: 70-82.

Aggarwal, B., et al., "Historical perspectives on tumor necrosis factor and its superfamily: 25 years later, a golden journey", 2012, Blood, vol. 119 (No. 3), pp. 651-665.

Albrecht, H., et al. (2006), "Recombinant Antibodies: From the Laboratory to the Clinic", Cancer Biotherapy & Radiopharmaceuticals, vol. 21: 285-304.

Ammann, J., et al. (2014), "Development and use of IgM/J-Chain Fusion Proteins for Chacterization of Immunoglobulin Superfamily Ligand-Receptor Interactions", Current Protocols in Protein Science, 19.24.1-19.24.11, Supplement 75.

Ammann, J., et al., (2012), "Detection of weak receptor-ligand interactions using IgM and J-chain-based fusion proteins", European Journal of Immunology, 42:1354-1356.

Andersen, J., et al., "Extending Serum Half-life of Albumin by Engineering Neonatal Fc Receptor (FcRn) Binding", 2014, Journal of Biological Chemistry, vol. 289, No. 19, pp. 13492-13502.

Azuma, Y., et al., "Recombinant Human Hexamer-Dominant IgM Monoclonal Antibody to Ganglioside GM3 for Treatment of Melanoma", 2007, Clin Cancer Res, vol. 13 (No. 9), pp. 2745-2750 with correction on article.

Bakema et al, "Immunoglobulin A, a next generation of therapeutic antibodies?", mAbs, Aug. 2011, vol. 3, No. 4, 352-361.

Baliga, R., et al., (2016) "High Avidity Anti-CD20 IgM Antibody for enhanced Complement-Dependent Cell Killing of Low CD20 Expressing Tumor Cells", Poster Presented at the PEGS Boston Meeting Apr. 25-29, 2016.

Binz, et al., "Engineering novel binding proteins from nonimmunoglobulin domains," Nature Biotechnology 2005, vol. 23, No. 10, pp. 1257-1268.

Braathen, R., et al. (2002), "The Carboxyl-terminal Domains of IgA and IgM Direct Isotype-specific Polymerization and Interaction with the Polymeric Immunoglobulin Receptor", The Journal of Biological Chemistry, vol. 277, No. 45, pp. 42755-42762.

Brodska et al, "Correlation of PD-L1 Surface Expression on Leukemia Cells with the Ratio of PD-L1 mRNA Variants and with Electrophoretic Mobility", Cancer Immunology Research, Aug. 2016, pp. 815-819, vol. 4, No. 10.

Cao, Y., et al., (2011), "Targeting cell surface ß2-microglobulin by pentameric IgM antibodies", Br J Haematol, 154(1): 111-121.

Casset, F., et al., (2003), "A peptide mimetic of an anti-CD4 monoclonal antibody by rational design", Biochemical and biophysical Research Communications, 307: 198-205.

Cazet et al., "Tumour-associated carbohydrate antigens in breast cancer," Breast Cancer Research 2010, vol. 12, No. 3, p. 204.

Chen, Y., et al., (1999), Selection and Analysis of an Optimized Anti-VEGF Antibody: Crystal Structure of an Affinity-matured Fab in Complex with Antigen, 293: 865-881.

Chintalacharuvu et al., "Hybrid IgA2/igG1 Antibodies with Tailor-Made Effector Functions", Clinical Immunology, Oct. 2001, pp. 21-31, vol. 101, No. 1, pp. 21-31.

Ćirić B., et al. (2009), "Effect of Valency on Binding Properties of the Antihuman IgM Monoclonal Antibody 202", Hybridoma, vol. 14. No. 6, pp. 537-544.

Clackson et al., "Making antibody fragments using phage display libraries" Nature 1991, vol. 352, pp. 624-628.

Colman, P.M. (1994) "Effects of amino acid sequence changes on antibody-antigen interactions", Biomolecular Research Institute, 55th Forum in Immunology, pp. 33-35.

Czajkowsky and Shao, "The human IgM pentamer is a mushroom-shaped molecule with a flexural bias," PNAS 2009, vol. 106, No. 35, pp. 14960-14965.

Davis et al., "On the structure of polymeric IgM," Eur. J. Immunol. 1988, vol. 18, No. 7, pp. 1001-1008.

Davis, A., et al., (1989), "IgM—Molecular requirements for its assembly and function", Immunology Today, 10(4): 7 pages.

De Pascalis, R., et al., (2002), "Grafting of "Abbreviated" Complementarity-Determining Regions Containing specificity-Determining Residues Essential for Ligand Contact to Engineer a Less Immunogenic Humanized Monoclonal Antibody", The Journal of Immunology, 169: 3076-3084.

Dennis, M., et al. (2002), "Albumin Binding as a General Strategy for Improving the Pharmacokinetics of Proteins", J. Biol. Chem. 277(38): 35035-35043.

Dennis, M., et al., (2012), "Transferrin Antibodies into the Brain", Neuropsychopharmacology Reviews, 37: 302-303.

Dorai et al, "The complete nucleotide sequence of a human immunoglobulin genomic Cu gene," GenBank Accession No. X14940.1, Nucleic Acids Research 1989, vol. 17, No. 15, p. 6412.

Ducry, L., et al., "Antibody-drug conjugates: linking cytotoxic payloads to monoclonal antibodies", 2010, Bioconjug. Chem. 21, 5-13.

Duramad, O., et al., (2014), "IGM-55.5 a novel monoclonal human recombinant IgM antibody with potent activity against B cell leukemia and lymphoma" IGM Biosciences, Inc.—Research and Development SRI International—Cancer Pharmacology, Stanford—Department of Obstetrics and Gynecology, Abstract No. 645 AACR Annual Meeting, Apr. 5-9, 2014, San Diego CA.

Ellman, "Biosynthetic method for introducing unnatural amino acids site-specifically into proteins," Meth. Enzym. 1991, vol. 202, pp. 301-336.

Fournier et al., "Bispecific antibodies and trispecific immunocytokines for targeting the immune system against cancer: preparing for the future," BioDrugs. 2013, vol. 27, No. 1, pp. 35-53.

Frutiger, S., et al., 1992, "Disulfide Bond Assignment in Human J Chain and its Covalent Pairing with Immunoglobulin M", Biochemistry, vol. 31, pp. 12643-12647.

Fukushima, N., et al., (2002), "Chacterization of Recombinant Monoclonal IgA Anti-PDC-E2 Autoantibodies Derived From patients with PBC", Hepatology: 35: 1383-1392.

Gaetano, N., et al., (2003), "Complement Activation Determines the Therapeutic Activity of Rituximab in Vivo", The Journal of Immunology, 171: 1581-1587.

Garcia-Pardo et al., "J chain is covalently bound to both monomer subunits in human secretory IgA," J. Biol. Chem. 1981, vol. 256, pp. 11734-11738.

Gibson Josefine, "Anti-PD-L1 for metastatic triple-negative breast cancer.", The Lancet. Oncology Jun. 2015, (Jun. 2015), vol. 16, No. 6, ISSN 1474-5488, p. e264, XP002765988.

Gilmour, J.E.M., et al. (2008), "Effect of the presence or absence of J Chain on expresion of recombinant anti-kell immunoglobulin", Transfusion Medicine, 18: 167-174.

(56) References Cited

OTHER PUBLICATIONS

Goswami et al., "Developments and challenges for mAb-Based therapeutics," Antibodies 2013, vol. 2, No. 3, pp. 452-500.

Harao et al., "Abstract LBb-263: Enhancing of CD8+ tumor-infiltrating lymphocyte expansion from triple-negative breast cancer patients using of 41BB costimulation", (Oct. 1, 2014), American Associaton for Cancer Research, URL: http://cancerres.aacrjournals.org/content/74/19_Supplement/LB-263, (Jan. 16, 2017), XP002765987.

Hay, M., et al., (2014), "Clinical development success rates for investigational drugs", Nature Biology, 32(1): 40-51.

Hirayasu, K. and Arase, H., "Immunoglobulin mu heavy chain, partial [*Homo sapiens*]," GenBank Accession No. AFM37312, Jun. 18, 2012 (2 pages).

Hopp, J., et al., (2010), "The effects of affinity and valency of an albumin-binding domain (ABD) on the half-life of a single-chain diabody-ABD fusion protein", vol. 23(11): 827-834.

Houghton, J., et al., (2015), "Site-specifically labeled CA19.9-targeted immunoconjugates for the PET, NIRF, and multimodal PET/NIRF imaging of pancreatic cancer", PNAS, vol. 112, No. 52: 15850-15855.

Jeon, H., et al., (2014), "Structure and Cancer Immunotherapy of the B7 Family Member B7x", Cell Rep., vol. 9(3): 1089-1098.

Johansen, F., et al., (2000), "Role of J Chain in Secretory Immunoglobulin Formation", Scand. J. Immunol., 52: 240-248.

Johansen, F., et al., (2001), "The J Chain Is Essential for Polymeric Ig Receptor-Mediated Epithelial Transport of IgA", The Journal of Immunology, 167: 5185-5192.

Johnson, R., et al. (2012) "Biological Activity of Anti-CD20 Multivalent HPMA Copolymer-Fab' Conjugates", Biomacromolecules, vol. 13, pp. 727-735.

Jones et al, "Replacing the complementarity-determining regions in a human antibody with those from a mouse," Nature 1986, vol. 321, pp. 522-525.

Jones, A., et al., (2007), "Blood-Brain Barrier Transport of Therapeutics via Receptor-Mediation", Pharm Res., 24(9): 1759-1771.

Joos, B., et al., 2006, "Long-Term Multiple-Dose Pharmacokinetics of Human Monoclonal Antibodies (MAbs) against Human Immunodeficiency Virus Type 1 Envelope gp120 (MAb 2G12) and gp41 (MAbs 4E10 and 2F5)", Antimicrob Agents Chemother 50, 1773-1779.

Jubala, C.M., et al. (2005), "CD20 Expression in Normal Canine B Cells and in Canine non-Hodgkin Lymphoma" Vet Pathol 42: 468-476.

\* cited by examiner

Mature Human J Chain

- QEDERIVLVDNKCKCARITSRIIRSSEDPNEDIVERNI
  RIIVPLNNRENISDPTSPLRTRFVYHLSDLCKKCDPT
  EVELDNQIVTATQSNICDEDSATETCYTYDRNKCYT
  AVVPLVYGGETKMVETALTPDACYPD (SEQ ID NO: 1)
- Number of amino acids: 137
- Molecular weight: 15594.4
- Theoretical pI: 4.59

FIG. 3

```
Hum = Human         NP_653247     23-159
Chm = Chimpanzee    XP_001160135  39-175
Gor = Gorilla       XP_004038830  23-159
Ora = Orangutan     NP_001125381  23-159
Gib = Gibbon        XP_003265761  39-175
Mar = Marmoset      XP_003732538  32-168
Cyn = Cynomolgus Monkey NP_001247815 23-159
Bab = Baboon        XP_003898844  23-159
Squ = Squirrel Monkey XP_003931978 23-159
Shr = Tree Shrew    XP_006142955  25-160
Dol = Dolphin       XP_004328961  25-158
Kil = Killer Whale  XP_004283629  25-158
Ele = Elephant      XP_003414110  25-158
Sea = Seal          XP_006729388  25-158
Rhi = Rhinoceros    XP_004419202  25-157
Cat = House Cat     XP_003985350  25-158
Wol = Wolf          XP_532398     26-159
Pan = Giant Panda   EFB23253      1-134
Fer = Ferret        XP_004766376  26-158
Hor = Horse         NP_001271464  25-158
Gui = Guinea Pig    NP_001265705  25-160
Cam = Camel         XP_006188738  25-158
Goa = Goat          XP_005681786  25-158
Chn = Chinchilla    XP_005392838  94-229
Ham = Hamster       XP_005068228  24-160
She = Sheep         XP_004009937  25-158
BBa = Brown Bat     XP_006094475  25-158
Ant = Antelope      XP_005983836  25-158
Cow = Cow           NP_786967     25-157
Mou = Mouse         NP_690052     23-159
Rat = Rat           EDL88516      23-159
Hed = Hedgehog      XP_004703237  25-157
Rab = Rabbit        P23108        1-136
Opo = Opossum       XP_003341415  29-162
All = Alligator     XP_006270094  26-159
Tur = Turtle        XP_005304167  26-159
Tas = Tasmania Devil XP_003772863 27-160
Pla = Platypus      XP_003430954  36-160
Par = Parakeet      XP_005142787  28-160
Duc = Duck          XP_005031370  28-160
Chi = Chicken       NP_989594     26-158
Tur = Turkey        XP_003205717  27-159
Fal = Falcon        XP_005243236  29-160
Spa = Sparrow       XP_005492217  29-158
```

FIG. 4

```
             1         10        20        30        40        50        60
            23        30        40        50        60        70        80        90
Hum    QEDERIVLVDNKCKCARITSRIIRSSEDPNEDIVERNIRIIVPLNNRENISDPTSPLRTRFVYHLSDLC
Chm    ....................................................................
Gor    ....................................................................
Ora    ....................................................................
Gib    .........................H..........................................
Mar    ...............................N.................................K........
Cyn    ..G...............................................................K........
Bab    ..G...............................................................K........
Squ    ........A..................NN...........V........................K........
Shr    ..KGT.........QV.....P.P....Q.............G......................K........
Dol    ....T................P.A...SQ.............S......................K........
Kil    ....T................P.A...SQ.............S......................K........
Ele    K...TL......V........P.K...SQ.....................................K........
Seal   ..G.T......Q.........P.P.N....................................V..K........
Rhi    .....-......V........P.P..........H...V.......................Q...........
Cat    ....T.......V.V......P.A........................................N.......V.
Wol    .E..T......Q.........P.PD....................................V..K........
Pan    ..G.T......Q.........P.P.....................................V..K........
Fer    .GMT..A....Q.V.......P.P.......I..............................V..N........
Hor    .G....A......V.V.....P.P.N.....L..H....I.V.S..................V..K........
Gui    .E..T.A....Q...V...V..NPDN.V......H.........S....................K........
Cam    ...ST................P.P...SQ.....................................K.E......
Goa    .N...................P.A...SQ.............S....................M..K........
Chn    .EKKTI.A....Q...VS..V...P.N........Y.....V....................R..Q........
Ham    DN.KTI.A....M.T.V......T.N..........V...........................K........
She    .N...................P.A...SQ.............S....................M..K........
BBa    ....T.A........V...V.P.PD..TQE.........V.........................K......EM.
Ant    .N...................P.A...SQ......V......S....................M..K........
Cow    .N....-..............P.A...SQ......V......S....................M..K........
Mou    D..ATI.A....M.T.V......P.T.................V....................RN.......V.
Rat    DNKGTI.A....M.T.......P.P..........S...V........................V..N.......V.
Hed    K..GT........V.V.A.S.P.T.....E.L.K........GS......N..V..T....MT..Y
Rab    ...ST......Q.V........DPDN.S..............T...................E.K.N.AN..
Opo    ...GRI......V.V...LVP.KDN.E.KV......L....R..................V......R.....
All    E.W.EH......Q.V.V..KFVP.KDN.Q.E.L......V....KS.M..............T...R..E..
Tur    E.A.EH........V..KFVP.KDN.Q.EVLV.....V....LS.K................V..T...R..E..
Tas    ...GRI....Q.V.V...LVP.KDN.EVEV......L....K........N..V..N....R..N..
Pla    .....T.V..KFVP.K...SVKVL.....V.I..KA.Q.........P......E..K..
Par    ..MER...N...Q.VTV..KLV..K.N...E.LQ.....L...KA.......L......T...RMT...
Duc    DG.ER...N.....TTV...LVP.K.N.D.E.L......T...RS.Q...........T...RMAE..
Chi    DG.ER...N.....VTV..KFVP.KDN.E.EVL..........KS..............T...RMTE..
Tur    DG.ER...N.....VTV..KFVP.KDN.E.EVL..........KS.Q............N...RMTE..
Fal    .DEH...N...Q.VTV..KFVP.K...G.EVL......L...RA.......M.....T...RMTE..
Spa    ..EY...N...Q.VTV..KFVP.Q.N.Q.EVL..........KA.......L.....T...R..E..
```

FIG. 4 (Cont.)

```
            70        80        90       100       110       120       130
                    100       110       120       130       140       150
Hum  KKCDPTEVELDNQIVTATQSNICDEDSAT-ETCYTYDRNKCYTAVVPLVYGGETKMVETALTPDACYPD
Chm  ............................-............R.........................
Gor  ............................-.....................K................
Ora  .......I....................-......................A...............
Gib  .......I....................-.................L....................
Mar  ............................-..................F........S.....S....
Cyn  ............................-..................T........Q.....S....
Bab  .........L..................-..................T.R......Q.....S....
Squ  ............................-..................T..F......KAT....S....
Shr  ....L.......................-..................TM...IF..K....Q.....S....
Dol  ....L.......V...............I---...............NR...T...K..........S....
Kil  ....L.......V...............I---...............NR...T...K..........S....
Ele  .....V......V...............---................NT...I...K....T.....S...R.
Sea  .....V......V.I.S...L.......---................NW..FT...Q..........S....
Rhi  ............V...............---..I..A..........NR...T......V.......S....
Cat  .....V...........M.S.......E.---.V..............NR..FT...V.R........S....
Wol  ....LV......V.I.S...L....T---..................NR..IM...Q..........S....
Pan  .....V....G....I.S...L......---................NR..FT...Q.R........S....
Fer  .....V......I.S...L.........---................NW..FT...Q....Q.....S....
Hor  .....V......V..S..........E.---....A............NR...T...Q..I.......S....
Gui  .....V....D.V.......L.ED.REP-...................N....S...K..L.TA.....S....
Cam  ....L.....G.RV......L..D.I---..................NK..FT.D.............S....
Goa  ....TR....ED.V...S......R.T---.................NR.K.N.R.Q...........S....
Chn  .....V....N..V......L.E..GEP-....A.N.............T......P.KV.....S..A.
Ham  .....V.....DH....S..T..S...VVP....M.N........M...T.R......PS.....S....
She  ....TR....ED.V...S......R.T---.................NR.K.N.R.Q..L........S....
BBa  ....T.Q...E..V..............N---................NK..FS...K.V........ES....
Ant  .R..TR....ED.V...S......R.T---.................NR.K.N.R.Q...........S....
Cow  ....T.....ED.V...S......S.A---.................NR.K.S.R.Q...........S....
Mou  .....V....ED.V.........N..DGVP....M............TM...R.H......QA.....S....
Rat  .....V....ED.V.........SG..GVP....M............M...R.H......Q.......S....
Hed  .....V......V.......G....---...................N....T...K.Y..R......S....
Rab  .......I......VF..S.....PD.DYS-................TL..ITHR.G.R..KAT....S.....
Opo  .......L..N.EV......N..DT.---..................STAA.YLE...RL.T......ES..N.
All  .......I..GG.....Q..TD.SKS----D................TTF.FA...Q..NI.A....AS..A.
Tur  ..........GDRV...E...N.SSS----D................TTF.FF...KINT.QA....ES..A.
Tas  ..R..I.L..G.E........NWSCG-----.................STAL.DL..KST..T.....ES..S.
Pla  Q...Q......HEV....RG.S..RPG---DD...........MSTI.FT......V.N.V...ES....
Par  .....V.F..GGE.YK.Q...S...P----..........D....TNF.FL.H....NLQAV...AS..A.
Duc  .....V....GGE.YE.Q..TS.N.P----......N.D....TTF.FI.H....HIQA....AS..A.
Chi  .....V.I..GGETYQ.Q...S.N.P----......N.D....TTF.F..H....HIQA....TS..AE
Tur  .....V.I..GGETYQ.Q..TS.N.P----......N.D....TTI.F..Q....QIQA....AS..A.
Fal  .....V....GGE.YK.Q..TS.N.P----......N.D....TTF.FS.H..V.K.QAV...AS..A.
Spa  .N.E.I.ID.GGA.HQ.Q.G.S.E.P----Q........E..SSP...LHH..VMQ.PA.....S.F
```

FIG. 4 (Cont.)

Human vs Bat J Chain

```
Query   2    EDERIVLVDNKCKCARITSRIIRSSEDPNEDIVERNIRII------------------  41
             EDERI+LVDNKCKCARITSRII S EDP++DIVERNIRI
Sbjct  25    EDERILLVDNKCKCARITSRIIPSPEDPSQDIVERNIRIKLGDEKSMVNLWNCKLLCTAG  84

Query  42    ---------------VPLNNRENISDPTSPLRTRFVYHLSDLCKKCDPTEVELDNQIVTA  86
                            VPLNNRENISDPTSP RT FVYHLSDLCK CDPTEVELDNQ+VT
Sbjct  85    LQSKEGGMVADTAGKVPLNNRENISDPTSPRRTNFVYHLSDLCKNCDPTEVELDNQVVTV  144

Query  87    TQSNICDEDSATETCYTYDRNKCYTAVVPLVYGGETKMVETALTPDACYPD  137
             TQSNICDED+   ETCY YDRNKCYT  VPL+YGG+T MVETALTPD+CYPD
Sbjct 145    TQSNICDEDN--ETCYAYDRNKCYTNRVPLLYGGKTIMVETALTPDSCYPD  193
```

FIG. 5

Orientation of J-chain Constructs
J-αCD3:
J-chain at N-terminus        scFv αCD3 at C-terminus
αCD3-J:
scFv αCD3 at N-terminus        J-chain at C-terminus
FIG. 8

FIG. 9
antiCD3scFv-J

- MGWSYIILFLVATATGVHS**QVQLQQSGAELARPGASVKMSCKASGYTFTR
YTMHWVKQRPGQGLEWIGYINPSRGYTNYNQKFKDKATLTTDKSSSTAYM
QLSSLTSEDSAVYYCARYYDDHYSLDYWGQGTTLTVSS**GGGGSGGGGSGG
GGSQIVLTQSPAIMSASPGEKVTMTCSASSSVSYMNWYQQKSGTSPKRWI
YDTSKLASGVPAHFRGSGSGTSYSLTISGMEAEDAATYYCQQWSSNPFTF
GSGTKLEIKGGGGSGGGGSGGGGS*QEDERIVLVDNKCKCARITSRIIRSS
EDPNEDIVERNIRIIVPLNNRENISDPTSPLRTRFVYHLSDLCKKCDPTE
VELDNQIVTATQSNICDEDSATETCYTYDRNKCYTAVVPLVYGGETKMVE
TALTPDACYPDGGSE*QKLISEEDLNSAVDHHHHHH**-

FIG. 10
J-antiCD3scFv

- MKNHLLFWGVLAVFIKAVHVKA*QEDERIVLVDNKCKCARITSRIIRSSED*
  *PNEDIVERNIRIIVPLNNRENISDPTSPLRTRFVYHLSDLCKKCDPTEVE*
  *LDNQIVTATQSNICDEDSATETCYTYDRNKCYTAVVPLVYGGETKMVETA*
  *LTPDACYP*DGGGGSGGGGSGGGGSQVQLQQSGAELARPGASVKMSCKASG
  YTFTRYTMHWVKQRPGQGLEWIGYINPSRGYTNYNQKFKDKATLTTDKSS
  STAYMQLSSLTSEDSAVYYCARYYDDHYSLDYWGQGTTLTVSSGGGGSGG
  GGSGGGGSQIVLTQSPAIMSASPGEKVTMTCSASSSVSYMNWYQQKSGTS
  PKRWIYDTSKLASGVPAHFRGSGSGTSYSLTISGMEAEDAATYYCQQWSS
  NPFTFGSGTKLEIKGGGSEQKLISEEDLNSAVDHHHHHH-

Asymmetric IgM Pentamer with modified J-chain

αCD20 IgM x αCD3 J bi-specific IgM expressed

- Transient co-transfections: HC, LC, and JC

- All 5 J variant are pentamers

V15J/J15V variants *retain CDC activity*

| EC50(pM) | | | |
|---|---|---|---|
| αCD20 IgG | αCD20 IgM wt J | αCD20 IgM V15J | αCD20 IgM J15V |
| 3292 | 48.4 | 47.9 | 35.2 |

FIG. 14

Bispecific IgM: active T cell killing of B-cells
αCD20$_{IgM}$ x αCD3$_{J\ chain}$ highly potent at B-cell depletion Bi-specific IgM: αCD20 very active
Raji cells (B cells) killing by T cells with αCD20 x αCD3 IgM

Menu driven approach to Bi-specific Abs
Target cells X Effector cells: for Oncology Applications

Target Associated Antigen

Hematologic cancer
CDIM, CD19, CD20, CD22,
CD33, CD70, CD56, CD138
Epithelial tumor
EpCAM, Her2, Eph-A2
PSMA, MCSP, AGS-5
GPNMB
Carbohydrate antigens
CEA, CA-125, TADG78
Sialyl Lewis-X (CD15)
Viral Antigens
PreS1 (HBV), GP120 (HIV)

Immune Effector Cell

T Cells:
CD3 epsilon

NK Cells,
CD16, CD64
NKG2D

Macrophages
CD14

Neutrophils
CD16b, CD177

FIG. 19

SEQUENCE LISTING

```
<160> NUMBER OF SEQ ID NOS: 57

<210> SEQ ID NO 1
<211> LENGTH: 137
<212> TYPE: PRT
```

<213> ORGANISM: Homo sapiens

<400> SEQUENCE: 1

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135
```

<210> SEQ ID NO 2
<211> LENGTH: 137
<212> TYPE: PRT
<213> ORGANISM: Pan troglodytes

<400> SEQUENCE: 2

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Arg Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135
```

<210> SEQ ID NO 3
<211> LENGTH: 574
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Gln Gln Trp Gly Ala Gly Leu Leu Lys Pro Ser Glu

-continued

```
1               5                   10                  15
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Gly Arg Met Ala Trp Gly Ala Ser Val Asn Phe Asp Tyr Trp Gly
            100                 105                 110

Gln Gly Thr Leu Val Thr Val Ser Ser Gly Ser Ala Ser Ala Pro Thr
            115                 120                 125

Leu Phe Pro Leu Val Ser Cys Glu Asn Ser Pro Ser Asp Thr Ser Ser
            130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
            165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
            195                 200                 205

Cys Lys Val Gln His Pro Asn Gly Asn Lys Glu Lys Asn Val Pro Leu
210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
            245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
            275                 280                 285

Ala Lys Glu Ser Gly Pro Thr Thr Tyr Lys Val Thr Ser Thr Leu Thr
            290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
            325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
            355                 360                 365

Asp Leu Thr Thr Tyr Asp Ser Val Thr Ile Ser Trp Thr Arg Gln Asn
            370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
            405                 410                 415

Asn Ser Gly Glu Arg Phe Thr Cys Thr Val Thr His Thr Asp Leu Pro
            420                 425                 430
```

```
Ser Pro Leu Lys Gln Thr Ile Ser Arg Pro Lys Gly Val Ala Leu His
        435                 440                 445

Arg Pro Asp Val Tyr Leu Leu Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Trp Asn Thr
            515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 4
<211> LENGTH: 137
<212> TYPE: PRT
<213> ORGANISM: Pongo abelii

<400> SEQUENCE: 4

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Ile Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Ala Ala
        115                 120                 125

Leu Thr Pro Asp Ala Cys Tyr Pro Asp
    130                 135

<210> SEQ ID NO 5
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
                 20                  25                  30
Leu Asn Trp Tyr Gln Gln Lys Pro Gly Lys Ala Pro Lys Leu Leu Ile
             35                  40                  45
Tyr Ala Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Ile
                 85                  90                  95
Thr Phe Gly Gln Gly Thr Arg Leu Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 6
<211> LENGTH: 137
<212> TYPE: PRT
<213> ORGANISM: Callithrix jacchus

<400> SEQUENCE: 6

Gln Glu Asp Glu Arg Ile Val Leu Val Asp Asn Lys Cys Lys Cys Ala
 1               5                  10                  15
Arg Ile Thr Ser Arg Ile Ile Arg Ser Ser Asn Asp Pro Asn Glu Asp
             20                  25                  30
Ile Val Glu Arg Asn Ile Arg Ile Ile Val Pro Leu Asn Asn Arg Glu
             35                  40                  45
Asn Ile Ser Asp Pro Thr Ser Pro Leu Arg Thr Lys Phe Val Tyr His
 50                  55                  60
Leu Ser Asp Leu Cys Lys Lys Cys Asp Pro Thr Glu Val Glu Leu Asp
 65                  70                  75                  80
Asn Gln Ile Val Thr Ala Thr Gln Ser Asn Ile Cys Asp Glu Asp Ser
                 85                  90                  95
Ala Thr Glu Thr Cys Tyr Thr Tyr Asp Arg Asn Lys Cys Tyr Thr Ala
            100                 105                 110
Val Val Pro Leu Val Phe Gly Gly Glu Thr Lys Met Val Glu Ser Ala
            115                 120                 125
Leu Thr Pro Asp Ser Cys Tyr Pro Asp
            130                 135

<210> SEQ ID NO 7
<211> LENGTH: 137
<212> TYPE: PRT
<213> ORGANISM: Macaca mulatta
```

-continued

<400> SEQUENCE: 7

Gln Glu Gly Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Val Pro Leu Asn Asn Arg Glu
        35                  40                  45

Asn Ile Ser Asp Pro Thr Ser Pro Leu Arg Thr Lys Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Thr Tyr Gly Gly Glu Thr Lys Met Val Gln Thr Ala
            115                 120                 125

Leu Thr Pro Asp Ser Cys Tyr Pro Asp
    130                 135

<210> SEQ ID NO 8
<211> LENGTH: 137
<212> TYPE: PRT
<213> ORGANISM: Papio anubis

<400> SEQUENCE: 8

Gln Glu Gly Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Lys Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Leu Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Thr Tyr Arg Gly Glu Thr Lys Met Val Gln Thr Ala
            115                 120                 125

Leu Thr Pro Asp Ser Cys Tyr Pro Asp
    130                 135

<210> SEQ ID NO 9
<211> LENGTH: 137
<212> TYPE: PRT
<213> ORGANISM: Saimiri boliviensis

<400> SEQUENCE: 9

Gln Glu Asp Glu Arg Ile Val Leu Ala Asp Asn Lys Cys Lys Cys Ala
1               5                   10                  15

Arg Ile Thr Ser Arg Ile Arg Ser Ser Asn Asn Pro Asn Glu Asp
            20                  25                  30

Ile Val Glu Arg Asn Ile Arg Ile Val Pro Leu Asn Asn Arg Glu

```
            35                  40                  45
Asn Ile Ser Asp Pro Thr Ser Pro Leu Arg Thr Lys Phe Val Tyr His
 50                  55                  60

Leu Ser Asp Leu Cys Lys Lys Cys Asp Pro Thr Glu Val Glu Leu Asp
 65                  70                  75                  80

Asn Gln Ile Val Thr Ala Thr Gln Ser Asn Ile Cys Asp Glu Asp Ser
                 85                  90                  95

Ala Thr Glu Thr Cys Tyr Thr Tyr Asp Arg Asn Lys Cys Tyr Thr Thr
                100                 105                 110

Val Val Pro Leu Val Phe Gly Gly Glu Thr Lys Met Val Lys Ala Thr
                115                 120                 125

Leu Thr Pro Asp Ser Cys Tyr Pro Asp
                130                 135

<210> SEQ ID NO 10
<211> LENGTH: 136
<212> TYPE: PRT
<213> ORGANISM: Tupaia chinensis

<400> SEQUENCE: 10

Glu Asp Lys Gly Thr Val Leu Val Asp Asn Lys Cys Lys Cys Ala Gln
  1               5                  10                  15

Val Thr Ser Arg Ile Ile Pro Ser Glu Asp Pro Asn Gln Asp Ile
                 20                  25                  30

Val Glu Arg Asn Ile Arg Ile Val Pro Leu Gly Asn Arg Glu Asn
                 35                  40                  45

Ile Ser Asp Pro Thr Ser Pro Leu Arg Thr Lys Phe Val Tyr His Leu
 50                  55                  60

Ser Asp Leu Cys Lys Lys Cys Asp Leu Thr Glu Val Glu Leu Asp Asn
 65                  70                  75                  80

Gln Ile Val Thr Ala Thr Gln Ser Asn Ile Cys Asp Glu Asp Ser Ala
                 85                  90                  95

Thr Glu Thr Cys Tyr Thr Tyr Asp Arg Asn Lys Cys Tyr Thr Thr Met
                100                 105                 110

Val Pro Leu Ile Phe Gly Gly Lys Thr Lys Met Val Gln Thr Ala Leu
                115                 120                 125

Thr Pro Asp Ser Cys Tyr Pro Asp
                130                 135

<210> SEQ ID NO 11
<211> LENGTH: 134
<212> TYPE: PRT
<213> ORGANISM: Tursiops truncatus

<400> SEQUENCE: 11

Glu Asp Glu Arg Thr Val Leu Val Asp Asn Lys Cys Lys Cys Ala Arg
  1               5                  10                  15

Ile Thr Ser Arg Ile Ile Pro Ser Ala Glu Asp Pro Ser Gln Asp Ile
                 20                  25                  30

Val Glu Arg Asn Ile Arg Ile Ile Val Pro Leu Asn Ser Arg Glu Asn
                 35                  40                  45

Ile Ser Asp Pro Thr Ser Pro Leu Arg Thr Lys Phe Val Tyr His Leu
 50                  55                  60

Ser Asp Leu Cys Lys Lys Cys Asp Leu Thr Glu Val Glu Leu Asp Asn
 65                  70                  75                  80

Gln Val Val Thr Ala Thr Gln Ser Asn Ile Cys Asp Glu Asp Ile Glu
```

```
                    85                  90                  95
Thr Cys Tyr Thr Tyr Asp Arg Asn Lys Cys Tyr Thr Asn Arg Val Pro
            100                 105                 110
Leu Thr Tyr Gly Gly Lys Thr Lys Met Val Glu Thr Ala Leu Thr Pro
            115                 120                 125
Asp Ser Cys Tyr Pro Asp
            130

<210> SEQ ID NO 12
<211> LENGTH: 134
<212> TYPE: PRT
<213> ORGANISM: Orcinus orca

<400> SEQUENCE: 12

Glu Asp Glu Arg Thr Val Leu Val Asp Asn Lys Cys Lys Cys Ala Arg
1               5                   10                  15
Ile Thr Ser Arg Ile Ile Pro Ser Ala Glu Asp Pro Ser Gln Asp Ile
            20                  25                  30
Val Glu Arg Asn Ile Arg Ile Val Pro Leu Asn Ser Arg Glu Asn
            35                  40                  45
Ile Ser Asp Pro Thr Ser Pro Leu Arg Thr Lys Phe Val Tyr His Leu
    50                  55                  60
Ser Asp Leu Cys Lys Lys Cys Asp Leu Thr Glu Val Glu Leu Asp Asn
65                  70                  75                  80
Gln Val Val Thr Ala Thr Gln Ser Asn Ile Cys Asp Glu Asp Ile Glu
                85                  90                  95
Thr Cys Tyr Thr Tyr Asp Arg Asn Lys Cys Tyr Thr Asn Arg Val Pro
            100                 105                 110
Leu Thr Tyr Gly Gly Lys Thr Lys Met Val Glu Thr Ala Leu Thr Pro
            115                 120                 125
Asp Ser Cys Tyr Pro Asp
    130

<210> SEQ ID NO 13
<211> LENGTH: 134
<212> TYPE: PRT
<213> ORGANISM: Loxodonta africana

<400> SEQUENCE: 13

Lys Asp Glu Arg Thr Leu Leu Val Asp Asn Lys Cys Lys Cys Val Arg
1               5                   10                  15
Ile Thr Ser Arg Ile Ile Pro Ser Lys Glu Asp Pro Ser Gln Asp Ile
            20                  25                  30
Val Glu Arg Asn Ile Arg Ile Val Pro Leu Asn Asn Arg Glu Asn
            35                  40                  45
Ile Ser Asp Pro Thr Ser Pro Leu Arg Thr Lys Phe Val Tyr His Leu
    50                  55                  60
Ser Asp Leu Cys Lys Lys Cys Asp Pro Val Glu Val Glu Leu Asp Asn
65                  70                  75                  80
Gln Val Val Thr Ala Thr Gln Ser Asn Ile Cys Asp Glu Asp Ser Glu
                85                  90                  95
Thr Cys Tyr Thr Tyr Asp Arg Asn Lys Cys Tyr Thr Asn Thr Val Pro
            100                 105                 110
Leu Ile Tyr Gly Gly Lys Thr Lys Met Val Thr Thr Ala Leu Thr Pro
            115                 120                 125
Asp Ser Cys Tyr Arg Asp
```

<210> SEQ ID NO 14
<211> LENGTH: 134
<212> TYPE: PRT
<213> ORGANISM: Leptonychotes weddellii

<400> SEQUENCE: 14

Glu Asp Gly Arg Thr Val Leu Val Asp Asn Lys Cys Gln Cys Ala Arg
1               5                   10                  15

Ile Thr Ser Arg Ile Ile Pro Ser Pro Glu Asn Pro Asn Glu Asp Ile
            20                  25                  30

Val Glu Arg Asn Ile Arg Ile Val Pro Leu Asn Asn Arg Glu Asn
        35                  40                  45

Ile Ser Asp Pro Thr Ser Pro Val Arg Thr Lys Phe Val Tyr His Leu
50                  55                  60

Ser Asp Leu Cys Lys Lys Cys Asp Pro Val Glu Val Glu Leu Asp Asn
65                  70                  75                  80

Gln Val Val Ile Ala Ser Gln Ser Asn Leu Cys Asp Glu Asp Ser Glu
                85                  90                  95

Thr Cys Tyr Thr Tyr Asp Arg Asn Lys Cys Tyr Thr Asn Trp Val Pro
            100                 105                 110

Phe Thr Tyr Gly Gly Gln Thr Lys Met Val Glu Thr Ala Leu Thr Pro
            115                 120                 125

Asp Ser Cys Tyr Pro Asp
    130

<210> SEQ ID NO 15
<211> LENGTH: 133
<212> TYPE: PRT
<213> ORGANISM: Ceratotherium simum

<400> SEQUENCE: 15

Glu Asp Glu Arg Ile Leu Val Asp Asn Lys Cys Lys Cys Val Arg Ile
1               5                   10                  15

Thr Ser Arg Ile Ile Pro Ser Pro Glu Asp Pro Asn Glu Asp Ile Val
            20                  25                  30

Glu Arg His Ile Arg Ile Val Val Pro Leu Asn Asn Arg Glu Asn Ile
        35                  40                  45

Ser Asp Pro Thr Ser Pro Leu Arg Thr Gln Phe Val Tyr His Leu Ser
50                  55                  60

Asp Leu Cys Lys Lys Cys Asp Pro Thr Glu Val Glu Leu Asp Asn Gln
65                  70                  75                  80

Val Val Thr Ala Thr Gln Ser Asn Ile Cys Asp Glu Asp Ser Glu Ile
                85                  90                  95

Cys Tyr Ala Tyr Asp Arg Asn Lys Cys Tyr Thr Asn Arg Val Pro Leu
            100                 105                 110

Thr Tyr Gly Gly Glu Thr Lys Val Val Glu Thr Ala Leu Thr Pro Asp
            115                 120                 125

Ser Cys Tyr Pro Asp
    130

<210> SEQ ID NO 16
<211> LENGTH: 134
<212> TYPE: PRT
<213> ORGANISM: Felis catus

<400> SEQUENCE: 16

```
Glu Asp Glu Arg Thr Val Leu Val Asp Asn Lys Cys Lys Cys Val Arg
1               5                   10                  15

Val Thr Ser Arg Ile Ile Pro Ser Ala Glu Asp Pro Asn Glu Asp Ile
            20                  25                  30

Val Glu Arg Asn Ile Arg Ile Ile Val Pro Leu Asn Asn Arg Glu Asn
        35                  40                  45

Ile Ser Asp Pro Thr Ser Pro Leu Arg Thr Asn Phe Val Tyr His Leu
    50                  55                  60

Ser Asp Val Cys Lys Lys Cys Asp Pro Val Glu Val Glu Leu Asp Asn
65                  70                  75                  80

Gln Ile Val Met Ala Ser Gln Ser Asn Ile Cys Asp Glu Glu Ser Glu
                85                  90                  95

Val Cys Tyr Thr Tyr Asp Arg Asn Lys Cys Tyr Thr Asn Arg Val Pro
            100                 105                 110

Phe Thr Tyr Gly Gly Val Thr Arg Met Val Glu Thr Ala Leu Thr Pro
            115                 120                 125

Asp Ser Cys Tyr Pro Asp
        130
```

<210> SEQ ID NO 17
<211> LENGTH: 134
<212> TYPE: PRT
<213> ORGANISM: Canis familiaris

<400> SEQUENCE: 17

```
Glu Glu Glu Arg Thr Val Leu Val Asp Asn Lys Cys Gln Cys Ala Arg
1               5                   10                  15

Ile Thr Ser Arg Ile Ile Pro Ser Pro Asp Pro Asn Glu Asp Ile
            20                  25                  30

Val Glu Arg Asn Ile Arg Ile Ile Val Pro Leu Asn Asn Arg Glu Asn
        35                  40                  45

Ile Ser Asp Pro Thr Ser Pro Val Arg Thr Lys Phe Val Tyr His Leu
    50                  55                  60

Ser Asp Leu Cys Lys Lys Cys Asp Leu Val Glu Val Glu Leu Asp Asn
65                  70                  75                  80

Gln Val Val Ile Ala Ser Gln Ser Asn Leu Cys Asp Glu Asp Thr Glu
                85                  90                  95

Thr Cys Tyr Thr Tyr Asp Arg Asn Lys Cys Tyr Thr Asn Arg Val Pro
            100                 105                 110

Ile Met Tyr Gly Gly Gln Thr Lys Met Val Glu Thr Ala Leu Thr Pro
            115                 120                 125

Asp Ser Cys Tyr Pro Asp
        130
```

<210> SEQ ID NO 18
<211> LENGTH: 134
<212> TYPE: PRT
<213> ORGANISM: Ailuropoda melanoleuca

<400> SEQUENCE: 18

```
Glu Asp Gly Arg Thr Val Leu Val Asp Asn Lys Cys Gln Cys Ala Arg
1               5                   10                  15

Ile Thr Ser Arg Ile Ile Pro Ser Pro Glu Asp Pro Asn Glu Asp Ile
            20                  25                  30

Val Glu Arg Asn Ile Arg Ile Ile Val Pro Leu Asn Asn Arg Glu Asn
        35                  40                  45
```

```
Ile Ser Asp Pro Thr Ser Pro Val Arg Thr Lys Phe Val Tyr His Leu
    50                  55                  60

Ser Asp Leu Cys Lys Lys Cys Asp Pro Val Glu Val Glu Leu Gly Asn
65                  70                  75                  80

Gln Ile Val Ile Ala Ser Gln Ser Asn Leu Cys Asp Glu Asp Ser Glu
                85                  90                  95

Thr Cys Tyr Thr Tyr Asp Arg Asn Lys Cys Tyr Thr Asn Arg Val Pro
            100                 105                 110

Phe Thr Tyr Gly Gly Gln Thr Arg Met Val Glu Thr Ala Leu Thr Pro
            115                 120                 125

Asp Ser Cys Tyr Pro Asp
        130
```

<210> SEQ ID NO 19
<211> LENGTH: 133
<212> TYPE: PRT
<213> ORGANISM: Mustela furo

<400> SEQUENCE: 19

```
Asp Gly Met Thr Val Leu Ala Asp Asn Lys Cys Gln Cys Val Arg Ile
1               5                   10                  15

Thr Ser Arg Ile Ile Pro Ser Pro Glu Asp Pro Asn Glu Asp Ile Ile
                20                  25                  30

Glu Arg Asn Ile Arg Ile Ile Val Pro Leu Asn Asn Arg Glu Asn Ile
            35                  40                  45

Ser Asp Pro Thr Ser Pro Val Arg Thr Asn Phe Val Tyr His Leu Ser
    50                  55                  60

Asp Leu Cys Lys Lys Cys Asp Pro Val Glu Val Glu Leu Asp Asn Gln
65                  70                  75                  80

Ile Val Ile Ala Ser Gln Ser Asn Leu Cys Asp Glu Asp Ser Glu Thr
                85                  90                  95

Cys Tyr Thr Tyr Asp Arg Asn Lys Cys Tyr Thr Asn Trp Val Pro Phe
            100                 105                 110

Thr Tyr Gly Gly Gln Thr Lys Met Val Gln Thr Ala Leu Thr Pro Asp
            115                 120                 125

Ser Cys Tyr Pro Asp
    130
```

<210> SEQ ID NO 20
<211> LENGTH: 134
<212> TYPE: PRT
<213> ORGANISM: Equus caballus

<400> SEQUENCE: 20

```
Glu Gly Glu Arg Ile Val Leu Ala Asp Asn Lys Cys Lys Cys Val Arg
1               5                   10                  15

Val Thr Ser Arg Ile Ile Pro Ser Pro Glu Asn Pro Asn Glu Asp Ile
                20                  25                  30

Leu Glu Arg His Ile Arg Ile Ile Pro Val Asn Ser Arg Glu Asn
            35                  40                  45

Ile Ser Asp Pro Thr Ser Pro Val Arg Thr Lys Phe Val Tyr His Leu
    50                  55                  60

Ser Asp Leu Cys Lys Lys Cys Asp Pro Val Glu Val Glu Leu Asp Asn
65                  70                  75                  80

Gln Val Val Thr Ala Ser Gln Ser Asn Ile Cys Asp Glu Glu Ser Glu
                85                  90                  95
```

Thr Cys Tyr Ala Tyr Asp Arg Asn Lys Cys Tyr Thr Asn Arg Val Pro
            100                 105                 110

Leu Thr Tyr Gly Gly Gln Thr Lys Ile Val Glu Thr Ala Leu Thr Pro
            115                 120                 125

Asp Ser Cys Tyr Pro Asp
        130

<210> SEQ ID NO 21
<211> LENGTH: 136
<212> TYPE: PRT
<213> ORGANISM: Cavia porcellus

<400> SEQUENCE: 21

Glu Glu Glu Arg Thr Val Leu Ala Asp Asn Lys Cys Gln Cys Ala Arg
1               5                   10                  15

Val Thr Ser Arg Val Ile Arg Asn Pro Asp Asn Pro Val Glu Asp Ile
            20                  25                  30

Val Glu Arg His Ile Arg Ile Ile Val Pro Leu Asn Ser Arg Glu Asn
            35                  40                  45

Ile Ser Asp Pro Thr Ser Pro Leu Arg Thr Lys Phe Val Tyr His Leu
50                  55                  60

Ser Asp Leu Cys Lys Lys Cys Asp Pro Val Glu Val Glu Leu Asp Asp
65                  70                  75                  80

Gln Val Val Thr Ala Thr Gln Ser Asn Leu Cys Glu Asp Asp Arg Glu
                85                  90                  95

Pro Glu Thr Cys Tyr Thr Tyr Asp Arg Asn Lys Cys Tyr Thr Asn Val
            100                 105                 110

Val Pro Leu Ser Tyr Gly Gly Lys Thr Lys Leu Val Thr Ala Ala Leu
            115                 120                 125

Thr Pro Asp Ser Cys Tyr Pro Asp
        130                 135

<210> SEQ ID NO 22
<211> LENGTH: 134
<212> TYPE: PRT
<213> ORGANISM: Camelus ferus

<400> SEQUENCE: 22

Glu Asp Glu Ser Thr Val Leu Val Asp Asn Lys Cys Lys Cys Ala Arg
1               5                   10                  15

Ile Thr Ser Arg Ile Ile Pro Ser Pro Glu Asp Pro Ser Gln Asp Ile
            20                  25                  30

Val Glu Arg Asn Ile Arg Ile Ile Val Pro Leu Asn Asn Arg Glu Asn
            35                  40                  45

Ile Ser Asp Pro Thr Ser Pro Leu Arg Thr Lys Phe Glu Tyr His Leu
50                  55                  60

Ser Asp Leu Cys Lys Lys Cys Asp Leu Thr Glu Val Glu Leu Gly Asn
65                  70                  75                  80

Arg Val Val Thr Ala Thr Gln Ser Asn Leu Cys Asp Asp Asp Ile Glu
                85                  90                  95

Thr Cys Thr Tyr Asp Arg Asn Lys Cys Tyr Thr Asn Lys Val Pro
            100                 105                 110

Phe Thr Tyr Asp Gly Glu Thr Lys Met Val Glu Thr Ala Leu Thr Pro
            115                 120                 125

Asp Ser Cys Tyr Pro Asp
        130

```
<210> SEQ ID NO 23
<211> LENGTH: 134
<212> TYPE: PRT
<213> ORGANISM: Capra hircus

<400> SEQUENCE: 23
```

| | | | | | | | | | | | | | | |
|---|---|---|---|---|---|---|---|---|---|---|---|---|---|---|
| Glu | Asn | Glu | Arg | Ile | Val | Leu | Val | Asp | Asn | Lys | Cys | Lys | Cys | Ala | Arg |
| 1 | | | | 5 | | | | | 10 | | | | | 15 |

| Ile | Thr | Ser | Arg | Ile | Ile | Pro | Ser | Ala | Glu | Asp | Pro | Ser | Gln | Asp | Ile |
|---|---|---|---|---|---|---|---|---|---|---|---|---|---|---|---|
| | | | 20 | | | | | 25 | | | | | 30 | | |

| Val | Glu | Arg | Asn | Ile | Arg | Ile | Ile | Val | Pro | Leu | Asn | Ser | Arg | Glu | Asn |
|---|---|---|---|---|---|---|---|---|---|---|---|---|---|---|---|
| | | | 35 | | | | | 40 | | | | | 45 | | |

| Ile | Ser | Asp | Pro | Thr | Ser | Pro | Met | Arg | Thr | Lys | Phe | Val | Tyr | His | Leu |
|---|---|---|---|---|---|---|---|---|---|---|---|---|---|---|---|
| 50 | | | | | 55 | | | | | 60 | | | | | |

| Ser | Asp | Leu | Cys | Lys | Lys | Cys | Asp | Thr | Arg | Glu | Val | Glu | Leu | Glu | Asp |
|---|---|---|---|---|---|---|---|---|---|---|---|---|---|---|---|
| 65 | | | | | 70 | | | | | 75 | | | | | 80 |

| Gln | Val | Val | Thr | Ala | Ser | Gln | Ser | Asn | Ile | Cys | Asp | Arg | Asp | Thr | Glu |
|---|---|---|---|---|---|---|---|---|---|---|---|---|---|---|---|
| | | | | 85 | | | | | 90 | | | | | 95 | |

| Thr | Cys | Tyr | Thr | Tyr | Asp | Arg | Asn | Lys | Cys | Tyr | Thr | Asn | Arg | Val | Lys |
|---|---|---|---|---|---|---|---|---|---|---|---|---|---|---|---|
| | | | 100 | | | | | 105 | | | | | 110 | | |

| Leu | Asn | Tyr | Arg | Gly | Gln | Thr | Lys | Met | Val | Glu | Thr | Ala | Leu | Thr | Pro |
|---|---|---|---|---|---|---|---|---|---|---|---|---|---|---|---|
| | | | 115 | | | | | 120 | | | | | 125 | | |

| Asp | Ser | Cys | Tyr | Pro | Asp |
|---|---|---|---|---|---|
| | 130 | | | | |

```
<210> SEQ ID NO 24
<211> LENGTH: 136
<212> TYPE: PRT
<213> ORGANISM: Chinchilla lanigera

<400> SEQUENCE: 24
```

| Glu | Glu | Lys | Lys | Thr | Ile | Leu | Ala | Asp | Asn | Lys | Cys | Gln | Cys | Ala | Arg |
|---|---|---|---|---|---|---|---|---|---|---|---|---|---|---|---|
| 1 | | | | 5 | | | | | 10 | | | | | 15 | |

| Val | Ser | Ser | Arg | Val | Ile | Arg | Ser | Pro | Glu | Asn | Pro | Asn | Glu | Asp | Ile |
|---|---|---|---|---|---|---|---|---|---|---|---|---|---|---|---|
| | | | 20 | | | | | 25 | | | | | 30 | | |

| Val | Glu | Arg | Tyr | Ile | Arg | Ile | Ile | Val | Pro | Val | Asn | Asn | Arg | Glu | Asn |
|---|---|---|---|---|---|---|---|---|---|---|---|---|---|---|---|
| | | | 35 | | | | | 40 | | | | | 45 | | |

| Ile | Ser | Asp | Pro | Thr | Ser | Pro | Arg | Arg | Thr | Gln | Phe | Val | Tyr | His | Leu |
|---|---|---|---|---|---|---|---|---|---|---|---|---|---|---|---|
| | 50 | | | | | 55 | | | | | 60 | | | | |

| Ser | Asp | Leu | Cys | Lys | Lys | Cys | Asp | Pro | Val | Glu | Val | Glu | Leu | Asn | Asn |
|---|---|---|---|---|---|---|---|---|---|---|---|---|---|---|---|
| 65 | | | | | 70 | | | | | 75 | | | | | 80 |

| Gln | Val | Val | Thr | Ala | Thr | Gln | Ser | Asn | Leu | Cys | Glu | Glu | Asp | Gly | Glu |
|---|---|---|---|---|---|---|---|---|---|---|---|---|---|---|---|
| | | | | 85 | | | | | 90 | | | | | 95 | |

| Pro | Glu | Thr | Cys | Tyr | Ala | Tyr | Asn | Arg | Asn | Lys | Cys | Tyr | Thr | Ala | Val |
|---|---|---|---|---|---|---|---|---|---|---|---|---|---|---|---|
| | | | 100 | | | | | 105 | | | | | 110 | | |

| Val | Pro | Leu | Thr | Tyr | Gly | Gly | Glu | Thr | Lys | Pro | Val | Lys | Val | Ala | Leu |
|---|---|---|---|---|---|---|---|---|---|---|---|---|---|---|---|
| | | | 115 | | | | | 120 | | | | | 125 | | |

| Thr | Pro | Asp | Ser | Cys | Tyr | Ala | Asp |
|---|---|---|---|---|---|---|---|
| | 130 | | | | | 135 | |

```
<210> SEQ ID NO 25
<211> LENGTH: 137
<212> TYPE: PRT
<213> ORGANISM: Mesocricetus auratus

<400> SEQUENCE: 25
```

```
Asp Asn Glu Lys Thr Ile Leu Ala Asp Asn Lys Cys Met Cys Thr Arg
1               5                   10                  15

Val Thr Ser Arg Ile Ile Arg Ser Thr Glu Asn Pro Asn Glu Asp Ile
            20                  25                  30

Val Glu Arg Asn Ile Arg Ile Val Pro Leu Asn Asn Arg Glu Asn
            35                  40                  45

Ile Ser Asp Pro Thr Ser Pro Leu Arg Thr Lys Phe Val Tyr His Leu
50                  55                  60

Ser Asp Leu Cys Lys Lys Cys Asp Pro Val Glu Val Glu Leu Asp Asp
65                  70                  75                  80

His Ile Val Thr Ala Ser Gln Ser Thr Ile Cys Ser Glu Asp Ser Val
                85                  90                  95

Val Pro Glu Thr Cys Tyr Met Tyr Asn Arg Asn Lys Cys Tyr Thr Ala
            100                 105                 110

Met Val Pro Leu Thr Tyr Arg Gly Glu Thr Lys Met Val Pro Ser Ala
            115                 120                 125

Leu Thr Pro Asp Ser Cys Tyr Pro Asp
            130                 135
```

<210> SEQ ID NO 26
<211> LENGTH: 134
<212> TYPE: PRT
<213> ORGANISM: Ovis aries

<400> SEQUENCE: 26

```
Glu Asn Glu Arg Ile Val Leu Val Asp Asn Lys Cys Lys Cys Ala Arg
1               5                   10                  15

Ile Thr Ser Arg Ile Ile Pro Ser Ala Glu Asp Pro Ser Gln Asp Ile
            20                  25                  30

Val Glu Arg Asn Ile Arg Ile Val Pro Leu Asn Ser Arg Glu Asn
            35                  40                  45

Ile Ser Asp Pro Thr Ser Pro Met Arg Thr Lys Phe Val Tyr His Leu
50                  55                  60

Ser Asp Leu Cys Lys Lys Cys Asp Thr Arg Glu Val Glu Leu Glu Asp
65                  70                  75                  80

Gln Val Val Thr Ala Ser Gln Ser Asn Ile Cys Asp Arg Asp Thr Glu
                85                  90                  95

Thr Cys Tyr Thr Tyr Asp Arg Asn Lys Cys Tyr Thr Asn Arg Val Lys
            100                 105                 110

Leu Asn Tyr Arg Gly Gln Thr Lys Leu Val Glu Thr Ala Leu Thr Pro
            115                 120                 125

Asp Ser Cys Tyr Pro Asp
130
```

<210> SEQ ID NO 27
<211> LENGTH: 134
<212> TYPE: PRT
<213> ORGANISM: Myotis lucifugus

<400> SEQUENCE: 27

```
Glu Asp Glu Arg Thr Val Leu Ala Asp Asn Lys Cys Lys Cys Ala Arg
1               5                   10                  15

Val Thr Ser Arg Val Ile Pro Ser Asp Asp Pro Thr Gln Glu Ile
            20                  25                  30

Val Glu Arg Asn Ile Arg Ile Ile Val Pro Val Asn Asn Arg Glu Asn
            35                  40                  45
```

```
Ile Ser Asp Pro Thr Ser Pro Leu Arg Thr Lys Phe Val Tyr His Leu
    50              55                  60

Ser Glu Met Cys Lys Lys Cys Asp Thr Thr Gln Val Glu Leu Glu Asn
65                  70                  75                  80

Gln Val Val Thr Ala Thr Gln Ser Asn Ile Cys Asp Glu Asp Asn Glu
                85                  90                  95

Thr Cys Tyr Thr Tyr Asp Arg Asn Lys Cys Tyr Thr Asn Lys Val Pro
            100                 105                 110

Phe Ser Tyr Gly Gly Lys Thr Val Met Val Glu Thr Ala Leu Thr Pro
            115                 120                 125

Glu Ser Cys Tyr Pro Asp
    130
```

<210> SEQ ID NO 28
<211> LENGTH: 134
<212> TYPE: PRT
<213> ORGANISM: Pantholops hodgsonii

<400> SEQUENCE: 28

```
Glu Asn Glu Arg Ile Val Leu Val Asp Asn Lys Cys Lys Cys Ala Arg
1               5                   10                  15

Ile Thr Ser Arg Ile Ile Pro Ser Ala Glu Asp Pro Ser Gln Asp Ile
            20                  25                  30

Val Glu Arg Asn Val Arg Ile Ile Val Pro Leu Asn Ser Arg Glu Asn
            35                  40                  45

Ile Ser Asp Pro Thr Ser Pro Met Arg Thr Lys Phe Val Tyr His Leu
    50              55                  60

Ser Asp Leu Cys Lys Arg Cys Asp Thr Arg Glu Val Glu Leu Glu Asp
65                  70                  75                  80

Gln Val Val Thr Ala Ser Gln Ser Asn Ile Cys Asp Arg Asp Thr Glu
                85                  90                  95

Thr Cys Tyr Thr Tyr Asp Arg Asn Lys Cys Tyr Thr Asn Arg Val Lys
            100                 105                 110

Leu Asn Tyr Arg Gly Gln Thr Lys Met Val Glu Thr Ala Leu Thr Pro
            115                 120                 125

Asp Ser Cys Tyr Pro Asp
    130
```

<210> SEQ ID NO 29
<211> LENGTH: 133
<212> TYPE: PRT
<213> ORGANISM: Bos taurus

<400> SEQUENCE: 29

```
Glu Asn Glu Arg Ile Val Val Asp Asn Lys Cys Lys Cys Ala Arg Ile
1               5                   10                  15

Thr Ser Arg Ile Ile Pro Ser Ala Glu Asp Pro Ser Gln Asp Ile Val
            20                  25                  30

Glu Arg Asn Val Arg Ile Ile Val Pro Leu Asn Ser Arg Glu Asn Ile
            35                  40                  45

Ser Asp Pro Thr Ser Pro Met Arg Thr Lys Phe Val Tyr His Leu Ser
    50              55                  60

Asp Leu Cys Lys Lys Cys Asp Thr Thr Glu Val Glu Leu Glu Asp Gln
65                  70                  75                  80

Val Val Thr Ala Ser Gln Ser Asn Ile Cys Asp Ser Asp Ala Glu Thr
                85                  90                  95
```

```
Cys Tyr Thr Tyr Asp Arg Asn Lys Cys Tyr Thr Asn Arg Val Lys Leu
                100                 105                 110

Ser Tyr Arg Gly Gln Thr Lys Met Val Glu Thr Ala Leu Thr Pro Asp
            115                 120                 125

Ser Cys Tyr Pro Asp
        130

<210> SEQ ID NO 30
<211> LENGTH: 137
<212> TYPE: PRT
<213> ORGANISM: Mus musculus

<400> SEQUENCE: 30

Asp Asp Glu Ala Thr Ile Leu Ala Asp Asn Lys Cys Met Cys Thr Arg
1               5                   10                  15

Val Thr Ser Arg Ile Ile Pro Ser Thr Glu Asp Pro Asn Glu Asp Ile
            20                  25                  30

Val Glu Arg Asn Ile Arg Ile Val Val Pro Leu Asn Asn Arg Glu Asn
        35                  40                  45

Ile Ser Asp Pro Thr Ser Pro Leu Arg Arg Asn Phe Val Tyr His Leu
    50                  55                  60

Ser Asp Val Cys Lys Lys Cys Asp Pro Val Glu Val Glu Leu Glu Asp
65                  70                  75                  80

Gln Val Val Thr Ala Thr Gln Ser Asn Ile Cys Asn Glu Asp Asp Gly
                85                  90                  95

Val Pro Glu Thr Cys Tyr Met Tyr Asp Arg Asn Lys Cys Tyr Thr Thr
            100                 105                 110

Met Val Pro Leu Arg Tyr His Gly Glu Thr Lys Met Val Gln Ala Ala
        115                 120                 125

Leu Thr Pro Asp Ser Cys Tyr Pro Asp
    130                 135

<210> SEQ ID NO 31
<211> LENGTH: 137
<212> TYPE: PRT
<213> ORGANISM: Rattus norvegicus

<400> SEQUENCE: 31

Asp Asn Lys Gly Thr Ile Leu Ala Asp Asn Lys Cys Met Cys Thr Arg
1               5                   10                  15

Ile Thr Ser Arg Ile Ile Pro Ser Pro Glu Asp Pro Asn Glu Asp Ile
            20                  25                  30

Val Glu Arg Ser Ile Arg Ile Val Val Pro Leu Asn Asn Arg Glu Asn
        35                  40                  45

Ile Ser Asp Pro Thr Ser Pro Val Arg Thr Asn Phe Val Tyr His Leu
    50                  55                  60

Ser Asp Val Cys Lys Lys Cys Asp Pro Val Glu Val Glu Leu Glu Asp
65                  70                  75                  80

Gln Val Val Thr Ala Thr Gln Ser Asn Ile Cys Ser Gly Asp Ser Gly
                85                  90                  95

Val Pro Glu Thr Cys Tyr Met Tyr Asp Arg Asn Lys Cys Tyr Thr Ala
            100                 105                 110

Met Val Pro Leu Arg Tyr His Gly Glu Thr Lys Met Val Gln Thr Ala
        115                 120                 125

Leu Thr Pro Asp Ser Cys Tyr Pro Asp
    130                 135
```

<210> SEQ ID NO 32
<211> LENGTH: 133
<212> TYPE: PRT
<213> ORGANISM: Echinops telfairi

<400> SEQUENCE: 32

Lys Asp Glu Gly Thr Val Leu Val Asp Asn Lys Cys Lys Cys Val Arg
1               5                   10                  15

Val Thr Ala Arg Ser Ile Pro Ser Thr Glu Asp Pro Asn Glu Glu Ile
            20                  25                  30

Leu Glu Lys Asn Ile Arg Ile Ile Val Pro Leu Gly Ser Arg Glu Asn
        35                  40                  45

Ile Ser Asp Pro Asn Ser Pro Val Arg Thr Thr Phe Val Tyr His Met
50                  55                  60

Thr Asp Leu Tyr Lys Lys Cys Asp Pro Val Glu Val Glu Leu Asp Asn
65                  70                  75                  80

Gln Val Val Thr Ala Thr Gln Ser Asn Gly Cys Asp Glu Asp Glu Thr
                85                  90                  95

Cys Tyr Thr Tyr Asp Arg Asn Lys Cys Tyr Thr Asn Val Val Pro Leu
            100                 105                 110

Thr Tyr Gly Gly Lys Thr Tyr Met Val Arg Thr Ala Leu Thr Pro Asp
        115                 120                 125

Ser Cys Tyr Pro Asp
    130

<210> SEQ ID NO 33
<211> LENGTH: 136
<212> TYPE: PRT
<213> ORGANISM: Oryctolagus cuniculus

<400> SEQUENCE: 33

Glu Asp Glu Ser Thr Val Leu Val Asp Asn Lys Cys Gln Cys Val Arg
1               5                   10                  15

Ile Thr Ser Arg Ile Ile Arg Asp Pro Asp Asn Pro Ser Glu Asp Ile
            20                  25                  30

Val Glu Arg Asn Ile Arg Ile Ile Val Pro Leu Asn Thr Arg Glu Asn
        35                  40                  45

Ile Ser Asp Pro Thr Ser Pro Leu Arg Thr Glu Phe Lys Tyr Asn Leu
50                  55                  60

Ala Asn Leu Cys Lys Lys Cys Asp Pro Thr Glu Ile Glu Leu Asp Asn
65                  70                  75                  80

Gln Val Phe Thr Ala Ser Gln Ser Asn Ile Cys Pro Asp Asp Asp Tyr
                85                  90                  95

Ser Glu Thr Cys Tyr Thr Tyr Asp Arg Asn Lys Cys Tyr Thr Thr Leu
            100                 105                 110

Val Pro Ile Thr His Arg Gly Gly Thr Arg Met Val Lys Ala Thr Leu
        115                 120                 125

Thr Pro Asp Ser Cys Tyr Pro Asp
    130                 135

<210> SEQ ID NO 34
<211> LENGTH: 134
<212> TYPE: PRT
<213> ORGANISM: Monodelphis domestica

<400> SEQUENCE: 34

Glu Asp Glu Gly Arg Ile Leu Val Asp Asn Lys Cys Lys Cys Val Arg

```
1               5                   10                  15
Val Thr Ser Arg Leu Val Pro Ser Lys Asp Asn Pro Glu Glu Lys Val
                20                  25                  30

Val Glu Arg Asn Ile Arg Leu Ile Val Pro Leu Arg Asn Arg Glu Asn
                35                  40                  45

Ile Ser Asp Pro Thr Ser Pro Val Arg Thr Arg Phe Val Tyr Arg Leu
            50                  55                  60

Ser Asp Leu Cys Lys Lys Cys Asp Pro Thr Glu Leu Glu Leu Asn Asn
65                  70                  75                  80

Glu Val Val Thr Ala Thr Gln Ser Asn Asn Cys Asp Asp Thr Ser Glu
                85                  90                  95

Thr Cys Tyr Thr Tyr Asp Arg Asn Lys Cys Tyr Thr Ser Thr Ala Ala
                100                 105                 110

Leu Tyr Leu Glu Gly Glu Thr Arg Leu Val Thr Ala Leu Thr Pro
                115                 120                 125

Glu Ser Cys Tyr Asn Asp
        130
```

<210> SEQ ID NO 35
<211> LENGTH: 134
<212> TYPE: PRT
<213> ORGANISM: Alligator mississippiensis

<400> SEQUENCE: 35

```
Glu Glu Trp Glu Glu His Val Leu Val Asp Asn Lys Cys Gln Cys Val
1               5                   10                  15

Arg Val Thr Ser Lys Phe Val Pro Ser Lys Asp Asn Pro Gln Glu Glu
                20                  25                  30

Ile Leu Glu Arg Asn Ile Arg Val Ile Val Pro Leu Lys Ser Arg Met
                35                  40                  45

Asn Ile Ser Asp Pro Thr Ser Pro Leu Arg Thr Thr Phe Val Tyr Arg
            50                  55                  60

Leu Ser Glu Leu Cys Lys Lys Cys Asp Pro Thr Glu Ile Glu Leu Gly
65                  70                  75                  80

Gly Gln Ile Val Thr Ala Gln Gln Ser Thr Asp Cys Ser Lys Ser Asp
                85                  90                  95

Thr Cys Tyr Thr Tyr Asp Arg Asn Lys Cys Tyr Thr Thr Thr Phe Pro
                100                 105                 110

Phe Ala Tyr Gly Gly Gln Thr Lys Asn Ile Glu Ala Ala Leu Thr Pro
                115                 120                 125

Ala Ser Cys Tyr Ala Asp
        130
```

<210> SEQ ID NO 36
<211> LENGTH: 134
<212> TYPE: PRT
<213> ORGANISM: Chrysemys picta

<400> SEQUENCE: 36

```
Glu Glu Ala Glu Glu His Val Leu Val Asp Asn Lys Cys Lys Cys Ala
1               5                   10                  15

Arg Val Thr Ser Lys Phe Val Pro Ser Lys Asp Asn Pro Gln Glu Glu
                20                  25                  30

Val Leu Val Arg Asn Ile Arg Val Ile Val Pro Leu Leu Ser Arg Lys
                35                  40                  45

Asn Ile Ser Asp Pro Thr Ser Pro Val Arg Thr Thr Phe Val Tyr Arg
            50                  55                  60
```

Leu Ser Glu Leu Cys Lys Lys Cys Asp Pro Thr Glu Val Glu Leu Gly
65                  70                  75                  80

Asp Arg Val Val Thr Ala Glu Gln Ser Asn Asn Cys Ser Ser Ser Asp
                85                  90                  95

Thr Cys Tyr Thr Tyr Asp Arg Asn Lys Cys Tyr Thr Thr Phe Pro
            100                 105                 110

Phe Phe Tyr Gly Gly Lys Ile Asn Thr Val Gln Ala Ala Leu Thr Pro
        115                 120                 125

Glu Ser Cys Tyr Ala Asp
    130

<210> SEQ ID NO 37
<211> LENGTH: 132
<212> TYPE: PRT
<213> ORGANISM: Sarcophilus harrisii

<400> SEQUENCE: 37

Glu Asp Glu Gly Arg Ile Leu Val Asp Asn Lys Cys Gln Cys Val Arg
1               5                   10                  15

Val Thr Ser Arg Leu Val Pro Ser Lys Asp Asn Pro Glu Val Glu Val
            20                  25                  30

Val Glu Arg Asn Ile Arg Leu Ile Val Pro Leu Lys Asn Arg Glu Asn
        35                  40                  45

Ile Ser Asp Pro Asn Ser Pro Val Arg Thr Asn Phe Val Tyr Arg Leu
50                  55                  60

Ser Asn Leu Cys Lys Lys Arg Asp Pro Ile Glu Leu Glu Leu Gly Asn
65                  70                  75                  80

Glu Ile Val Thr Ala Thr Gln Ser Asn Asn Trp Ser Cys Gly Thr Cys
                85                  90                  95

Tyr Thr Tyr Asp Arg Asn Lys Cys Tyr Thr Ser Thr Ala Leu Leu Asp
            100                 105                 110

Leu Gly Gly Lys Ser Thr Met Val Thr Thr Ala Leu Thr Pro Glu Ser
        115                 120                 125

Cys Tyr Ser Asp
    130

<210> SEQ ID NO 38
<211> LENGTH: 125
<212> TYPE: PRT
<213> ORGANISM: Ornithorhynchus anatinus

<400> SEQUENCE: 38

Asn Lys Cys Lys Cys Thr Arg Val Thr Ser Lys Phe Val Pro Ser Lys
1               5                   10                  15

Glu Asp Pro Ser Val Lys Val Leu Glu Arg Asn Ile Arg Val Ile Ile
            20                  25                  30

Pro Leu Lys Ala Arg Gln Asn Ile Ser Asp Pro Thr Ser Pro Arg
        35                  40                  45

Thr Arg Phe Val Tyr Glu Leu Ser Lys Leu Cys Gln Lys Cys Asp Gln
50                  55                  60

Thr Glu Val Glu Leu Asp His Glu Val Val Thr Ala Thr Arg Gly Asn
65                  70                  75                  80

Ser Cys Asp Arg Pro Gly Asp Asp Cys Tyr Thr Tyr Asp Arg Asn Lys
                85                  90                  95

Cys Tyr Met Ser Thr Ile Pro Phe Thr Tyr Gly Gly Glu Thr Lys Val

-continued

```
                100                 105                 110
Val Asn Thr Val Leu Thr Pro Glu Ser Cys Tyr Pro Asp
        115                 120                 125

<210> SEQ ID NO 39
<211> LENGTH: 133
<212> TYPE: PRT
<213> ORGANISM: Melopsittacus undulatus

<400> SEQUENCE: 39

Glu Asp Met Glu Arg Val Leu Val Asn Asn Lys Cys Gln Cys Val Thr
1               5                   10                  15

Val Thr Ser Lys Leu Val Arg Ser Lys Glu Asn Pro Asn Glu Glu Ile
            20                  25                  30

Leu Gln Arg Asn Ile Arg Ile Leu Val Pro Leu Lys Ala Arg Glu Asn
        35                  40                  45

Ile Ser Asp Pro Leu Ser Pro Leu Arg Thr Thr Phe Val Tyr Arg Met
50                  55                  60

Thr Asp Leu Cys Lys Lys Cys Asp Pro Val Glu Phe Glu Leu Gly Gly
65                  70                  75                  80

Glu Ile Tyr Lys Ala Gln Gln Ser Asn Ser Cys Asp Glu Pro Glu Thr
                85                  90                  95

Cys Tyr Thr Tyr Asp Arg Asp Lys Cys Tyr Thr Thr Asn Phe Pro Phe
            100                 105                 110

Leu Tyr His Gly Glu Thr Lys Asn Leu Gln Ala Val Leu Thr Pro Ala
        115                 120                 125

Ser Cys Tyr Ala Asp
        130

<210> SEQ ID NO 40
<211> LENGTH: 133
<212> TYPE: PRT
<213> ORGANISM: Anas platyrhynchos

<400> SEQUENCE: 40

Asp Gly Glu Glu Arg Val Leu Val Asn Asn Lys Cys Lys Cys Thr Thr
1               5                   10                  15

Val Thr Ser Arg Leu Val Pro Ser Lys Glu Asn Pro Asp Glu Glu Ile
            20                  25                  30

Leu Glu Arg Asn Ile Arg Ile Thr Val Pro Leu Arg Ser Arg Gln Asn
        35                  40                  45

Ile Ser Asp Pro Thr Ser Pro Leu Arg Thr Thr Phe Val Tyr Arg Met
50                  55                  60

Ala Glu Leu Cys Lys Lys Cys Asp Pro Val Glu Val Glu Leu Gly Gly
65                  70                  75                  80

Glu Ile Tyr Glu Ala Gln Gln Ser Thr Ser Cys Asn Glu Pro Glu Thr
                85                  90                  95

Cys Tyr Thr Tyr Asn Arg Asp Lys Cys Tyr Thr Thr Thr Phe Pro Phe
            100                 105                 110

Ile Tyr His Gly Glu Thr Lys His Ile Gln Ala Ala Leu Thr Pro Ala
        115                 120                 125

Ser Cys Tyr Ala Asp
        130

<210> SEQ ID NO 41
<211> LENGTH: 133
<212> TYPE: PRT
```

<213> ORGANISM: Gallus gallus

<400> SEQUENCE: 41

Asp Gly Glu Glu Arg Val Leu Val Asn Asn Lys Cys Lys Cys Val Thr
1               5                   10                  15

Val Thr Ser Lys Phe Val Pro Ser Lys Asp Asn Pro Glu Glu Glu Val
            20                  25                  30

Leu Glu Arg Asn Ile Arg Ile Ile Val Pro Leu Lys Ser Arg Glu Asn
        35                  40                  45

Ile Ser Asp Pro Thr Ser Pro Leu Arg Thr Thr Phe Val Tyr Arg Met
    50                  55                  60

Thr Glu Leu Cys Lys Lys Cys Asp Pro Val Glu Ile Glu Leu Gly Gly
65                  70                  75                  80

Glu Thr Tyr Gln Ala Gln Gln Ser Asn Ser Cys Asn Glu Pro Glu Thr
                85                  90                  95

Cys Tyr Thr Tyr Asn Arg Asp Lys Cys Tyr Thr Thr Phe Pro Phe
            100                 105                 110

Val Tyr His Gly Glu Thr Lys His Ile Gln Ala Ala Leu Thr Pro Thr
        115                 120                 125

Ser Cys Tyr Ala Glu
    130

<210> SEQ ID NO 42
<211> LENGTH: 133
<212> TYPE: PRT
<213> ORGANISM: Meleagris gallopavo

<400> SEQUENCE: 42

Asp Gly Glu Glu Arg Val Leu Val Asn Asn Lys Cys Lys Cys Val Thr
1               5                   10                  15

Val Thr Ser Lys Phe Val Pro Ser Lys Asp Asn Pro Glu Glu Glu Val
            20                  25                  30

Leu Glu Arg Asn Ile Arg Ile Ile Val Pro Leu Lys Ser Arg Gln Asn
        35                  40                  45

Ile Ser Asp Pro Thr Ser Pro Leu Arg Thr Asn Phe Val Tyr Arg Met
    50                  55                  60

Thr Glu Leu Cys Lys Lys Cys Asp Pro Val Glu Ile Glu Leu Gly Gly
65                  70                  75                  80

Glu Thr Tyr Gln Ala Gln Gln Ser Thr Ser Cys Asn Glu Pro Glu Thr
                85                  90                  95

Cys Tyr Thr Tyr Asn Arg Asp Lys Cys Tyr Thr Thr Ile Pro Phe
            100                 105                 110

Val Tyr Gln Gly Glu Thr Lys Gln Ile Gln Ala Ala Leu Thr Pro Ala
        115                 120                 125

Ser Cys Tyr Ala Asp
    130

<210> SEQ ID NO 43
<211> LENGTH: 132
<212> TYPE: PRT
<213> ORGANISM: Falco peregrinus

<400> SEQUENCE: 43

Asp Asp Glu His Val Leu Val Asn Asn Lys Cys Gln Cys Val Thr Val
1               5                   10                  15

Thr Ser Lys Phe Val Pro Ser Lys Glu Asp Pro Gly Glu Glu Val Leu
            20                  25                  30

```
Glu Arg Asn Ile Arg Ile Leu Val Pro Leu Arg Ala Arg Glu Asn Ile
            35                  40                  45

Ser Asp Pro Met Ser Pro Leu Arg Thr Thr Phe Val Tyr Arg Met Thr
 50                      55                  60

Glu Leu Cys Lys Lys Cys Asp Pro Val Glu Val Glu Leu Gly Gly Glu
 65                  70                  75                  80

Ile Tyr Lys Ala Gln Gln Ser Thr Ser Cys Asn Glu Pro Glu Thr Cys
                    85                  90                  95

Tyr Thr Tyr Asn Arg Asp Lys Cys Tyr Thr Thr Phe Pro Phe Ser
                    100                 105                 110

Tyr His Gly Glu Val Lys Lys Val Gln Ala Val Leu Thr Pro Ala Ser
            115                 120                 125

Cys Tyr Ala Asp
    130

<210> SEQ ID NO 44
<211> LENGTH: 130
<212> TYPE: PRT
<213> ORGANISM: Zonotrichia albicollis

<400> SEQUENCE: 44

Asp Glu Glu Tyr Val Leu Val Asn Asn Lys Cys Gln Cys Val Thr Val
 1               5                  10                  15

Thr Ser Lys Phe Val Pro Ser Gln Glu Asn Pro Gln Glu Glu Val Leu
                20                  25                  30

Glu Arg Asn Ile Arg Ile Val Pro Leu Lys Ala Arg Glu Asn Ile
            35                  40                  45

Ser Asp Pro Leu Ser Pro Leu Arg Thr Thr Phe Val Tyr Arg Leu Ser
 50                      55                  60

Glu Leu Cys Lys Asn Cys Glu Pro Ile Glu Ile Asp Leu Gly Gly Ala
 65                  70                  75                  80

Ile His Gln Ala Gln Gln Gly Asn Ser Cys Glu Glu Pro Gln Thr Cys
                    85                  90                  95

Tyr Thr Tyr Asp Arg Asn Glu Cys Tyr Ser Ser Pro Val Pro Leu Leu
                    100                 105                 110

His His Gly Glu Val Met Gln Val Pro Ala Ala Leu Thr Pro Asp Ser
            115                 120                 125

Cys Phe
    130

<210> SEQ ID NO 45
<211> LENGTH: 169
<212> TYPE: PRT
<213> ORGANISM: Pteropus alecto

<400> SEQUENCE: 45

Glu Asp Glu Arg Ile Leu Leu Val Asp Asn Lys Cys Lys Cys Ala Arg
 1               5                  10                  15

Ile Thr Ser Arg Ile Ile Pro Ser Pro Glu Asp Pro Ser Gln Asp Ile
                20                  25                  30

Val Glu Arg Asn Ile Arg Ile Lys Leu Gly Asp Glu Lys Ser Met Val
            35                  40                  45

Asn Leu Trp Asn Cys Lys Leu Leu Cys Thr Ala Gly Leu Gln Ser Lys
 50                      55                  60

Glu Gly Gly Met Val Ala Asp Thr Ala Gly Lys Val Pro Leu Asn Asn
 65                  70                  75                  80
```

```
Arg Glu Asn Ile Ser Asp Pro Thr Ser Pro Arg Arg Thr Asn Phe Val
                85                  90                  95

Tyr His Leu Ser Asp Leu Cys Lys Asn Cys Asp Pro Thr Glu Val Glu
            100                 105                 110

Leu Asp Asn Gln Val Val Thr Val Thr Gln Ser Asn Ile Cys Asp Glu
        115                 120                 125

Asp Asn Glu Thr Cys Tyr Ala Tyr Asp Arg Asn Lys Cys Tyr Thr Asn
    130                 135                 140

Arg Val Pro Leu Leu Tyr Gly Gly Lys Thr Ile Met Val Glu Thr Ala
145                 150                 155                 160

Leu Thr Pro Asp Ser Cys Tyr Pro Asp
                165
```

<210> SEQ ID NO 46
<211> LENGTH: 436
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 46

```
Met Gly Trp Ser Tyr Ile Ile Leu Phe Leu Val Ala Thr Ala Thr Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Ser Leu Asp Tyr Trp
        115                 120                 125

Gly Gln Gly Thr Thr Leu Thr Val Ser Ser Gly Gly Gly Ser Gly
    130                 135                 140

Gly Gly Gly Ser Gly Gly Gly Gly Ser Gln Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255
```

```
Glu Ile Lys Gly Gly Gly Ser Gly Gly Gly Ser Gly Gly
            260                 265                 270

Gly Ser Gln Glu Asp Glu Arg Ile Val Leu Val Asp Asn Lys Cys Lys
        275                 280                 285

Cys Ala Arg Ile Thr Ser Arg Ile Ile Arg Ser Ser Glu Asp Pro Asn
        290                 295                 300

Glu Asp Ile Val Glu Arg Asn Ile Arg Ile Ile Val Pro Leu Asn Asn
305                 310                 315                 320

Arg Glu Asn Ile Ser Asp Pro Thr Ser Pro Leu Arg Thr Arg Phe Val
                325                 330                 335

Tyr His Leu Ser Asp Leu Cys Lys Lys Cys Asp Pro Thr Glu Val Glu
            340                 345                 350

Leu Asp Asn Gln Ile Val Thr Ala Thr Gln Ser Asn Ile Cys Asp Glu
        355                 360                 365

Asp Ser Ala Thr Glu Thr Cys Tyr Thr Tyr Asp Arg Asn Lys Cys Tyr
    370                 375                 380

Thr Ala Val Val Pro Leu Val Tyr Gly Gly Glu Thr Lys Met Val Glu
385                 390                 395                 400

Thr Ala Leu Thr Pro Asp Ala Cys Tyr Pro Asp Gly Gly Gly Ser Glu
                405                 410                 415

Gln Lys Leu Ile Ser Glu Glu Asp Leu Asn Ser Ala Val Asp His His
            420                 425                 430

His His His His
        435

<210> SEQ ID NO 47
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp Gly
145                 150                 155                 160

Gly Gly Gly Ser Gly Gly Gly Gly Ser Gly Gly Gly Gly Ser Gln Val
```

```
                165                 170                 175
Gln Leu Gln Gln Ser Gly Ala Glu Leu Ala Arg Pro Gly Ala Ser Val
            180                 185                 190

Lys Met Ser Cys Lys Ala Ser Gly Tyr Thr Phe Thr Arg Tyr Thr Met
        195                 200                 205

His Trp Val Lys Gln Arg Pro Gly Gln Gly Leu Glu Trp Ile Gly Tyr
    210                 215                 220

Ile Asn Pro Ser Arg Gly Tyr Thr Asn Tyr Asn Gln Lys Phe Lys Asp
225                 230                 235                 240

Lys Ala Thr Leu Thr Thr Asp Lys Ser Ser Thr Ala Tyr Met Gln
            245                 250                 255

Leu Ser Ser Leu Thr Ser Glu Asp Ser Ala Val Tyr Tyr Cys Ala Arg
            260                 265                 270

Tyr Tyr Asp Asp His Tyr Ser Leu Asp Tyr Trp Gly Gln Gly Thr Thr
            275                 280                 285

Leu Thr Val Ser Ser Gly Gly Gly Gly Ser Gly Gly Gly Gly Ser Gly
            290                 295                 300

Gly Gly Gly Ser Gln Ile Val Leu Thr Gln Ser Pro Ala Ile Met Ser
305                 310                 315                 320

Ala Ser Pro Gly Glu Lys Val Thr Met Thr Cys Ser Ala Ser Ser
            325                 330                 335

Val Ser Tyr Met Asn Trp Tyr Gln Gln Lys Ser Gly Thr Ser Pro Lys
            340                 345                 350

Arg Trp Ile Tyr Asp Thr Ser Lys Leu Ala Ser Gly Val Pro Ala His
            355                 360                 365

Phe Arg Gly Ser Gly Ser Gly Thr Ser Tyr Ser Leu Thr Ile Ser Gly
        370                 375                 380

Met Glu Ala Glu Asp Ala Ala Thr Tyr Tyr Cys Gln Gln Trp Ser Ser
385                 390                 395                 400

Asn Pro Phe Thr Phe Gly Ser Gly Thr Lys Leu Glu Ile Lys Gly Gly
                405                 410                 415

Gly Ser Glu Gln Lys Leu Ile Ser Glu Glu Asp Leu Asn Ser Ala Val
            420                 425                 430

Asp His His His His His His
            435

<210> SEQ ID NO 48
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Met Asp Met Arg Val Pro Ala Gln Leu Leu Gly Leu Leu Leu Leu Trp
1               5                   10                  15

Leu Arg Gly Ala Arg Cys Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80
```

```
Val Arg Phe Ser Gly Ser Gly Ser Gly Thr Ser Tyr Ser Leu Thr Ile
            85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys
225                 230                 235

<210> SEQ ID NO 49
<211> LENGTH: 593
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Met Gly Trp Ser Tyr Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
        50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
            85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ser Gly Ser Ala Ser
130                 135                 140

Ala Pro Thr Leu Phe Pro Leu Val Ser Cys Glu Asn Ser Pro Ser Asp
145                 150                 155                 160

Thr Ser Ser Val Ala Val Gly Cys Leu Ala Gln Asp Phe Leu Pro Asp
            165                 170                 175

Ser Ile Thr Phe Ser Trp Lys Tyr Lys Asn Asn Ser Asp Ile Ser Ser
            180                 185                 190
```

-continued

Thr Arg Gly Phe Pro Ser Val Leu Arg Gly Gly Lys Tyr Ala Ala Thr
        195                 200                 205

Ser Gln Val Leu Leu Pro Ser Lys Asp Val Met Gln Gly Thr Asp Glu
210                 215                 220

His Val Val Cys Lys Val Gln His Pro Asn Gly Asn Lys Glu Lys Asn
225                 230                 235                 240

Val Pro Leu Pro Val Ile Ala Glu Leu Pro Pro Lys Val Ser Val Phe
                245                 250                 255

Val Pro Pro Arg Asp Gly Phe Phe Gly Asn Pro Arg Lys Ser Lys Leu
            260                 265                 270

Ile Cys Gln Ala Thr Gly Phe Ser Pro Arg Gln Ile Gln Val Ser Trp
        275                 280                 285

Leu Arg Glu Gly Lys Gln Val Gly Ser Gly Val Thr Thr Asp Gln Val
290                 295                 300

Gln Ala Glu Ala Lys Glu Ser Gly Pro Thr Thr Tyr Lys Val Thr Ser
305                 310                 315                 320

Thr Leu Thr Ile Lys Glu Ser Asp Trp Leu Ser Gln Ser Met Phe Thr
                325                 330                 335

Cys Arg Val Asp His Arg Gly Leu Thr Phe Gln Gln Asn Ala Ser Ser
            340                 345                 350

Met Cys Val Pro Asp Gln Asp Thr Ala Ile Arg Val Phe Ala Ile Pro
        355                 360                 365

Pro Ser Phe Ala Ser Ile Phe Leu Thr Lys Ser Thr Lys Leu Thr Cys
    370                 375                 380

Leu Val Thr Asp Leu Thr Thr Tyr Asp Ser Val Thr Ile Ser Trp Thr
385                 390                 395                 400

Arg Gln Asn Gly Glu Ala Val Lys Thr His Thr Asn Ile Ser Glu Ser
                405                 410                 415

His Pro Asn Ala Thr Phe Ser Ala Val Gly Glu Ala Ser Ile Cys Glu
            420                 425                 430

Asp Asp Trp Asn Ser Gly Glu Arg Phe Thr Cys Thr Val Thr His Thr
        435                 440                 445

Asp Leu Pro Ser Pro Leu Lys Gln Thr Ile Ser Arg Pro Lys Gly Val
    450                 455                 460

Ala Leu His Arg Pro Asp Val Tyr Leu Leu Pro Pro Ala Arg Glu Gln
465                 470                 475                 480

Leu Asn Leu Arg Glu Ser Ala Thr Ile Thr Cys Leu Val Thr Gly Phe
                485                 490                 495

Ser Pro Ala Asp Val Phe Val Gln Trp Met Gln Arg Gly Gln Pro Leu
            500                 505                 510

Ser Pro Glu Lys Tyr Val Thr Ser Ala Pro Met Pro Glu Pro Gln Ala
        515                 520                 525

Pro Gly Arg Tyr Phe Ala His Ser Ile Leu Thr Val Ser Glu Glu Glu
    530                 535                 540

Trp Asn Thr Gly Glu Thr Tyr Thr Cys Val Val Ala His Glu Ala Leu
545                 550                 555                 560

Pro Asn Arg Val Thr Glu Arg Thr Val Asp Lys Ser Thr Gly Lys Pro
                565                 570                 575

Thr Leu Tyr Asn Val Ser Leu Val Met Ser Asp Thr Ala Gly Thr Cys
            580                 585                 590

Tyr

<210> SEQ ID NO 50

<211> LENGTH: 412
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

```
Met Gly Trp Ser Tyr Ile Ile Leu Phe Leu Val Ala Thr Ala Thr Gly
1               5                   10                  15
Val His Ser Gln Val Gln Leu Val Gln Ser Gly Ala Glu Val Lys Lys
            20                  25                  30
Pro Gly Ala Ser Val Lys Val Ser Cys Lys Ala Ser Gly Tyr Thr Phe
        35                  40                  45
Ile Ser Tyr Thr Met His Trp Val Arg Gln Ala Pro Gly Gln Gly Leu
    50                  55                  60
Glu Trp Met Gly Tyr Ile Asn Pro Arg Ser Gly Tyr Thr His Tyr Asn
65                  70                  75                  80
Gln Lys Leu Lys Asp Lys Ala Thr Leu Thr Ala Asp Lys Ser Ala Ser
                85                  90                  95
Thr Ala Tyr Met Glu Leu Ser Ser Leu Arg Ser Glu Asp Thr Ala Val
            100                 105                 110
Tyr Tyr Cys Ala Arg Ser Ala Tyr Tyr Asp Tyr Asp Gly Phe Ala Tyr
        115                 120                 125
Trp Gly Gln Gly Thr Leu Val Thr Val Ser Ser Gly Gly Gly Gly Ser
    130                 135                 140
Gly Gly Gly Gly Ser Gly Gly Gly Ser Asp Ile Gln Met Thr Gln
145                 150                 155                 160
Ser Pro Ser Ser Leu Ser Ala Ser Val Gly Asp Arg Val Thr Ile Thr
                165                 170                 175
Cys Ser Ala Ser Ser Val Ser Tyr Met Asn Trp Tyr Gln Gln Lys
            180                 185                 190
Pro Gly Lys Ala Pro Lys Arg Leu Ile Tyr Asp Thr Ser Lys Leu Ala
        195                 200                 205
Ser Gly Val Pro Ser Arg Phe Ser Gly Ser Gly Ser Gly Thr Asp Phe
    210                 215                 220
Thr Leu Thr Ile Ser Ser Leu Gln Pro Glu Asp Phe Ala Thr Tyr Tyr
225                 230                 235                 240
Cys Gln Gln Trp Ser Ser Asn Pro Pro Thr Phe Gly Gly Gly Thr Lys
                245                 250                 255
Leu Glu Ile Lys Gly Gly Gly Gly Ser Gly Gly Gly Gly Ser Gly Gly
            260                 265                 270
Gly Gly Ser Gln Glu Asp Glu Arg Ile Val Leu Val Asp Asn Lys Cys
        275                 280                 285
Lys Cys Ala Arg Ile Thr Ser Arg Ile Ile Arg Ser Ser Glu Asp Pro
    290                 295                 300
Asn Glu Asp Ile Val Glu Arg Asn Ile Arg Ile Ile Val Pro Leu Asn
305                 310                 315                 320
Asn Arg Glu Asn Ile Ser Asp Pro Thr Ser Pro Leu Arg Thr Arg Phe
                325                 330                 335
Val Tyr His Leu Ser Asp Leu Cys Lys Lys Cys Asp Pro Thr Glu Val
            340                 345                 350
Glu Leu Asp Asn Gln Ile Val Thr Ala Thr Gln Ser Asn Ile Cys Asp
        355                 360                 365
```

```
Glu Asp Ser Ala Thr Glu Thr Cys Tyr Thr Tyr Asp Arg Asn Lys Cys
    370                 375                 380

Tyr Thr Ala Val Val Pro Leu Val Tyr Gly Gly Glu Thr Lys Met Val
385                 390                 395                 400

Glu Thr Ala Leu Thr Pro Asp Ala Cys Tyr Pro Asp
                405                 410

<210> SEQ ID NO 51
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
                20                  25                  30

Asn Lys Cys Lys Cys Ala Arg Ile Thr Ser Arg Ile Ile Arg Ser Ser
            35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp Gly
145                 150                 155                 160

Gly Gly Gly Ser Gly Gly Gly Gly Ser Gly Gly Gly Gly Ser Gln Val
                165                 170                 175

Gln Leu Val Gln Ser Gly Ala Glu Val Lys Lys Pro Gly Ala Ser Val
            180                 185                 190

Lys Val Ser Cys Lys Ala Ser Gly Tyr Thr Phe Ile Ser Tyr Thr Met
        195                 200                 205

His Trp Val Arg Gln Ala Pro Gly Gln Gly Leu Glu Trp Met Gly Tyr
    210                 215                 220

Ile Asn Pro Arg Ser Gly Tyr Thr His Tyr Asn Gln Lys Leu Lys Asp
225                 230                 235                 240

Lys Ala Thr Leu Thr Ala Asp Lys Ser Ala Ser Thr Ala Tyr Met Glu
                245                 250                 255

Leu Ser Ser Leu Arg Ser Glu Asp Thr Ala Val Tyr Tyr Cys Ala Arg
            260                 265                 270

Ser Ala Tyr Tyr Asp Tyr Asp Gly Phe Ala Tyr Trp Gly Gln Gly Thr
        275                 280                 285

Leu Val Thr Val Ser Ser Gly Gly Gly Ser Gly Gly Gly Gly Ser
    290                 295                 300

Gly Gly Gly Gly Ser Asp Ile Gln Met Thr Gln Ser Pro Ser Ser Leu
```

```
            305                 310                 315                 320
        Ser Ala Ser Val Gly Asp Arg Val Thr Ile Thr Cys Ser Ala Ser Ser
                        325                 330                 335

Ser Val Ser Tyr Met Asn Trp Tyr Gln Gln Lys Pro Gly Lys Ala Pro
                        340                 345                 350

Lys Arg Leu Ile Tyr Asp Thr Ser Lys Leu Ala Ser Gly Val Pro Ser
                        355                 360                 365

Arg Phe Ser Gly Ser Gly Ser Gly Thr Asp Phe Thr Leu Thr Ile Ser
                        370                 375                 380

Ser Leu Gln Pro Glu Asp Phe Ala Thr Tyr Tyr Cys Gln Gln Trp Ser
        385                 390                 395                 400

Ser Asn Pro Pro Thr Phe Gly Gly Gly Thr Lys Leu Glu Ile Lys
                        405                 410                 415

<210> SEQ ID NO 52
<211> LENGTH: 293
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Met Gly Trp Ser Tyr Ile Ile Leu Phe Leu Val Ala Thr Ala Thr Gly
        1               5                   10                  15

Val His Ser Glu Val Gln Leu Val Glu Ser Gly Gly Glu Leu Val Gln
                        20                  25                  30

Ala Gly Gly Ser Leu Arg Leu Ser Cys Ala Ala Ser Gly Leu Thr Phe
                        35                  40                  45

Ser Ser Tyr Asn Met Gly Trp Phe Arg Arg Ala Pro Gly Lys Glu Arg
                        50                  55                  60

Glu Phe Val Ala Ser Ile Thr Trp Ser Gly Arg Asp Thr Phe Tyr Ala
        65                  70                  75                  80

Asp Ser Val Lys Gly Arg Phe Thr Ile Ser Arg Asp Asn Ala Lys Asn
                        85                  90                  95

Thr Val Tyr Leu Gln Met Ser Ser Leu Lys Pro Glu Asp Thr Ala Val
                        100                 105                 110

Tyr Tyr Cys Ala Ala Asn Pro Trp Pro Val Ala Ala Pro Arg Ser Gly
                        115                 120                 125

Thr Tyr Trp Gly Gln Gly Thr Gln Val Thr Val Ser Ser Gly Gly Gly
                        130                 135                 140

Gly Ser Gly Gly Gly Gly Ser Gly Gly Gly Gly Ser Gln Glu Asp Glu
        145                 150                 155                 160

Arg Ile Val Leu Val Asp Asn Lys Cys Lys Cys Ala Arg Ile Thr Ser
                        165                 170                 175

Arg Ile Ile Arg Ser Ser Glu Asp Pro Asn Glu Asp Ile Val Glu Arg
                        180                 185                 190

Asn Ile Arg Ile Ile Val Pro Leu Asn Asn Arg Glu Asn Ile Ser Asp
                        195                 200                 205

Pro Thr Ser Pro Leu Arg Thr Arg Phe Val Tyr His Leu Ser Asp Leu
                        210                 215                 220

Cys Lys Lys Cys Asp Pro Thr Glu Val Glu Leu Asp Asn Gln Ile Val
        225                 230                 235                 240

Thr Ala Thr Gln Ser Asn Ile Cys Asp Glu Asp Ser Ala Thr Glu Thr
                        245                 250                 255
```

```
Cys Tyr Thr Tyr Asp Arg Asn Lys Cys Tyr Thr Ala Val Val Pro Leu
            260                 265                 270

Val Tyr Gly Gly Glu Thr Lys Met Val Glu Thr Ala Leu Thr Pro Asp
        275                 280                 285

Ala Cys Tyr Pro Asp
    290
```

<210> SEQ ID NO 53
<211> LENGTH: 137
<212> TYPE: PRT
<213> ORGANISM: Gorilla gorilla

<400> SEQUENCE: 53

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Lys Thr Ala
        115                 120                 125

Leu Thr Pro Asp Ala Cys Tyr Pro Asp
    130                 135
```

<210> SEQ ID NO 54
<211> LENGTH: 137
<212> TYPE: PRT
<213> ORGANISM: Nomascus leucogenys

<400> SEQUENCE: 54

```
Gln Glu Asp Glu Arg Ile Val Leu Val Asp Asn Lys Cys Lys Cys Ala
1               5                   10                  15

Arg Ile Thr Ser Arg Ile Ile His Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Ile Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Leu Tyr Gly Gly Glu Thr Lys Met Val Glu Thr Ala
        115                 120                 125

Leu Thr Pro Asp Ala Cys Tyr Pro Asp
    130                 135
```

<210> SEQ ID NO 55
<211> LENGTH: 417
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Lys
225                 230                 235                 240

Gly Gly Gly Gly Ser Gly Gly Gly Ser Gly Gly Gly Gly Ser Gln
                245                 250                 255

Glu Asp Glu Arg Ile Val Leu Val Asp Asn Lys Cys Lys Cys Ala Arg
            260                 265                 270

Ile Thr Ser Arg Ile Ile Arg Ser Ser Glu Asp Pro Asn Glu Asp Ile
        275                 280                 285

Val Glu Arg Asn Ile Arg Ile Ile Val Pro Leu Asn Asn Arg Glu Asn
    290                 295                 300

Ile Ser Asp Pro Thr Ser Pro Leu Arg Thr Arg Phe Val Tyr His Leu
305                 310                 315                 320

Ser Asp Leu Cys Lys Lys Cys Asp Pro Thr Glu Val Glu Leu Asp Asn
                325                 330                 335

Gln Ile Val Thr Ala Thr Gln Ser Asn Ile Cys Asp Glu Asp Ser Ala
            340                 345                 350

Thr Glu Thr Cys Tyr Thr Tyr Asp Arg Asn Lys Cys Tyr Thr Ala Val
            355                 360                 365

Val Pro Leu Val Tyr Gly Gly Glu Thr Lys Met Val Glu Thr Ala Leu
    370                 375                 380

Thr Pro Asp Ala Cys Tyr Pro Asp Gly Gly Ser Glu Gln Lys Leu
385                 390                 395                 400

Ile Ser Glu Glu Asp Leu Asn Ser Ala Val Asp His His His His
                405                 410                 415

His

<210> SEQ ID NO 56
<211> LENGTH: 413
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp Gly Gly Gly Ser Gly Gly
    130                 135                 140

Gly Gly Ser Gly Gly Gly Ser Gln Val Gln Leu Gln Gln Ser Gly
145                 150                 155                 160

Ala Glu Leu Ala Arg Pro Gly Ala Ser Val Lys Met Ser Cys Lys Ala
            165                 170                 175

Ser Gly Tyr Thr Phe Thr Arg Tyr Thr Met His Trp Val Lys Gln Arg
        180                 185                 190

Pro Gly Gln Gly Leu Glu Trp Ile Gly Tyr Ile Asn Pro Ser Arg Gly
    195                 200                 205

Tyr Thr Asn Tyr Asn Gln Lys Phe Lys Asp Lys Ala Thr Leu Thr Thr
    210                 215                 220

Asp Lys Ser Ser Ser Thr Ala Tyr Met Gln Leu Ser Ser Leu Thr Ser
225                 230                 235                 240

Glu Asp Ser Ala Val Tyr Tyr Cys Ala Arg Tyr Tyr Asp Asp His Tyr
                245                 250                 255

Ser Leu Asp Tyr Trp Gly Gln Gly Thr Thr Leu Thr Val Ser Ser Gly
            260                 265                 270

Gly Gly Gly Ser Gly Gly Gly Gly Ser Gly Gly Gly Gly Ser Gln Ile
        275                 280                 285

```
Val Leu Thr Gln Ser Pro Ala Ile Met Ser Ala Ser Pro Gly Glu Lys
        290                 295                 300

Val Thr Met Thr Cys Ser Ala Ser Ser Val Ser Tyr Met Asn Trp
305                 310                 315                 320

Tyr Gln Gln Lys Ser Gly Thr Ser Pro Lys Arg Trp Ile Tyr Asp Thr
                325                 330                 335

Ser Lys Leu Ala Ser Gly Val Pro Ala His Phe Arg Gly Ser Gly Ser
                340                 345                 350

Gly Thr Ser Tyr Ser Leu Thr Ile Ser Gly Met Glu Ala Glu Asp Ala
            355                 360                 365

Ala Thr Tyr Tyr Cys Gln Gln Trp Ser Ser Asn Pro Phe Thr Phe Gly
        370                 375                 380

Ser Gly Thr Lys Leu Glu Ile Lys Glu Gln Lys Leu Ile Ser Glu Glu
385                 390                 395                 400

Asp Leu Asn Ser Ala Val Asp His His His His His His
                405                 410

<210> SEQ ID NO 57
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6His tag"

<400> SEQUENCE: 57

His His His His His His
1               5
```

MODIFIED J-CHAIN

CROSS REFERENCE TO RELATED APPLICATIONS

This application is a continuation of U.S. patent application Ser. No. 16/136,049 filed Sep. 18, 2019 which is a continuation of U.S. patent application Ser. No. 15/301,366, filed on Sep. 30, 2016, now U.S. Pat. No. 10,400,038, which is a U.S. National Stage entry of PCT Patent Application No. PCT/US2015/024149, filed on Apr. 2, 2015, which claims priority benefit of the filing date of U.S. Provisional Application No. 61/974,738, filed on Apr. 3, 2014, the disclosures of which applications are incorporated herein by reference in their entireties. This application is related to U.S. patent application Ser. No. 15/452,616, filed on Mar. 7, 2017, now U.S. Pat. No. 9,951,134, which is also a continuation of U.S. patent application Ser. No. 15/301,366.

REFERENCE TO SEQUENCE LISTING SUBMITTED ELECTRONICALLY

The content of the electronically submitted sequence listing in ASCII text file (Name 015US4-Sequence-Listing; Size: 98,304 bytes; and Date of Creation: Sep. 8, 2018) filed with the application is incorporated herein by reference in its entirety.

BACKGROUND

Field of the Invention

The present invention concerns modified recombinant J-chain polypeptides and binding molecules, such as antibodies comprising the same.

Background

J-chain is an acidic 15-kDa polypeptide, which is associated with pentameric IgM and dimeric IgA via disulfide bonds involving the penultimate cysteine residue in the 18-amino acid secretory tail-piece (tp) at the C-terminus of the IgM μ or IgA α heavy chain. The three disulfide bridges are formed between Cys 12 and 100, Cys 71 and 91, and Cys 108 and 133, respectively. See, e.g. Frutiger et al. 1992, *Biochemistry* 31, 12643-12647. Structural requirements for incorporation of the J-chain into human IgM and IgA and for polymeric immunoglobulin assembly and association with the J-chain are reported by Sorensen et al. 2000, *Int. Immunol.* 12(1): 19-27 and Yoo et al. 1999, 1 *Biol. Chem.* 274(47):33771-33777, respectively. Recombinant production of soluble J-chain in *E coli* is reported by Redwan et al. 2006, *Human Antibodies* 15:95-102.

Methods for making hybrid IgA/IgG and IgM/IgG antibodies are known in the art. Thus, recombinant production of hybrid IgA2/IgG1 antibodies is reported in Chintalacharuvu et al. 2001, *Clin Immunol* 101(1):21-31. It has been reported that addition of αtp or μtp at the end of IgG γ heavy chain facilitates polymerization and enhances effector function such as complement activation (Smith et al., *J Immunol* 1995, 154:2226-2236). The IgA/IgG hybrid antibodies possess properties of both IgA and IgG.

Despite the advances made in the design of antibodies, there remains a need for modified antibodies with improved properties, such as improved affinity, specificity and/or avidity.

As the field has progressed, antibody function has been enhanced through creative means of protein engineering, such as to provide higher affinity, longer half-life, and/or better tissue distribution, as well as combination of small and large molecule technologies for increased focus of cell destruction via toxic payload delivery (e.g. antibody-drug conjugates). Another approach to improving antibody function takes advantage of the bivalent binding of the immunoglobulin G (IgG) structure which allows one IgG molecule to bind two antigens. Indeed, in certain applications, there exists good potential for asymmetric antibodies to exert useful functions by simultaneously binding two different target antigens. To address this need, a variety of constructs have been produced to yield a single molecule that can bind two different antigens, allowing for functions never before seen in nature. An example of this bi-specific approach is "blinatumomab" (MT103 or AMG103) which binds the CD3 and CD19 receptors, on T- and B-cells, respectively. This tethering of a cytotoxic T-cell to a cancerous B-cell, allows for effective treatment of B-cell leukemia.

However, there remain significant technical difficulties in construction, expression and production of bispecific antibodies. Although bispecific antibodies are regarded as promising therapeutic agents due to their ability to simultaneously bind two different antigens, their utility is limited due to problems with stability and manufacturing complexity.

Various forms of protein engineering have been used to match heterologous heavy chains, plus appropriate pair-wise matching of heavy and light chains to efficiently yield a bi-specific IgG. In addition, various bispecific antibody formats, including quadromas, chemical heteroconjugates, recombinant constructs using selected heterodimerization domains and recombinant constructs of minimal size consisting of two minimal antigen-binding sites.

However, all of these efforts have been fraught with difficulty.

Thus, despite efforts directed toward the development of engineered, such as bispecific, antibodies, there remains a great need for developing more efficient platforms. This is particularly true in the case of therapeutic antibodies, where the design and production of new, modified, antibodies and antibody-like molecules with multiple specificities can shorten the timeline between discovery and clinical introduction of such therapeutics.

SUMMARY

The present invention is based, at least in part, on the recognition that the J-chain of an IgM or IgA antibody can be modified by introducing one or more binding moieties into a native J-chain sequence, and the modified J-chain can be introduced into IgM, IgA, IgG/IgM or IgG/IgA antibodies without compromising the functionality of the recipient antibody or the binding of the modified J-chain to its target. This allows the modified J-chain with binding moiety to interact with one set of target antigens, while the IgA, IgM, IgG/IgM or IgG/IgA antibody can react with a different set of target antigens.

The invention is further based on the recognition that by directing the modified J-chain to an effector cell, such as a T-cell, NK-cell, macrophage or neutrophil, the immune response of the body can be activated, and the antibody dependent cellular cytotoxicity (ADCC) response can be improved.

In one aspect, the present invention concerns a modified J-chain comprising an extraneous binding moiety introduced into a native sequence J-chain.

In one embodiment, the native sequence J-chain is the native human J-chain sequence of SEQ ID NO: 1, or a functional fragment thereof.

In another embodiment, the extraneous binding moiety is introduced into the native human J-chain sequence of SEQ ID NO: 1 by direct or indirect fusion.

In yet another embodiment, binding moiety is introduced by indirect fusion through a peptide linker.

In one embodiment, the indirect fusion is accomplished through a peptide linker at or around the C- and/or N-terminus of the binding moiety.

In another embodiment, the extraneous binding moiety is introduced into the native human J-chain sequence of SEQ ID NO: 1 at or around the C-terminus and/or the N-terminus, such as within about 10 residues from the C-terminus and/or the N-terminus.

In a further embodiment, the extraneous binding moiety is introduced into the native human J-chain sequence in between cysteine residues 92 and 101 of SEQ ID NO: 1.

In a still further embodiment, the extraneous binding moiety is introduced into the native human J-chain sequence of SEQ ID NO: 1 at or near a glycosylation site.

The peptide linker, if present, may, for example, be about 10 to 20 amino acids long, or about 15 to 20 amino acids long, or 15 amino acids long.

In a further embodiment, the extraneous binding moiety is introduced into the native human J-chain sequence of SEQ ID NO: 1 by chemical or chemo-enzymatic derivatization. The chemical linker may be a cleavable or a non-cleavable linker, where the cleavable linker may, for example, be a chemically labile linker or an enzyme-labile linker.

In a further embodiment, the linker is selected from the group consisting of N-succinimidyl-3-(2-pyridyldithio) propionate (SPDP), succinimidyl-4-(N-maleimidomethyl) cyclohexane-1-carboxylate (SMCC), N-succinimidyl-4-(2-pyridylthio) pentanoate (SPP), iminothiolane (IT), bifunctional derivatives of imidoesters, active esters, aldehydes, bis-azido compounds, bis-diazonium derivatives, diisocyanates, and bis-active fluorine compounds.

In a different embodiment, the J-chain is modified by insertion of an enzyme recognition site, and by post-translationally attaching an extraneous binding moiety at the enzyme recognition site through a peptide or non-peptide linker.

In all embodiments, the extraneous binding moiety may, for example, be selected from the group consisting of antibodies, antigen-binding fragments of antibodies, antibody-drug conjugates, antibody-like molecules, antigen-binding fragments of antibody-like molecules, soluble and membrane-bound proteins, ligands, receptors, virus-like particles, protein toxins, enzymes, and alternative scaffolds. Examples of alternative scaffolds include darpins, fibronectin domains, adnectins, and knottins. Typical antigen-binding fragments include F(ab')$_2$, F(ab)$_2$, Fab', Fab, Fv, scFv, and single domain antibodies. In a preferred embodiment, the antigen-binding fragment is scFv.

In one embodiment, the extraneous binding moiety of the modified J-chain binds to an effector cell, where the effector cell may, for example, be selected from the group consisting of T-cells, natural killer (NK) cells, macrophages and neutrophils.

In one embodiment, the effector cell is a T-cell, where the extraneous binding moiety may, for example, bind to CD3ε on the T-cell.

In another embodiment, the effector cell is an NK cell, where the target for the extraneous binding moiety of the modified J-chain may, for example be selected from the group consisting of CD16, CD64 and NKG2D on the NK cell.

In a yet another embodiment, the effector cell is a macrophage, where the extraneous binding moiety of the modified J-chain may, for example, bind to CD14 on the macrophage.

In a further embodiment, the effector cell is a neutrophil, where the extraneous binding moiety of the modified J-chain may, for example, bind to CD16b or CD177 on the neutrophil.

In another aspect, the invention concerns an antibody comprising a modified J-chain as hereinbefore described, or an antigen-binding fragment of such antibody. The antibody can be an IgM, IgA, IgG/IgM or IgG/IgA antibody, and includes multi-specific, e.g. bispecific antibodies.

In one embodiment, the antibody is an IgM antibody, an IgA antibody, or an IgG antibody comprising a tail piece, or an antigen-binding fragment thereof.

In another embodiment, the antibody has binding specificity to one or more binding target selected from the group consisting of target cells, soluble binding targets, cell surface receptors, matrix proteins, transporter receptors.

In yet another embodiment, the antibody binds to a tumor cell.

In a further embodiment, the antibody binds to a tumor target associated antigen listed in FIG. 19, where the J-chain may, for example, be modified to bind any of the effector cell targets listed in FIG. 19.

In a still further embodiments, the modified J-chain is present in the antibodies in a V-linker-J orientation or in a J-linker-V orientation.

In one embodiment, the tumor is a hematologic cancer or a solid tumor, where the hematologic cancer may, for example, be leukemia, lymphoma, myeloma, and myelodysplastic syndrome, specifically including acute myeloid leukemia, acute lymphoblastic leukemia, chronic myelogenous leukemia, or chronic lymphocytic leukemia, Hodgkin's lymphoma and non-Hodgkin's lymphoma. In such embodiments, the antibody may, for example, bind to one or more of CDIM, CD19, CD20, CD22, CD33, CD70, CD56, CD138, and the modified J-chain may bind to CD3c.

In another embodiment, the tumor is an epithelial tumor.

In yet another embodiment, the antibody binds to a carbohydrate-based target on the tumor.

In a further embodiment, the antibody binds to a viral antigen, such as an HBV antigen or an HIV antigen, e.g. PreS1 or GP120.

In a further aspect, the invention concerns a composition comprising the IgM, IgA, IgG/IgM, IgG/IgA antibodies comprising a modified J-chain, as described. The composition may, for example, be a pharmaceutical composition or a diagnostic composition.

In a still further aspect, the invention concerns a method of treating a tumor or viral disease comprising administering to a subject in need an effective amount of an IgM, IgA, IgG/IgM, IgG/IgA antibody with a modified J-chain, as described herein.

In another aspect, the invention concerns the use of an IgM, IgA, IgG/IgM, IgG/IgA antibody with a modified J-chain, as described herein in the preparation of a medicament for the treatment of a tumor or viral disease.

In yet another aspect, the invention concerns the use of an IgM, IgA, IgG/IgM, IgG/IgA antibody with a modified J-chain, as described herein in the treatment of a tumor or viral disease.

BRIEF DESCRIPTION OF THE DRAWINGS/FIGURES

FIG. 3 shows the amino acid sequence of mature human J-chain (SEQ ID NO: 1).

FIG. 4 shows the alignment of mature human J-chain (SEQ ID NO: 1) and J-chains from various animal species (SEQ ID Nos: 1 to 44).

| Abbreviation | Citation |
|---|---|
| Hum | Human NP_653247 23-159 (SEQ ID NO: 1) |
| Chm | Chimpanzee XP_001160135 39-175 (SEQ ID NO: 2) |
| Gor | Gorilla XP_004038830 23-159 (SEQ ID NO: 53) |
| Ora | Orangutan NP_001125381 23-159 (SEQ ID NO: 4) |
| Gib | Gibbon XP_003265761 39-175 (SEQ ID NO: 54) |
| Mar | Marmoset XP_003732538 32-168 (SEQ ID NO: 6) |
| Cyn | Cynomolgus Monkey NP_001247815 23-159 (SEQ ID NO: 7) |
| Bab | Baboon XP_003898844 23-159 (SEQ ID NO: 8) |
| Squ | Squirrel Monkey XP_003931978 23-159 (SEQ ID NO: 9) |
| Shr | Tree Shrew XP_006142955 25-160 (SEQ ID NO: 10) |
| Dol | Dolphin XP_004328961 25-158 (SEQ ID NO: 11) |
| Kil | Killer Whale XP_004283629 25-158 (SEQ ID NO: 12) |
| Ele | Elephant XP_003414110 25-158 (SEQ ID NO: 13) |
| Sea | Seal XP_006729388 25-158 (SEQ ID NO: 14) |
| Rhi | Rhinoceros XP_004419202 25-157 (SEQ ID NO: 15) |
| Cat | House Cat XP_003985350 25-158 (SEQ ID NO: 16) |
| Wol | Wolf XP_532398 26-159 (SEQ ID NO: 17) |
| Pan | Giant Panda EFB23253 1-134 (SEQ ID NO: 18) |
| Fer | Ferret XP_004766376 26-158 (SEQ ID NO: 19) |
| Hor | Horse NP_001271464 25-158 (SEQ ID NO: 20) |
| Gui | Guinea Pig NP_001265705 25-160 (SEQ ID NO: 21) |
| Cam | Camel XP_006188738 25-158 (SEQ ID NO: 22) |
| Goa | Goat XP_005681786 25-158 (SEQ ID NO: 23) |
| Chn | Chinchilla XP_005392838 94-229 (SEQ ID NO: 24) |
| Ham | Hamster XP_005068228 24-160 (SEQ ID NO: 25) |
| She | Sheep XP_004009937 25-158 (SEQ ID NO: 26) |
| BBa | Brown Bat XP_006094475 25-158 (SEQ ID NO: 27) |
| Ant | Antelope XP_005983836 25-158(SEQ ID NO: 28) |
| Cow | Cow NP_786967 25-157 (SEQ ID NO: 29) |
| Mou | Mouse NP_690052 23-159 (SEQ ID NO: 30) |
| Rat | Rat EDL88516 23-159 (SEQ ID NO: 31) |
| Hed | Hedgehog XP_004703237 25-157 (SEQ ID NO: 32) |
| Rab | Rabbit P23108 1-136 (SEQ ID NO: 33) |
| Opo | Opossum XP_003341415 29-162 (SEQ ID NO: 34) |
| All | Alligator XP_006270094 26-159 (SEQ ID NO: 35) |
| Tur | Turtle XP_005304167 26-159 (SEQ ID NO: 36) |
| Tas | Tasmania Devil XP_003772863 27-160 (SEQ ID NO: 37) |
| Pla | Platypus XP_003430954 36-160 (SEQ ID NO: 38) |
| Par | Parakeet XP_005142787 28-160 (SEQ ID NO: 39) |
| Duc | Duck XP_005031370 28-160 (SEQ ID NO: 40) |
| Chi | Chicken NP_989594 26-158 (SEQ ID NO: 41) |
| Tur | Turkey XP_003205717 27-159 (SEQ ID NO: 42) |
| Fal | Falcon XP_005243236 29-160 (SEQ ID NO: 43) |
| Spa | Sparrow XP_005492217 29-158 (SEQ ID NO: 44) |

FIG. 5 shows the alignment of the amino acid sequence of human and bat (back *Pteropus alecto*) J-chain amino acid sequences (SEQ ID NOs: 1 and 45, respectively).

Figure 6:
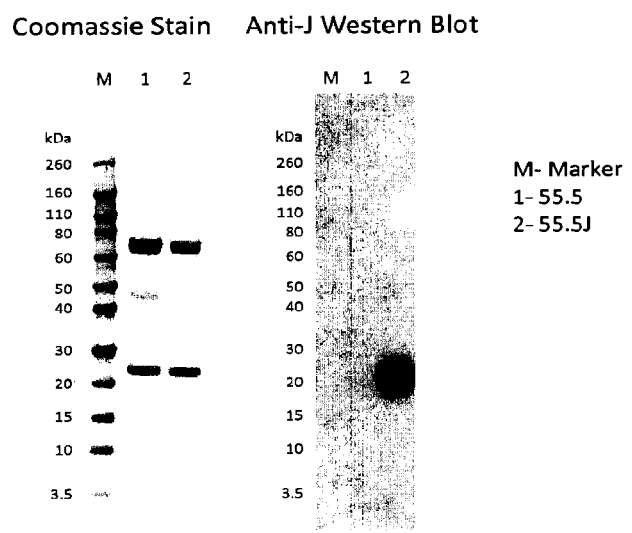

FIG. 6: An IgM antibody lacking its J-chain (negative control) and IgM comprising a J-chain were separated on reducing SDS PAGE and detected by Western Blot using an anti-J-chain antibody. The anti-J-chain antibody only reacted with the IgM comprising a J-chain.

Figure 7:
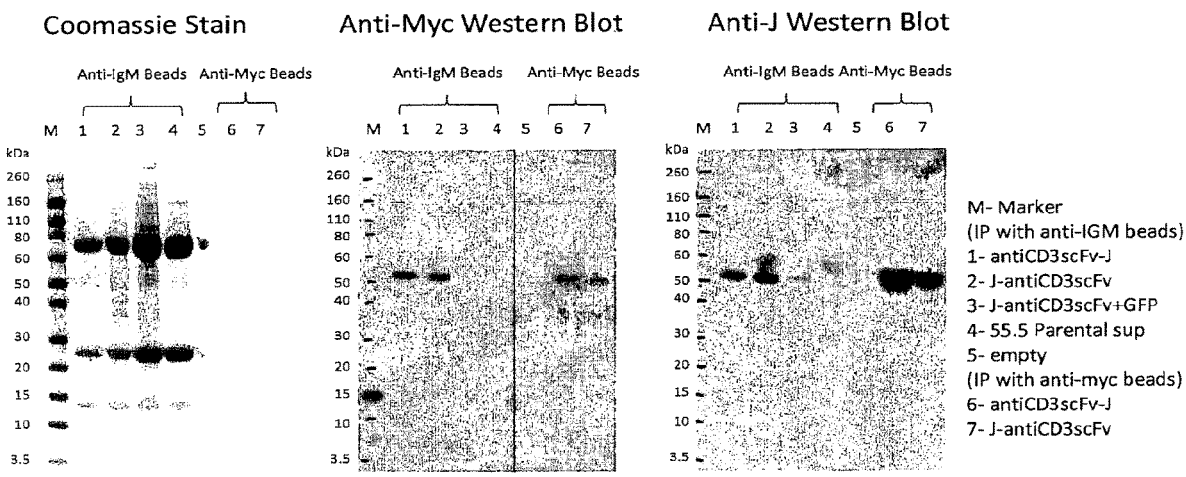

FIG. 7: Harvested supernatant from transfected CHO cells were divided equally for immunoprecipitation with either anti-mu or anti-myc affinity matrix. These CHO cells were expressing an IgM with anti-B cells specificity known as CDIM (for cell death inducing molecule). This IgM antibody is known as IGM-55.5. The immunoprecipitated proteins were separated on reducing SDS PAGE and detected by Western Blot by anti-J or anti-myc antibodies. Both N-terminal tagged anti-CD3scFvJ and C-terminal tagged J-antiCD3scFv transfected cells displayed a positive band around 51 kD, which reacted to both anti-J and anti-myc antibodies.

FIG. 8 illustrates two different orientations of a bis-specific IgM pentamer comprising a modified J-chain with binding specificity for a T-cell (the T-cell antigen CD3).

FIG. 9: Sequence (SEQ ID NO: 46) and structure of an anti-CD3 single-chain Fv comprising a J-chain at the C-terminus (antiCD3scFv-J). SP=signal peptide.

FIG. 10: Sequence (SEQ ID NO: 47) and structure an anti-CD3 single-chain Fv comprising a J-chain at the N-terminus (J-antiCD3scFv). SP=signal peptide.

Figure 11:
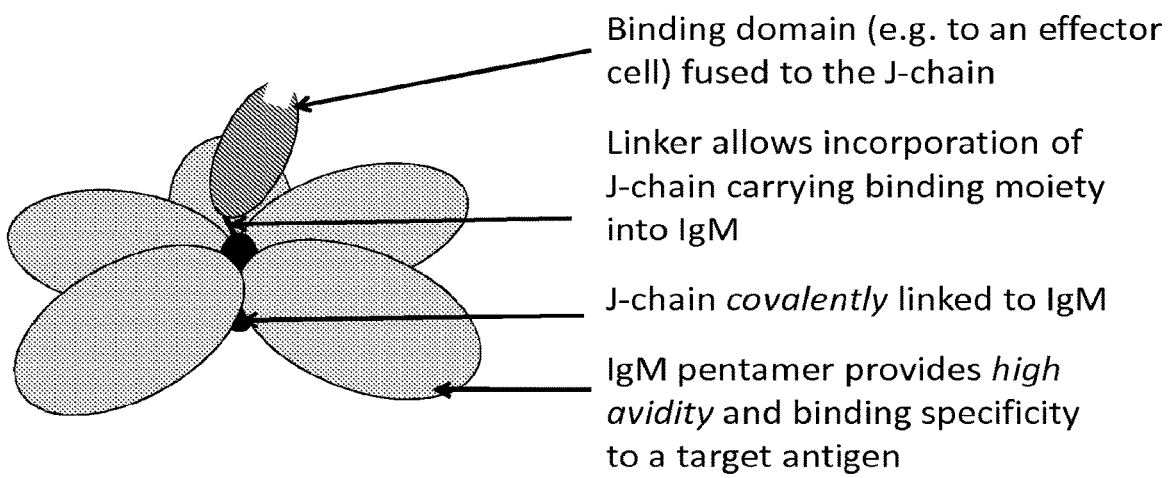

FIG. 11 is a schematic illustration of an asymmetric bi-specific IgM pentamer with binding-specificity for a target antigen, comprising a binding domain covalently attached to the J-chain with binding specificity for an effector cell.

Figure 12:
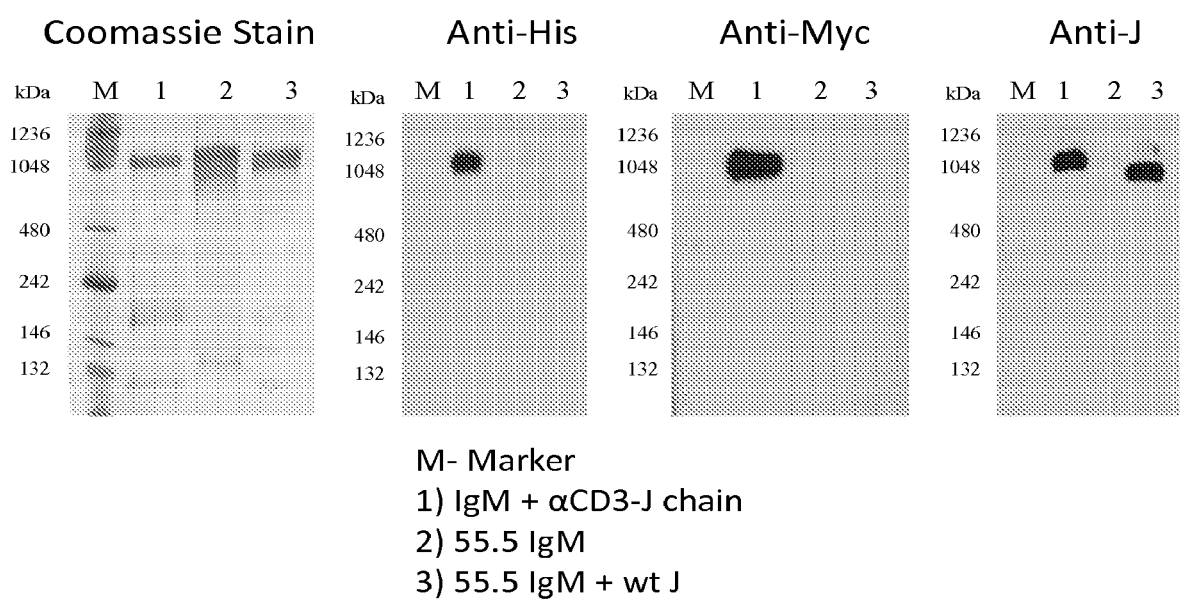

FIG. 12 shows Western blots of an anti-CD20 IgM pentamer with a J-chain covalently modified with an CD3 scFv binding domain. Non-reducing PAGE stained with Coomassie Blue observes the full size of IgM: approximately 1 million Daltons MW. The modified J-chain incorporates into the IgM pentamers in both orientations: CD3-J and J-CD3.

Figure 13:
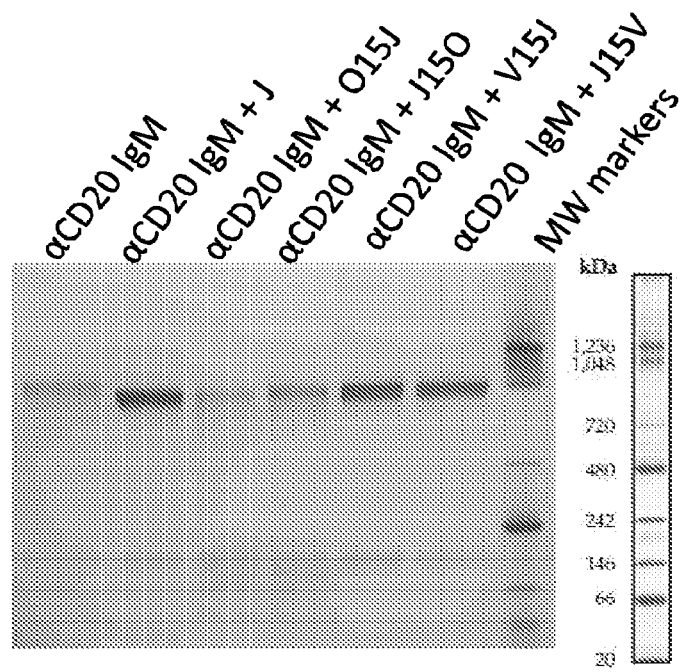

FIG. 13 shows the results of transient co-transfections of the heavy chain (HC), light chain (LC), and modified J-chain of a bispecific anti-CD20 IgM ($CD20_{IgM}$) with a modified J-chain providing binding specificity to CD3 ($CD3_J$).

FIG. 14 shows that incorporation of a modified J-chain into an anti-CD20 IgM has no negative effect on CDC activity. In addition, the data show that an IgM molecule comprising a modified J-chain in either orientation (V15J or J15V, where "15" designates the length of the linker) is significantly more potent than an anti-CD20 IgG antibody.

Figure 15:
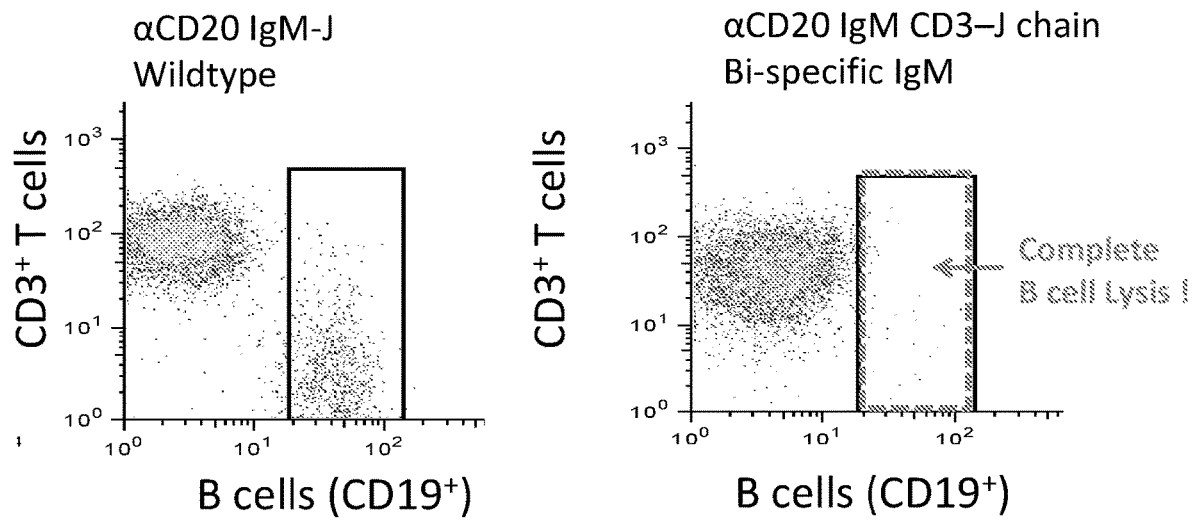

FIG. 15 shows that a bispecific $CD20_{IgM} \times CD3_{J-chain}$ molecule is highly potent at B-cell depletion as a result of active T-cell killing of B-cells due to the CD3-specificity of the modified J-chain. Raji, a CD19+CD20+ B cell line, was co-cultured with T-ALL, a CD8+ Cytolytic T cell line) with CD20 IgM×J-wild-type or CD20 IgM×CD3-J chain for 24 hours at 37 degrees, 5% CO2. Cell were harvested and stained with fluorescent antibodies to CD3 and CD19 and analyzed by flow cytometry to assess viable B cells.

Figure 16:
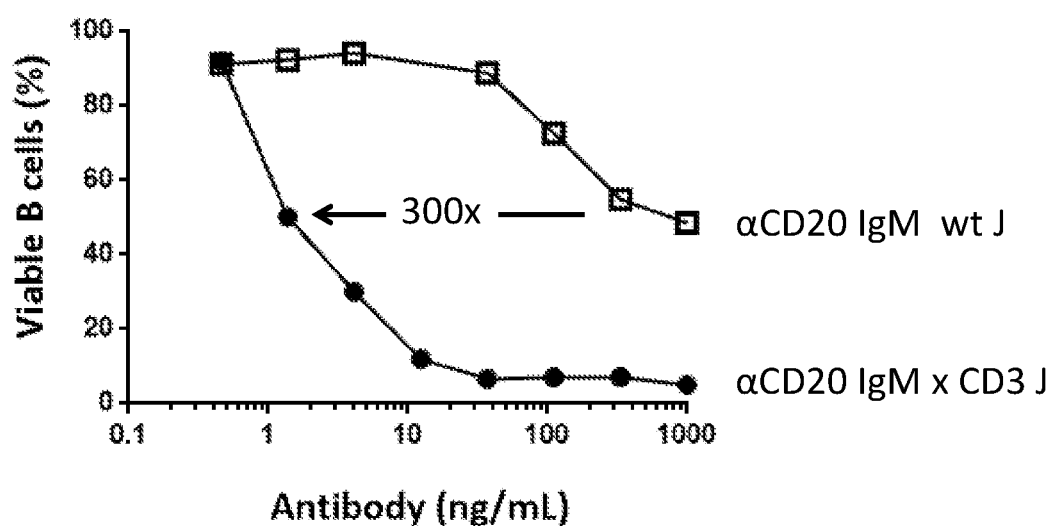

FIG. 16 shows that a bispecific anti-CD20 IgM molecule with a modified J-chain providing binding specificity to CD3 has significantly improved cytotoxic activity over an anti-CD20 IgM pentamer with wild-type J-chain. The T-cell engaging bispecific IgM pentamer is effective at a concentration of 1 ng/ml and is 300-times more potent compared to anti-CD20 IgM with wild-type J-chain.

Figure 17:
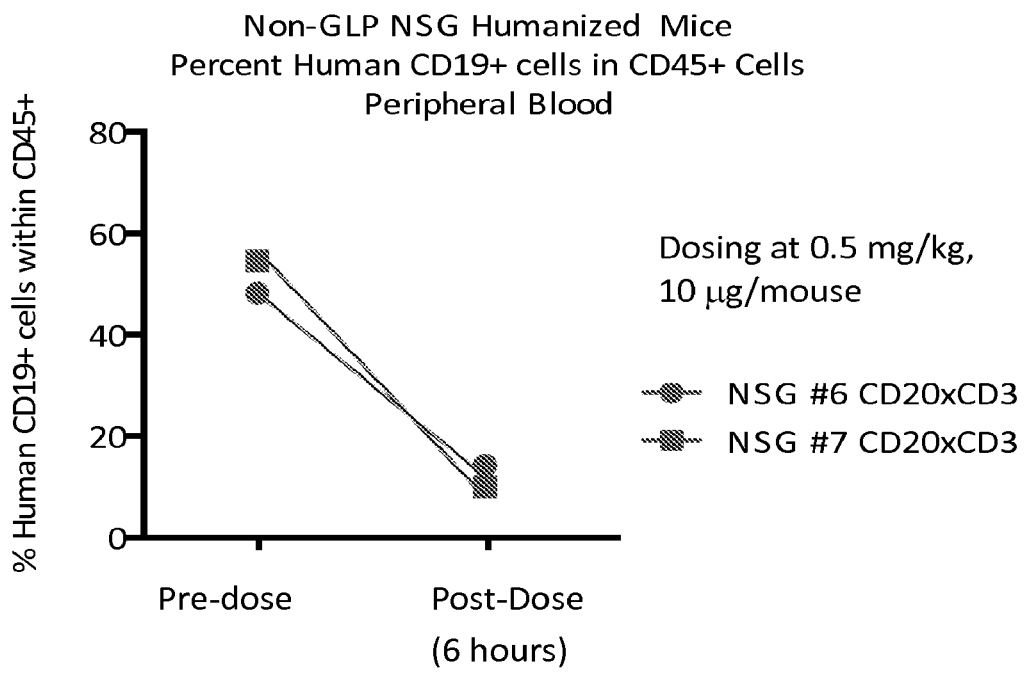

FIG. 17 shows in vivo B-cell depletion with anti-CD20 IgG, IgM and bispecific IgM. Humanized NSG mice reconstituted with human CD34+ stem cells (Jackson Laboratory; Stock Number: 007799) were purchased and whole blood was analyzed for pre-dose levels of CD19+ B cells. CD20 IgM x CD3-J chain was prepared for intravenous dosing animals at 0.5 mg/kg. Following 6 hours after dosing, whole blood was obtained from animals and analyzed by flow cytometry for circulating levels of human B cells using a fluorescently labeled CD19+ antibody.

Figure 18:
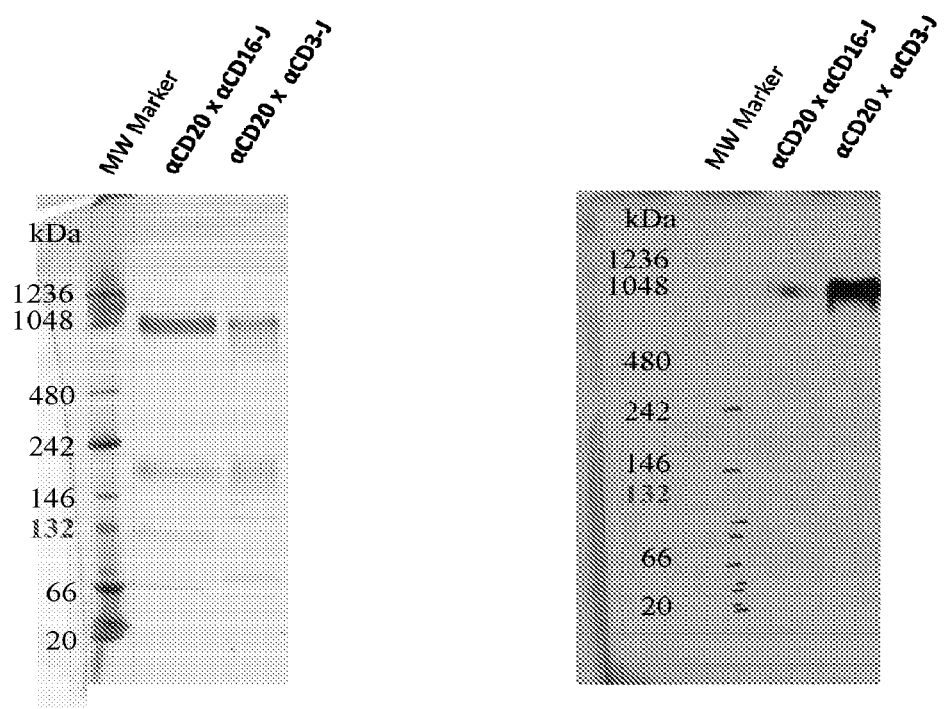

FIG. 18 is a Western blot of a CD16 specific Vhh camelid-J-chain.

FIG. 19 lists IgM antibody targets and effector cell targets for a modified J-chain. Any of the IgM antibody targets listed in the left column of the table can be combined with any of the modified J-chain targets listed in the right column.

DETAILED DESCRIPTION

Definitions

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

All publications mentioned herein are expressly incorporated herein by reference to disclose and describe the methods and/or materials in connection with which the publications are cited.

The term "antibody" includes monoclonal antibodies (including full length antibodies which have an immunoglobulin Fc region), single-chain molecules, as well as antibody fragments (e.g., Fab, F(ab')2, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. Unless noted otherwise, the term "antibody" is used herein in the broadest sense and specifically includes all isotypes, sub-classes and forms of antibodies, including IgG, IgM, IgA, IgD, and IgE antibodies and their fragments, preferably antigen-binding fragments. Preferred antibodies herein include IgM and IgA antibodies and their antigen-binding fragments, which may be modified to include sequences from other isotypes, such as IgG to produce chimeric antibodies.

In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site.

Figure 1:
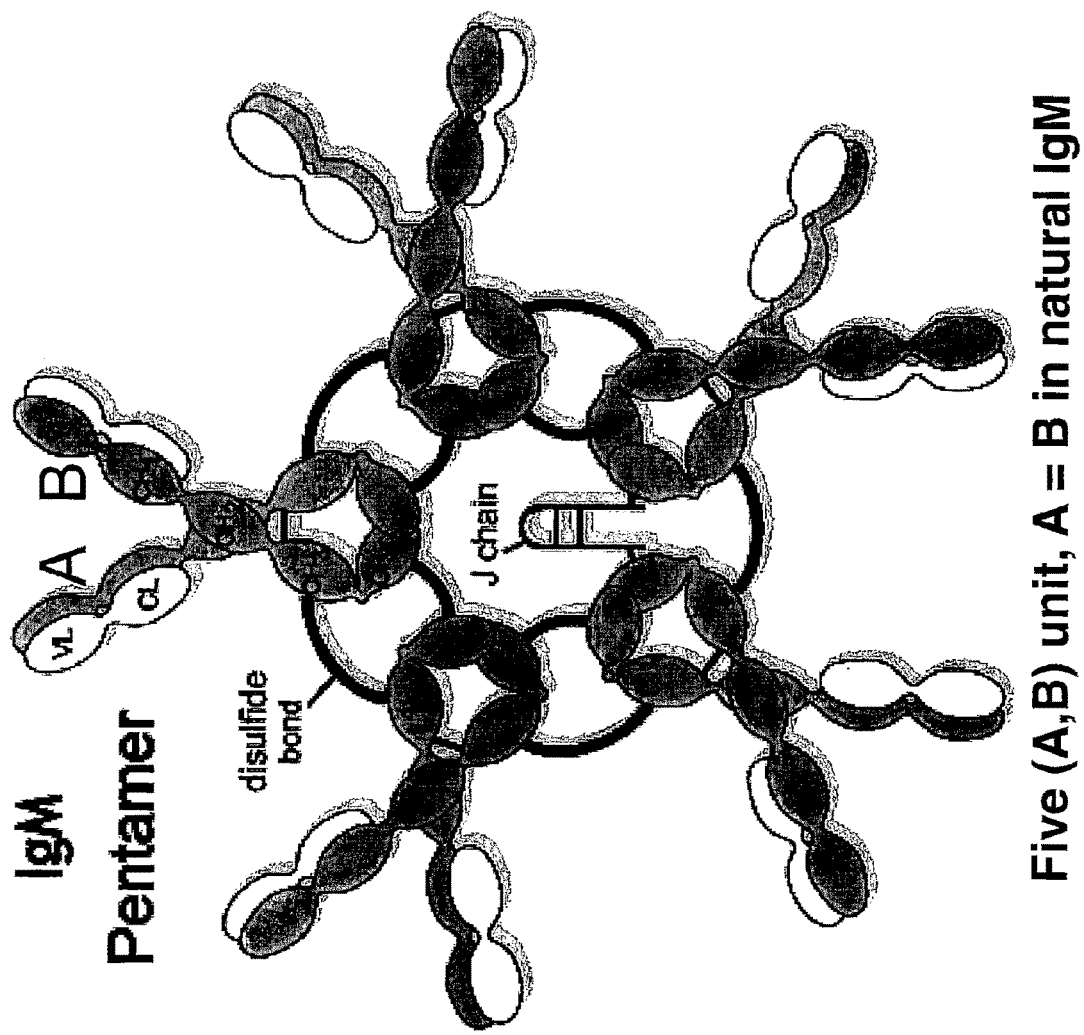
FIG. 1 illustrates the structure of an IgM pentamer, comprising a J-chain, wherein chains A and B are identical in native IgM.

IgM is a glycoprotein which forms polymers where multiple immunoglobulins are covalently linked together with disulfide bonds. IgM mostly exists as a pentamer but also as a hexamer and therefore contains 10 or 12 antigen binding sites. The pentameric form typically contains an additional polypeptide, called the J-chain, but can also be made in the absence of J-chain. The pentameric IgM molecule has a molecular weight of approximately 970 kDa. Due to its polymeric nature, IgM possesses high avidity and is particularly effective in complement activation. Unlike in IgG, the heavy chain in IgM monomers is composed of one variable and four constant domains. The IgM constant domains are designated herein as CM1 or $C\mu1$, CM2 or $C\mu2$, CM3 or $C\mu3$, and CM4 or $C\mu4$, wherein the "CM" and "Cμ" designations are used interchangeably. The structure of an IgM pentamer is illustrated in FIG. 1.

The term "IgM" is used herein in the broadest sense and specifically includes mono-, and multi-specific (including bispecific) IgM molecules, such as, for example, the multi-specific IgM binding molecules disclosed in PCT Application No. PCT/US2014/054079, the entire disclosure of which is expressly incorporated by reference herein.

The term "IgM binding unit" or "IgM antibody binding unit" is used in the broadest sense and specifically covers an IgM antibody heavy chain constant region polypeptide, comprising at least a CM4 constant domain, fused to a variable domain sequence ($V_H$) binding to a target (e.g. antigen), with or without an associated antibody light chain variable domain ($V_L$) sequence.

The term "bispecific IgM binding unit" or "bispecific IgM antibody binding unit" is used in the broadest sense and specifically covers a pair of IgM antibody heavy chain constant region polypeptides, comprising at least a CM4 constant domain, fused to a variable domain sequence ($V_H$), each variable domain sequence binding to a different target, with or without associated antibody light chain variable domain ($V_L$) sequences. In one embodiment, the bispecific IgM antibody comprises two $V_H V_L$ antigen binding regions, each capable of binding to a different epitope on one antigen or epitopes on two different antigens. The bispecific IgM antibody binding units can be full length from a single species or be chimerized or humanized. The bispecific IgM antibodies of the present invention have a penta- or hexa-meric ring structure comprising five or six bispecific IgM binding units.

The term "multi-specific IgM" is used herein in the broadest sense to refer to IgM antibodies with two or more binding specificities. Thus, the term "multi-specific" includes "bispecific", e.g. bispecific antibodies or bispecific binding units, including IgM pentamers comprising at least two monospecific subunits, each binding to a different antigen (AA, BB), or five or six bispecific subunits, each binding to two different antigens (AB, AB). Thus, the bispecific and multi-specific IgM pentamers may include five identical bispecific binding units, monospecific IgM binding units, at least two of them have different binding specificities, or any combination thereof.

A "full length IgM antibody heavy chain" is a polypeptide consisting in N-terminal to C-terminal direction of an antibody heavy chain variable domain ($V_H$), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4). The bispecific full-length IgM antibodies as defined herein comprise five or six monomers (binding units), each with two antigen binding sites, which specifically bind to two different binding targets (epitopes). The C-terminus of the heavy or light chain of the full-length antibody denotes the last amino acid at the C-terminus of the heavy or light chain. The N-terminus of the heavy or light chain of the full-length antibody denotes the first amino acid at the N-terminus of the heavy or light chain.

Figure 2:
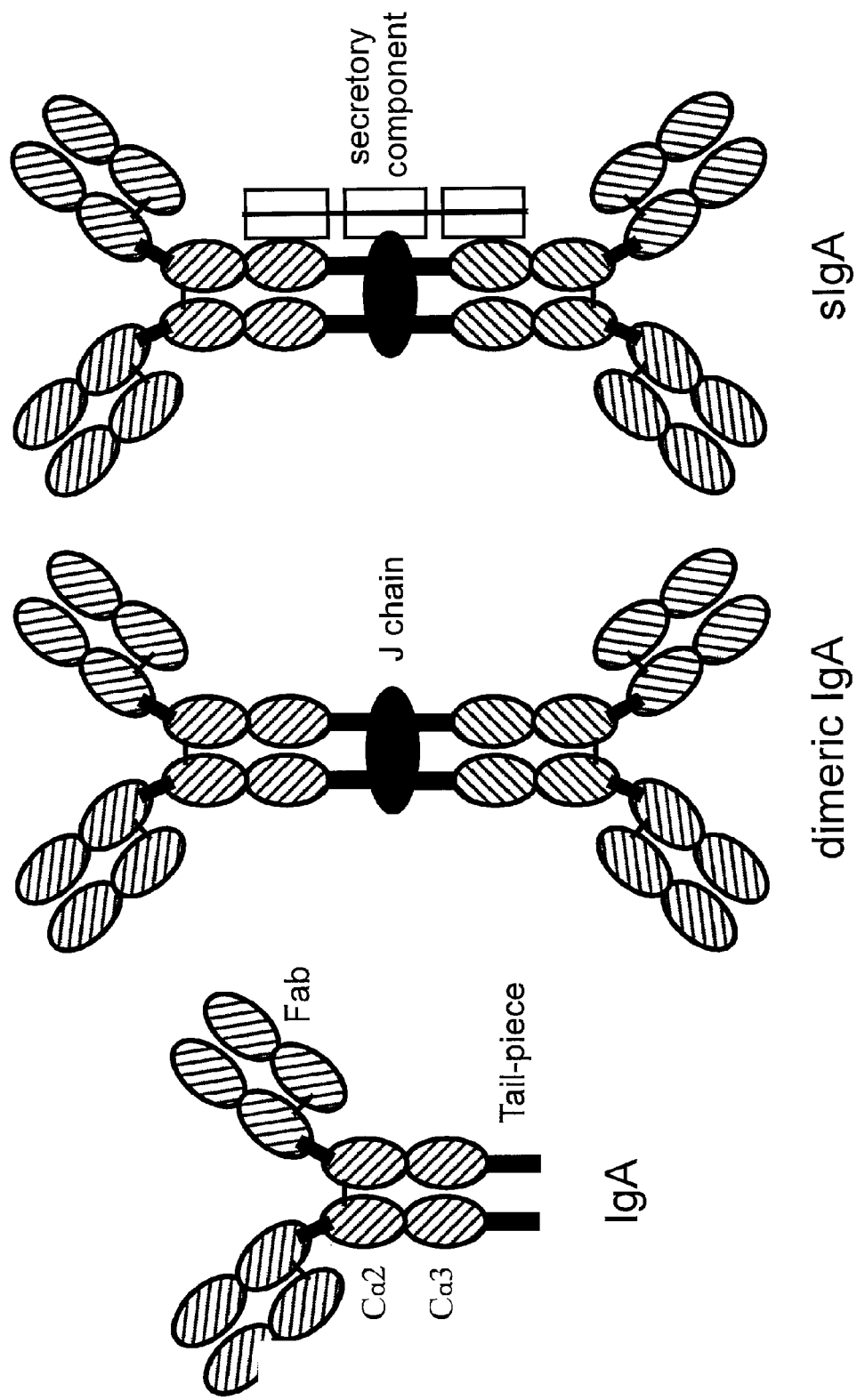
FIG. 2 shows the schematic structures of IgA, dimeric IgA, and secretory IgA (sIgA).

Native IgA is a tetrameric protein comprising two identical light chains (κ or λ) and two identical heavy chains (α). In the human, there are two IgA isotypes, IgA1 and IgA2. IgA, similarly to IgG, contains three constant domains (CA1-CA3 or Cα1-Cα3), with a hinge region between the Cα1 and Cα2 domains, wherein the "CA" and "Cα" designations are used interchangeably. All IgA isotypes have an 18 amino acid "tailpiece", which is located C-terminal to the Cα3 domain, which enables polymeric Ig formation (see, e.g. Garcia-Pardo et al., 1981, *J. Biol. Chem.* 256, 11734-11738 and Davis et al., 1988, *Eur. J. Immunol.* 18, 1001-1008). Serum IgA is a monomer but can also polymerize. In its secretory form IgA comprises from 2-5 of the basic 4-chain units, linked by a J-chain, which may include a tail-piece, and may be associated by a secretory component. The structures of tail-piece, dimeric IgA and secretory IgA, associated with a secretory component (sIgA) are illustrated in FIG. 2. IgA antibodies can be further divided into IgA1 and IgA2 sub-classes. The term "IgA" antibody is used herein to specifically include all sub-classes, i.e. IgA1 and IgA2 antibodies, including dimeric and multimeric forms, with and without a secretory component, as well as fragments, preferably antigen-binding fragments, of such antibodies. For the purposes of the present invention, the IgA antibody preferably is a dimer, where two tail-pieces are connected by a J-chain (see, FIG. 2).

The term "IgA" is used herein in the broadest sense and specifically includes mono-, and multi-specific IgA molecules, such as, for example, the multi-specific IgA binding molecules disclosed in PCT Application No. PCT/US2015/015268, the entire disclosure of which is expressly incorporated by reference herein.

The term "multi-specific IgA" is used herein in the broadest sense to refer to IgA antibodies with two or more binding specificities. Thus, the term "multi-specific" includes "bispecific", e.g. bispecific antibodies or bispecific binding units, including IgA dimers comprising two monospecific subunits, each binding to a different antigen (AA, BB), or two bispecific subunits, each binding to two different antigens (AB, AB).

In one embodiment, the dimeric multi-specific IgA molecules consist of two monospecific binding units, each binding unit having binding specificity to a different binding target (AA, BB). In another embodiment, in the dimeric IgA molecules at least one of the two binding units has two different binding specificities (i.e. is a bispecific, e.g. AA, A,B or AA, BC). In another embodiment, each of the two binding units has two specificities, which may be the same (AB, AB) or different (AC, CD or AB, AC, for example).

The term "bispecific IgA antibody binding unit" is used in the broadest sense and specifically covers a pair of IgA antibody heavy chain constant region polypeptides, comprising at least a CA3 constant domain, fused to a variable domain sequence ($V_H$), each variable domain sequence binding to a different target, with or without associated antibody light chain variable domain ($V_L$) sequences. In one embodiment, the bispecific IgA antibody comprises two $V_H V_L$ antigen binding regions, each capable of binding to a different epitope on one antigen or epitopes on two different antigens. The bispecific IgA antibody binding units can be full length from a single species or be chimerized or humanized.

A "full length IgA antibody heavy chain" is a polypeptide consisting in N-terminal to C-terminal direction of an antibody heavy chain variable domain (VH), an antibody constant heavy chain constant domain 1 (CA1 or Cα1), an antibody constant heavy chain constant domain 2 (CA2 or Cα2), and an antibody heavy chain constant domain 3 (CA3 or Cα3). The bi- or multi-specific full-length IgA antibodies according to the invention comprise two monomers (binding units), each of which may be mono- or bispecific, with or without a secretory component. Thus, the multi-specific IgA antibodies of the present invention may include monospecific and bispecific binding units, provided that the resultant IgA antibody has at least two binding specificities. The C-terminus of the heavy or light chain of the full-length antibody denotes the last amino acid at the C-terminus of the heavy or light chain. The N-terminus of the heavy or light chain of the full-length antibody denotes the first amino acid at the N-terminus of the heavy or light chain.

For further details of the structure and properties of the different classes of antibodies, see e.g., Basic and Clinical Immunology, 8th Edition, Daniel P. Stites, Abba I. Terr and Tristram G. Parslow (eds), Appleton & Lange, Norwalk, Conn., 1994, page 71 and Chapter 6.

The term "interface", as used herein, is used to refer to a region, which comprises those "contact" amino acid residues (or other non-amino acid groups such as, for example, carbohydrate groups,) in a first IgM heavy chain constant region which interact with one or more "contact" amino acid residues (or other non-amino acid groups) in a second IgM heavy chain constant region.

The term "asymmetric interface" is used to refer to an interface (as hereinabove defined) formed between two antibody chains, such as a first and a second IgM heavy chain constant region and/or between an IgM heavy chain constant region and its matching light chain, wherein the contact residues in the first and the second chains are different by design, comprising complementary contact residues. The asymmetric interface can be created by knobs/holes interactions and/or salt bridges coupling (charge swaps) and/or other techniques known in the art, such as for example, by the CrossMab approach for coupling a μ heavy chain to its matching light chain.

A "cavity" or "hole" refers to at least one amino acid side chain which is recessed from the interface of the second polypeptide and therefore accommodates a corresponding protuberance ("knob") on the adjacent interface of the first polypeptide. The cavity (hole) may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The preferred import residues for the formation of a cavity are usually naturally occurring amino acid residues and are preferably selected from alanine (A), serine (S), threonine (T), valine (V) and glycine (G). Most preferred amino acid residues are serine, alanine or threonine, most preferably alanine. In the preferred embodiment, the original residue for the formation of the protuberance has a large side chain volume, such as tyrosine (Y), arginine (R), phenylalanine (F) or tryptophan (W).

An "original" amino acid residue is one which is replaced by an "import" residue which can have a smaller or larger side chain volume than the original residue. The import amino acid residue can be a naturally occurring or non-naturally occurring amino acid residue, but preferably is the former.

By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The methods of the current invention, in certain embodiments, involve replacing at least one original amino acid residue in an IgM heavy chain, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art, including techniques of molecular modeling.

By "original nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g. a humanized monoclonal antibody).

Preferably the import amino acid residue for forming the protuberance has a relatively small number of "rotamers" (e.g. about 3-6). A "rotamer" is an energetically favorable conformation of an amino acid side chain. The number of rotamers for the various amino acid residues are reviewed in Ponders and Richards, J. Mol. Biol. 193: 775-791 (1987).

Unless stated otherwise, the term "antibody" specifically includes native human and non-human IgG1, IgG2, IgG3, IgG4, IgE, IgA, IgD and IgM antibodies, including naturally occurring variants. Thus, for example, the human IgM sequence is available under GenBank Accession Number X14940.1, while variants have been reported as GenBank CAB37838.1, CAC20458.1, AFM37312.1, X57331.1, and J00260.1.

The term "native" with reference to a polypeptide (e.g. an antibody or a J-chain) is used herein to refer to a polypeptide having a sequence that occurs in nature, regardless of its mode of preparation. Thus, the terms "native" and "native sequence" are used herein interchangeably, and expressly encompass recombinant polypeptides with a sequence that is found in nature.

The term "native sequence J-chain" or "native J-chain" as used herein refers to J-chain of native sequence IgM or IgA antibodies of any animal species, including mature human J-chain, the amino acid sequence of which is shown in FIG. 3 (SEQ ID NO: 1) and the J-chains of non-human animal species, including, without limitation, the native sequence J-chain polypeptides of SEQ ID NOs: 2 to 44 shown in FIG. 4 or the bat J-chain polypeptide (SEQ ID NO: 45) shown in FIG. 5.

The term "modified J-chain" is used herein to refer to variants of native sequence J-chain polypeptides comprising an extraneous binding moiety introduced into the native sequence. The introduction can be achieved by any means, including direct or indirect fusion of an extraneous binding moiety or by attachment through a chemical linker. The term "modified human J-chain" specifically encompasses, without limitation, a native sequence human J-chain of the amino acid sequence of SEQ ID NO: 1 modified by the introduction of a binding moiety. The term specifically encompasses, without limitation, a native sequence human J-chain of the amino acid sequence of SEQ ID NO: 1 modified by the introduction of an extraneous binding moiety which does not interfere with efficient polymerization (dimerization) of IgM or IgA and binding of such polymers (dimers) to a target The term "binding moiety" is used herein in the broadest sense to encompass any chemical entity capable of specific binding to a target, such as an antigen. Examples of binding moieties include, without limitation, antibodies, antigen-binding fragments of antibodies, antibody-drug conjugates, antibody-like molecules, antigen-binding fragments of antibody-like molecules, soluble and membrane-bound proteins, ligands, receptors, virus-like particles, protein toxins, enzymes, and alternative scaffolds. Preferred binding moieties are polypeptides (including peptides), preferably with a biological function. An exemplary biological function is the ability of a binding moiety to bind to and activate an effector cell, such as a B-cell, a T-cell, or a natural killer (NK)-cell.

The term "polypeptide" is used herein in the broadest sense and includes peptide sequences. The term "peptide" generally describes linear molecular chains of amino acids containing up to about 60, preferably up to about 30 amino acids covalently linked by peptide bonds.

The term "extraneous" with reference to a "binding moiety" is used herein to refer to a binding moiety not present in a reference native polypeptide sequence at the same location. Thus, an extraneous polypeptide sequence (including peptide sequences), might be comprised within the corresponding native sequence but at a different location. In a preferred embodiment, the "extraneous" sequence is not present in the corresponding native sequence in any location.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler et al. (1975) *Nature* 256:495 or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

An "isolated" antibody herein is one which has been identified and separated and/or recovered from a component of its natural environment in a recombinant host cell. Contaminant components of its natural environment are materials which would interfere with diagnostic or therapeutic uses for the antibody, and may include enzymes, hormones, and other proteinaceous or nonproteinaceous solutes, as well as undesired byproducts of the production. In a preferred embodiment, an isolated antibody herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of an amino acid sequencer, or (3) to homogeneity by SDS-PAGE under reducing or non-reducing conditions using Coomassie blue or, preferably, silver stain. Ordinarily, an isolated antibody will be prepared by at least one purification step.

The term "specific binding" or "specifically binds to" or is "specific for" refers to the binding of a binding moiety to a binding target, such as the binding of an antibody to a target antigen, e.g., an epitope on a particular polypeptide, peptide, or other target (e.g. a glycoprotein target), and means binding that is measurably different from a non-specific interaction (e.g., a non-specific interaction may be binding to bovine serum albumin or casein). Specific binding can be measured, for example, by determining binding of a binding moiety, or an antibody, or an antibody modified by introduction of a binding moiety, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-2000 or a BIAcore™-3000 (BIAcore, Inc., Piscataway, N.J.) at 25° C. with immobilized antigen CM5 chips at about 10 response units (RU).

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin The term "valent" as used herein denotes the presence of a specified number of binding sites in an antibody. As such, the terms "bivalent", "tetravalent", and "hexavalent" denote the presence of two binding sites, four binding sites, and six binding sites, respectively. Thus, if in a bispecific IgA antibody according to the present invention each binding unit is bivalent, the bispecific IgA antibody will have 4 valencies.

The term "epitope" includes any molecular determinant capable of specific binding to an antibody. In certain embodiments, epitope determinants include chemically active surface groupings of molecules such as amino acids, sugar side chains, phosphoryl, or sulfonyl, and, in certain embodiments, may have specific three-dimensional structural characteristics, and or specific charge characteristics. An epitope is a region of an antigen that is bound by an antibody. A "binding region" is a region on a binding target bound by a binding molecule.

"Polyepitopic specificity" refers to the ability to specifically bind to two or more different epitopes on the same or different target(s). "Monospecific" refers to the ability to bind only one epitope. According to one embodiment the bispecific IgM antibody binds to each epitope with an affinity of at least $10^{-7}$M, or $10^{-8}$M or better.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an antibody or trigger a cellular immune response. An immunogen refers to an antigen, which can elicit an immune response in an organism, particularly an animal, more particularly a mammal including a human. The term antigen includes regions known as antigenic determinants or epitopes, as defined above.

As used herein, the term "immunogenic" refers to substances, which elicit the production of antibodies, and/or activate T-cells and/or other reactive immune cells directed against an antigen of the immunogen.

An "antigen-binding site" or "antigen-binding region" of an antibody of the present invention typically contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs may be sufficient for binding to some binding targets. Thus, in some instances, the CDRs of a VH or a VL domain alone will be sufficient. Furthermore, certain antibodies might have non-CDR-associated binding sites for an antigen. Such binding sites are specifically included within the present definition.

The term "host cell" as used in the current application denotes any kind of cellular system which can be engineered to generate the antibodies according to the current invention. In one embodiment Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Design and Production of Antibodies with Modified J-Chain

IgM is the first immunoglobulin produced by B cells in response to stimulation by antigen and is present at around 1.5 mg/ml in serum with a half-life of 5 days. IgM is a pentameric or hexameric molecule. Just as IgG, IgM monomers consist of two light and two heavy chains. However, while IgG contains three heavy chain constant domains (CH1, CH2 and CH3), the heavy (μ) chain of IgM additionally contains a fourth constant domain (CH4), similarly to the ε heavy chains in IgE. This extra constant domain is located in place of the IgG and IgA proline-rich hinge region that is responsible for the rotational flexibility of the antigen-binding Fab domains relative to the Fc domain of IgG and IgA antibodies.

Five IgM monomers form a complex with an additional small polypeptide chain (the J-chain) to form a native IgM molecule. The J-chain is considered to facilitate polymerization of μ chains before IgM is secreted from antibody-producing cells. While crystallization of IgM has proved to be notoriously challenging, Czajkowsky and Shao (PNAS 106(35):14960-14965, 2009) recently published a homology-based structural model of IgM, based on the structure of the IgE Fc domain and the known disulfide pairings. The authors report that the human IgM pentamer is a mushroom-shaped molecule with a flexural bias. The IgM heavy (μ) chain contains five N-linked glycosylation sites: Asn-171, Asn-332, Asn-395, Asn-402 and Asn-563.

Immunoglobulin A (IgA), as the major class of antibody present in the mucosal secretions of most mammals, represents a key first line of defense against invasion by inhaled and ingested pathogens. IgA is also found at significant concentrations in the serum of many species, where it functions as a second line of defense mediating elimination of pathogens that have breached the mucosal surface. Receptors specific for the Fc region of IgA, FcαR, are key mediators of IgA effector function. Human IgA may have two different IgA heavy constant region (Cα) genes which give rise to the two subclasses, IgA1 and IgA2. The main difference between IgA1 and IgA2 resides in the hinge region that lies between the two Fab arms and the Fc region. IgA1 has an extended hinge region due to the insertion of a duplicated stretch of amino acids, which is absent in IgA2. IgA has the capacity to form dimers, in which two monomer units, each comprising two heavy chains and light chains, are postulated to be arranged in an end-to-end configuration stabilized by disulfide bridges and incorporation of a J-chain. Dimeric IgA, produced locally at mucosal sites, is transported across the epithelial cell boundary and out into the secretions by interaction with the polymeric immuno-globulin receptor (pIgR). During this process the pIgR is cleaved and the major fragment, termed secretory component (SC), becomes covalently attached to the IgA dimer.

Both IgA and IgM possess an 18-amino acid extension in the C terminus called the "tail-piece" (tp). The IgM (μap) and IgA (αtp) tail-pieces differ at seven amino acid positions. The IgM and IgA tail-pieces are highly conserved among various animal species. The conserved penultimate cysteine residue in the IgA and IgM tail-pieces has been demonstrated to be involved in polymerization. Both tail-pieces contain an N-linked carbohydrate addition site, the presence of which is required for dimer formation in IgA and J-chain incorporation and pentamer formation in IgM. However, the structure and composition of the N-linked carbohydrates in the tail-pieces differ, suggesting differences in the accessibility of the glycans to processing by glycosyl-transferases.

The nucleotide and/or protein sequences of J-chains of human, and various vertebrate animal species, such as cow, mouse, avian, amphibian, and rabbit, have been reported. The human J-chain contains eight cysteine residues, two (Cys13 and Cys69) are involved in disulfide bridges with the α or μ-chains (in IgA and IgM, respectively), and six are involved in intrachain disulfide bridges (Cys13: Cys101, Cys72: Cys92, Cys109: Cys134). The three-dimensional crystal structure of the J-chain has not been reported.

The present invention is based, at least in part, on the recognition that the J-chain of IgM and IgA antibodies can be modified by introduction of a binding specificity (binding moiety), without interfering with the ability of the IgM or IgA antibody to bind to its binding target(s). Accordingly, the present invention concerns modified J-chains comprising a binding moiety introduced into a native sequence J-chain, such as a native sequence human J-chain of SEQ ID NO: 1. The invention further concerns binding molecules comprising a modified J-chain. The binding molecule can, for example, be an IgM antibody, an IgA antibody, or an IgG/IgM or IgG/IgA hybrid antibody, which may contain an IgM or IgA tail-piece at the IgG heavy chain and thus combine the properties of IgG and IgA or IgA, including the ability to incorporate and form polymers with a modified J-chain of the present invention. For further details on IgG/IgM and IgG/IgA hybrid antibodies see, e.g. Koteswara et al., Clinical Immunology 2001, 101(1):21-31.

The modified J-chain comprises an extraneous binding moiety, which includes, but is not limited to, a polypeptide (including peptides) capable of specifically binding to a binding target, or catalytic components, such as enzyme-like proteases. As discussed earlier, the binding moieties include, without limitation, antibodies, antigen-binding fragments of antibodies, antibody-drug conjugates, antigen-binding fragments of antibody-drug conjugate, antibody-like molecules, antigen-binding fragments of antibody-like molecules, soluble and membrane-bound proteins, ligands, receptors, virus-like particles, protein toxins, catalytic components, such as enzymes and enzyme-like proteases, and alternative scaffolds. It is emphasized that any type of binding moiety can be introduced into a J-chain, following the teaching of the present disclosure, by appropriately selecting the location, type of addition (e.g. direct or indirect fusion, chemical tethering, etc.).

In a preferred embodiment, the binding moiety is an antibody or an antigen-binding fragment of an antibody (also referred to as an "antibody fragment"), including monospecific, bispecific, and multi-specific antibodies and antibody fragments. The term "antibody fragment" is used in the broadest sense and includes, without limitation, Fab, Fab', F(ab')$_2$, scFv, and (scFv)$_2$ fragments, complementarity determining region (CDR) fragments, linear antibodies, single-chain antibody molecules, minibodies, and multispecific antibodies formed from antibody fragments. In a preferred embodiment, the antibody fragment is a scFv.

In another preferred embodiment, the binding moiety is an antibody-like molecule, such as, for example, a human domain antibody (dAb), Dual-Affinity Re-Targeting (DART) molecule, a diabody, a di-diabody, dual-variable domain antibody, a Stacked Variable Domain antibody, a Small Modular ImmunoPharmaceutical (SMIP), a Surro-body, a strand-exchange engineered domain (SEED)-body, or TandAb.

The binding moiety may be a ligand, such as a neurotrophin, an interleukin, a soluble molecular factor or a growth factor.

Receptors, as binding molecules, include ion-channel-linked, G-protein-linked, and enzyme-linked cell surface receptors. Specific examples include, without limitation, ErbB1, ErbB2, ErbB3, ErbB4, TNFR, PDL1, and CTLA-4.

In a further preferred embodiment, the binding moiety is an alternative scaffold. In this context, the term "scaffold" is meant to describe a protein framework that can carry altered amino acids or sequence insertions that confer on protein variants the ability to bind specific targets. Protein alternative scaffolds include, without limitation, CTLA-4. tendamistat, fibronectin, lipocalins, T-cell receptor, CBM4-2, protein A domain, lm9, designed AR proteins, designed TPR proteins, zinc finger, pVIII, avian pancreatic polypeptide, GCN4, WW domain, SRC homology domains 2 and 3, PDZ domains, TEM-1, β-lactamase, GFP, thioredoxin, Staphylococcal nuclease, PHD-finger, c1-2, BPTI, APPI, HPSTI, ecotin, LACI-D1, LDTI, MTI-II, scorpion toxins, knottins, insect defensin A peptide, EETI-II, Min-23, CBD, PBP, cytochrome $b_{562}$, LDLreceptor domain A, γ-crystallin, ubiquitin, transferrin, C-type lectin-like domain. Preferred alternative scaffolds are darpins, fibronectin domains and adnectins. For further details see, Binz H K et al, 2005 *Nature Biotechnology* 23 (10): 1257-1268.

The binding moiety may be introduced into the native J-chain sequence at any location that allows the binding of the binding moiety to its binding target without interfering with the binding of the recipient IgM, IgA, IgG/IgM or IgG/IgA molecule to its binding target or binding targets. Preferred locations include at or near the C-terminus, at or near the N-terminus or at an internal location that, based on the three-dimensional structure of the J-chain is accessible. In preferred embodiments, the binding moiety is introduced into the native sequence J-chain without about 10 residues from the C-terminus or without about 10 amino acid residues from the N-terminus, where the native sequence J-chain preferably is human J-chain of SEQ ID NO: 1. In another embodiment, the binding moiety is introduced into the native sequence human J-chain of SEQ ID NO: 1 in between cysteine residues 92 and 101 of SEQ ID NO: 1, or at an equivalent location of another native sequence J-chain. In a further embodiment, the binding moiety is introduced into a native sequence J-chain, such as a J-chain of SEQ ID NO: 1, at or near a glycosylation site. Most preferably, the binding moiety is introduced into the native sequence human J-chain of SEQ ID NO: within about 10 amino acid residues from the C-terminus.

Introduction can be accomplished by direct or indirect fusion, i.e. by the combination of the J-chain and binding moiety amino acid sequences in one polypeptide chain by in-frame combination of their coding nucleotide sequences, with or without a peptide linker. The peptide linker (indirect fusion), if used, may, for example, be about 1 to 50, or about 1 to 40, or about 1 to 30, or about 1 to 20, or about 1 to 10, or about 10 to 20 amino acid residues, and may be present at one or both ends of the binding moiety to be introduced into the J-chain sequence. In a preferred embodiment, the peptide linker is about 10 to 20, or 10 to 15 amino acids long. In another preferred embodiment, the peptide linker is 15 amino acids long.

The binding moiety may also be appended to the native J-chain sequence by chemical linkage using heterobifunctional protein crosslinkers contain two different functional groups, which have their own reactivity and selectivity. These crosslinkers can be used in a one step process or can be used to create activated proteins, which can often be preserved and reacted with the second biomolecule in a separate step. Thus, for example, a heterobifunctional cross-linking reagent can be used to form conjugates between a J-chain and a binding moiety. The reactive groups include, without limitation imine reactive groups (such as NHS or Sulfo-NHS), maleimide groups, and the like. Such crosslinkers, which can be cleavable or non-cleavable, have been used, for example, in the formation of hapten carrier proteins and in preparing enzyme-antibody conjugates. Chemically, the cleavable crosslinkers specifically include, without limitation, disulfide-based, hydrazone, and peptide linkers. A well-known and much studied enzyme-labile linker is a valine-citrulline linker, but other peptide linkers are also known and suitable. Typical representatives of non-cleavable linkers include thioethers, such as SMCC (N-succinimidyl-4-(N-maleimidomethyl)-cyclohexane-1-carboxylate). For further details see, e.g. Ducry L and Stump B, *Bioconjugate Chem.* 2010, 21:5-13, the entire disclosure of which is expressly incorporated by reference herein. For listing of further suitable linkers see, e.g. Klein et al., *Protein Engineering, Design & Selection;* 2014, 27(10): 325-330, the entire disclosure of which is expressly incorporated by reference herein.

While the modified J-chain usually contains one extraneous binding moiety, it is also possible to introduce more than one binding moiety into a J-chain.

The modified J-chain may be produced by well-known techniques of recombinant DNA technology, by expressing nucleic acid encoding the modified J-chain in a suitable prokaryotic or eukaryotic host organism, such as CHO cells or *E. coli*. Thus, the modified J-chain may, for example, be expressed in *E. coli*, as described by Symersky et al., *Mol Immunol* 2000, 37:133-140.

In one embodiment, the J-chain can be initially modified by insertion of an enzyme recognition site, and post-translationally modified by a peptide or non-peptide linker, which can tether any extraneous binding moiety to the J-chain, such as, for example, cytotoxic small molecule to make an antibody-drug conjugate (ADC).

The modified J-chain can also be co-expressed with the heavy and light chains of the recipient IgM, IgA, IgG/IgM or IgG/IgA antibody. Although due to its complex structure, the large-scale production of recombinant IgM has been difficult, several recombinant production systems for IgM using non-lymphoid cells have been reported, including co-expression of the IgM heavy (H) and light (L) chains in C6 glioma cells, CHO cells, and HeLa cells (see, e.g. WO89/01975 and Wood et al., J. Immunol. 145, 3011-3016 (1990) for expression in CHO cells). Expression of an IgM monoclonal antibody in *E. coli*, with or without a J-chain, is described, e.g. in Azuma et al., *Clin Cancer Res* 2007, 13(9):2745-2750. Production of IgM in an immortalized human retina cell line expressing E1A and E1B proteins of an adenovirus is described in U. S. Application Publication No. 20060063234.

The recipient antibody may be monospecific, bispecific or multi-specific. Bispecific and multi-specific IgM and IgA binding molecules, including antibodies, are described, for example, in U.S. Application Ser. Nos. 61/874,277 and 61/937,984, the entire contents of which are hereby expressly incorporated by reference.

Applications of Antibodies with Modified J-Chain

Antibodies comprising a modified J-chain of the present invention have widespread therapeutic and diagnostic applications.

In one embodiment, antibodies comprising a modified J-chain bind to two or more sites on the same soluble target, such as, for example, VEGF, TNFα, or IL6. The purpose may, for example, be antagonizing multiple sites on the protein and/or increasing the avidity to a given target.

In another embodiment, the antibodies comprising a modified J-chain herein bind two or more sites on the same cell surface (receptor) target, such as EGFR or HER2

(ErbB2). Thus, for example, such antibodies might target both the 4D5 and the 2C4 epitopes on a HER2 molecule. This approach may increase bio-potency and/or avidity to a given target.

In yet another embodiment, the antibodies comprising the modified J-chains of the present invention bind two or more different soluble targets (globular proteins or peptides), e.g. TNFα and IL6, VEGFα and Ang2, or two cytokines. This approach might result, for example, in more complete blocking a specific pathway; blocking of the so called "cytokine storm," i.e. undesirable T cell activation resulting from certain multivalent bispecific antibodies, such as bispecific antibodies for the CD3 antigen, or coordinate an enzyme and its substrate, e.g. Factor IXa and Factor X. Specific examples include, without limitation, bispecific antibodies with modified J-chain, where a first specificity is directed to VEGF and a second specificity is directed to Ang2 or DLL4 (anti-angiogenesis), or a first specificity is directed to TNF and a second specificity is directed to Ang2 or IL-17 (anti-inflammatory properties), where either specificity may be introduced into the J-chain of an IgM, IgA, IgG/IgM or IgG/IgA antibody, or an antigen-binding fragment thereof.

In a further embodiment, antibodies comprising a modified J-chain may bind one or more soluble targets and one or more cell surface receptor targets, such as an angiogenic factor and neo-vascular specific receptor. The purpose of this approach may also be increased delivery and blockade at specific sites or tissues.

In a still further embodiment, antibodies comprising a modified J-chain are designed to bind two or more different cell surface receptor targets, such as, for example, HER1, HER2 (ErbB2) and HER3 (ErbB3), inhibiting multiple targets through the same or different pathways. This may result in enhancing specificity and selectivity and/or in more complete blocking of a given pathway. Specific examples of such antibodies include, without limitation, bispecific antibodies with a modified J-chain where one specificity is directed to HER2 and another specificity is directed to HER3; or one specificity is directed to EGFR (HER1) and another specificity is directed to HER2. Other bispecific IgM, IgA, IgG/IgM or IgG/IgA antibodies with a modified J-chain may, for example, bind to EGFR and HER3, IL-1α and IL-1β, IL-4 and IL-13, Ang-2 and VEGF-A, Factor IXA and Factor X, or IL-17A and IL-17F.

Antibodies comprising a modified J-chain of the present invention may also be designed to bind one or more soluble targets or cell surface receptor targets and one or more long residence time targets, such as, for example, TNFα and/or VEGF and serum albumin. These molecules are expected to have longer circulating half-life than binding molecules without the albumin specificity.

In a further embodiment, antibodies comprising a modified J-chain herein may bind one or more soluble targets and one or more matrix proteins and/or substrates, such as, for example, VEGFα and hyaluronic acid. The resultant multi-specific binding molecules may find utility, for example, in anti-angiogenic therapy of ocular conditions, such as age-related macular degeneration (AMD), due to their increased residence time in the intraocular space.

Antibodies comprising a modified J-chain and binding one or more soluble or receptor targets, plus one or more transporter receptors (e.g., transferrin receptor), e.g. anti-EGFRvIII (mutant form with exon III deleted) found glioblastoma combined with anti-transferrin specificity, can find utility in antibody delivery across blood brain barrier.

In a preferred embodiment, the IgM, IgA, IgG/IgM and IgG/IgA antibodies herein comprise a modified J-chain with binding specificity for an immune cell, such as a T-cell, NK-cell, a macrophage, or a neutrophil, and bind to an antigen expressed on a disease cell or pathogen. Since an IgM molecule comprises 5 binding units, and an IgA molecule is a dimer comprising two binding units, such molecules are significantly more potent due to their greater avidity than bispecific IgG antibodies. In addition, by activating and redirecting effector cells, e.g. effector T cells, to targeted disease cells, tissues or pathogens the IgM, IgA, IgG/IgM and IgG/IgA antibodies herein induce an immune response against the target, thereby further increasing potency and efficacy. Due to these beneficial properties, the IgM, IgA, IgG/IgM and IgG/IgA antibodies herein, comprising a modified J-chain, are especially advantageous in situations where IgG antibodies bind to their target with low affinity. Thus, in one embodiment, the IgM, IgA, IgG/IgM and IgG/IgA antibodies herein may comprise the binding domain of a therapeutic IgG antibody.

In certain embodiments, the IgM, IgA, IgG/IgM and IgG/IgA antibodies herein comprising a modified J-chain may be used for the treatment of cancer. It is anticipated that any type of tumor and any type of tumor-associated antigen may be targeted. Exemplary types of cancers include, without limitation, acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer. However, the skilled artisan will realize that tumor-associated antigens are known in the art for virtually any type of cancer.

Tumor-associated antigens that may be targeted by the IgM, IgA, IgG/IgM, or IgG/IgA antibodies of the presence invention include, without limitation, alpha-fetoprotein (AFP), associated antigens, Ba 733, BAGE, BrE3-antigen, CA125, CAMEL, CAP-1, carbonic anhydrase IX, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, HIF-1a, colon-specific antigen-p (CSAp), CEA (CEACAM5), CEACAM6, c-Met, DAM, EGFR (HER1, ErbB1), ErbB2 (HER2), ErbB4 (HER3), EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-.beta., HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, pancreatic cancer mucin, PD-1 receptor, placental growth factor, p53, PLAGL2, prostatic acid phosphatase, PSA, PRAIVIE, PSMA, PlGF, ILGF, ILGF-1R, IL-6, IL-25, RS5, RANTES, T101, SAGE, 5100, survivin, survivin-2B, TAC, TAG-72, tenascin, TRAIL receptors, TNF-.alpha., Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras.

As discussed above, for oncological applications, antibodies comprising a modified J-chain can be designed to trigger the killing function of immune cells against targeted cancer cells. Thus, for example, the J-chain of IgM, IgA, IgG/IgM or IgG/IgA antibodies, or antigen-binding fragments thereof, can be modified by introducing into a native J-chain a binding specificity for an immune cell, such as a T-cell or a Natural Killer (NK) cell, while the IgA, IgG/IgM or IgG/IgA antibody provides binding specificity to a target cell, e.g. a tumor marker, such as an oncogene, on the surface of a tumor cell, including, for example, any or more of the tumor-associated antigens listed above.

In the case of T-cells, cluster of differentiation 3 (CD3) is a multimeric protein complex, known historically as the T3 complex, and is composed of four distinct polypeptide chains (ε, γ, δ, ζ) that assemble and function as three pairs of dimers (εγ, εδ, ζζ). The CD3 complex serves as a T cell co-receptor that associates non-covalently with the T cell receptor (TCR). Components of this CD3 complex, especially CD3ε, are targets for a modified J-chain of an IgM antibody specifically binding to a tumor-associated antigen. Although the modified J-chain specific for effector T cells preferably binds to the CD3 (CD3ε) antigen, other antigens expressed on effector T cells are known and may be targeted by the modified J-chain. Exemplary T-cell antigens include, but are not limited to, CD2, CD3, CD4, CD5, CD6, CD8, CD25, CD28, CD30, CD40, CD40L, CD44, CD45, CD69 and CD90.

Exemplary IgM, IgA, IgG/IgM, or IgG/IgA antibodies including a modified J-chain with CD3 binding specificity, may include the binding regions of known IgG antibodies to tumor-associated antigens, such as, for example, blinatumomab (also known as MT103) (anti-CD19), CD19hA19 (anti-CD19, U.S. Pat. No. 7,109,304), hPAM4 (anti-mucin, U.S. Pat. No. 7,282,567), hA20 (anti-CD20, U.S. Pat. No. 7,251,164), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the disclosures of which are expressly incorporated by reference herein.

In a specific embodiment, an IgM, IgA, IgG/IgM, or IgG/IgA antibody comprising the CD19 binding region of blinatumomab comprises a modified J-chain comprising the CD3 binding region of blinatumomab. This antibody can be used, e.g. for the treatment of non-Hodgkin lymphoma, or acute lymphoblast leukemia of the B cell series (B-ALL).

In another specific embodiment, an IgM, IgA, IgG/IgM, or IgG/IgA antibody comprising the CD20 binding region of rituximab comprises a modified J-chain with CD3 specificity, such as a modified J-chain comprising the CD3 binding region of blinatumomab.

In yet another specific embodiment, an IgM, IgA, IgG/IgM, or IgG/IgA antibody comprising the EpCAM binding region of MT110 comprises a modified J-chain with CD3 specificity, such as a modified J-chain comprising the CD3 binding region of MT110. Such bispecific antibodies can be used for the treatment of gastrointestinal cancer.

Alternative antibodies that can provide binding regions for use in combination with a modified J-chain with CD3 binding specificity include, for example, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), atalizumab (anti-.alpha.4 integrin), omalizumab (anti-IgE); anti-TNF-.alpha. antibodies such as CDP571 (Ofei et al., 2011, *Diabetes* 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), BENLYSTA® (Human Genome Sciences); antibodies for therapy of Alzheimer's disease such as Alz 50 (Ksiezak-Reding et al., 1987, *J Biol Chem* 263:7943-47), gantenerumab, solanezumab and infliximab; anti-fibrin antibodies like 59D8, T2G1s, MH1; anti-CD38 antibodies such as MOR03087 (MorphoSys AG), MOR202 (Celgene), HuMax-CD38 (Genmab) or daratumumab (Johnson & Johnson); anti-HIV antibodies such as P4/D10 (U.S. Pat. No. 8,333,971), Ab 75, Ab 76, Ab 77 (Paulik et al., 1999, *Biochem Pharmacol* 58:1781-90), as well as the anti-HIV antibodies described in U.S. Pat. Nos. 5,831,034, 5,911,989, and Vcelar et al., AIDS 2007; 21(16):2161-2170 and Joos et al., *Antimicrob. Agents Chemother.* 2006; 50(5): 1773-9.

FIG. 19 lists exemplary target antigens for the treatment of hematologic cancer, epithelial tumor, and glycosyl-rich tumors, and exemplary antigens on T-cells, NK-cells, macrophages and neutrophils for targeting with a modified J-chain. It is to be understood that an IgM molecule binding to any of the listed tumor antigens can be combined with a modified J-chain with any of the listed binding specificities. Thus, any antibody target listed in the left column of the table can be combined with any modified J-chain target listed in the right column.

In a preferred embodiment, an IgM pentamer provides binding specificity to target cells, such as B-cells, while a binding domain to an effector cell, e.g. a T cell can be covalently attached to the J-chain of the IgM antibody. Thus, the J-chain can be modified by covalent attachment of a CD3 (CD3ε) binding domain. In this configuration, the IgM pentamer (comprising 10 copies of heavy chain and 10 copies of light chain) provides binding specificity to the target B-cells, while the T-cell tethering of the J-chain delivers cytotoxic potency. In other words, the IgM antibody binding to a tumor target additionally acquires a T-cell binding function. The CD3 binding domain covalently attached to a native J-chain, or a variant of a native J-chain, can, for example be a single-chain Fv (scFv) of an anti-CD3 antibody, or a naturally occurring heavy chain only antibody, e.g. a camelid (camels, llamas, alpacas) or single-chain antibody of cartilaginous fish (sharks, rays), a scaffold, e.g.

fibronectin (e.g. fibronectin III) with CD3 binding specificity. While certain preferred embodiments are specifically referred to herein, it is to be understood that IgM, IgA, IgG/IgM and IgG/IgA antibodies with binding specificity to any target, such as any tumor antigen, comprising a modified J-chain binding to any T-cell marker are contemplated and are within the scope of the present invention.

In one embodiment, a multi-specific IgM, IgA, IgG/IgM or IgG/IgA antibody binds to one or more of the tumor targets listed above, while the J-chain is modified to bind to CD3c. In a preferred embodiment, the multi-specific IgM, IgA, IgG/IgM or IgG/IgA antibody binds to one or more of the tumor targets listed in FIG. 19, while the J-chain is modified to bind to CD3c.

Natural killer (NK) cells are important components of the innate immunity and play a key role in host defense by virtue of their ability to release cytokines and to mediate cytolytic activity against tumor cells and virus-infected cells. NK cell antigens include, without limitation, CD16, CD32a, CD56, CD57, CD64, CD117 (or c-kit), adhesion molecules including lymphocyte-associated molecule-2 (LFA-2 or CD2), LFA-3 (CD58), and LFA-1 (CD11a/CD18).

Examples of NK cell engaging bispecific antibodies with modified J-chain include IgM, IgA, IgG/IgM and IgG/IgA antibodies with binding specificity to any of the tumor antigens listed above comprising a modified J-chain binding to an NK cell. In a particular embodiment, a bispecific IgM, IgA, IgG/IgM and IgG/IgA antibody with HER2 binding specificity comprises a J-chain modified to bind CD16, CD32a, CD56, or CD64. In another preferred embodiment, a multi-specific IgM, IgA, IgG/IgM or IgG/IgA antibody binds to any of the tumor targets listed in the left column of the table in FIG. 19, and the J-chain is modified to bind CD16, CD64 or NKG2D on NK cells.

Macrophage engagement in the J-chain modified antibodies of the present invention can be provided, for example, by introducing a CD14 specificity into the J-chain.

In one embodiment, a multi-specific IgM, IgA, IgG/IgM or IgG/IgA antibody binds to one or more of the tumor targets listed above, while the J-chain is modified to bind to CD14. In a preferred embodiment, the multi-specific IgM, IgA, IgG/IgM or IgG/IgA antibody binds to one or more of the tumor targets listed in FIG. 19, while the J-chain is modified to bind to CD14.

The IgM, IgA, IgG/IgM and IgG/IgA antibodies with modified J-chain can target carbohydrate-based antigens, see, e.g. a review article by Cazet et al., *Breast Cancer Research*; 2010, 12:204. Carbohydrate-based tumor antigens have been shown to have good tumor association, with alternative forma of glycosylation that allow the production of IgG antibodies binding to such antigens with reasonable specificity but not necessarily high affinity. Using IgM, IgA, IgG/IgM, or IgG/IgA antibodies with associated increased avidity against this class of antigens represents great opportunities for new therapeutic antibodies, especially coupled with effector cell mobilization achieved by J-chain modification. In one preferred embodiment, the IgM, IgA, IgG/IgM and IgG/IgA antibody binds to one or more carbohydrate-based tumor antigen, while the J-chain is modified to bind any of the effector cells listed in FIG. 19.

In another preferred embodiment, the IgM, IgA, IgG/IgM and IgG/IgA antibodies with modified J-chain can be used as part of IgM, IgA, IgG/IgM or IgG/IgA antibodies directed against pathogens. In a preferred embodiment, the pathogens are selected from the group consisting of HIV virus, *Mycobacterium tuberculosis*, *Streptococcus agalactiae*, methicillin-resistant *Staphylococcus aureus*, *Legionella pneumophila*, *Streptococcus pyogenes*, *Escherichia coli*, *Neisseria gonorrhoeae*, *Neisseria meningitidis*, Pneumococcus, *Cryptococcus neoformans*, *Histoplasma capsulatum*, *Hemophilus influenzae* B, *Treponema pallidum*, Lyme disease spirochetes, *Pseudomonas aeruginosa*, *Mycobacterium leprae*, *Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japonicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M. hyorhinis*, *M. orale*, *M. arginini*, *Acholeplasma laidlawii*, *M. salivarium* and *M. pneumoniae*, as disclosed in U.S. Pat. No. 6,440,416.

In this embodiment, the immune effector cell may, for example, be a neutrophil.

FIG. 19 specifically lists viral antigens as targets for the IgM, IgA, IgG/IgM and IgG/IgA antibodies herein, in combination with neutrophil markers which can be targeted by the modified J-chain of such antibodies.

It is noted that the IgM, IgA, IgG/IgM and IgG/IgA antibodies herein may also target carbohydrate antigens on carbohydrate rich cancers. Such antigens include CEA, CA-125, TADG78, Sialyl Lewis-X (CD15), for example.

In all embodiments, the binding moiety (binding unit) used to modify a native J-chain may be introduced before or after the J-chain. Thus, a modified J-chain with CD3 binding specificity may have an anti-CD3$_{scFv}$-J or a J-anti-CD3$_{scFv}$ configuration. The sequence (SEQ ID NO: 46) and structure of an anti-CD3 single chain Fv comprising the J-chain at the C-terminus (anti-CD3$_{scFv}$-J) is shown in FIG. 8. The sequence (SEQ ID NO: 47) and structure of an anti-CD3 single chain Fv comprising the J-chain at the N-terminus (J-anti-CD3$_{scFv}$) is shown in FIG. 9. Due to their increased avidity such antibodies are superior relative to bispecific IgG antibodies. For example, as a result, they are suitable for targeting low copy-number targets, such as Rituxan resistant Burkitt lymphoma cells characterized by low level of CD20 expression. In addition, the IgM, IgA, IgG/IgM and IgG/IgA antibodies herein comprising a modified J-chain have greatly enhanced potency relative to bispecific IgG antibodies.

Pharmaceutical Compositions of Antibodies with Modified J-Chain

For therapeutic uses, antibodies comprising a modified J-chain may be formulated into pharmaceutical compositions. A pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The compositions may also contain adjuvants such as preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

The following examples sequence listing and figures are provided to aid the understanding of the present invention, the true scope of which is set forth in the appended claims. It is understood that modifications can be made in the procedures set forth without departing from the spirit of the invention.

Further details of the invention are illustrated by the following, non-limiting Examples.

EXAMPLES

Example 1: Preparation of a Bispecific Anti-CDIM IgM Antibody Comprising a Modified J-Chain Binding CD3

1. Generation of DNA Constructs with Designed Mutations a. DNA Construct Synthesis.

All the DNA constructs with designed mutations are synthesized by the commercial vendors (Genescript), with compatible restriction sites at both ends for subcloning into respective expression vectors.

b. Constructing Expression Vectors.

The synthesized DNA constructs are re-suspended in Tris-EDTA buffer at 1 µg/ml. DNA (1 µg) is subjected to enzyme digestion and the synthesized gene is separated from the carrier plasmid DNA by electrophoresis. The digested DNA is ligated to pre-digested plasmid DNA (pCAGGS for J-chain, Gene 108 (1991) 193-200) by standard molecular biology techniques. The ligated DNA is transformed into competent bacteria and plated on LB plates with multiple selective antibiotics. Several bacterial colonies are picked, and DNA preparations are made by standard molecular biology techniques. The prepared DNA are verified by sequencing. Only the bacterial clones with 100% match of DNA sequence with the designed DNA sequence are used for plasmid DNA preparation and subsequently for cell transfection.

c. Different J-Chains.

In order to demonstrate that J-chain variants will be able to couple with IgM, two different J-chain variants are constructed with distinct fusion sites incorporating anti-CD3 antibody (OKT3 scFv).

i. This construct is composed of a scFv of OKT3 (anti-CD3) fused with N-terminus of human J-chain (CD3scFv-15 aa Linker-J):

```
                                       (SEQ ID NO: 46)
QVQLQQSGAELARPGASVKMSCKASGYTFTRYTMHWVKQRPGQ

GLEWIGYINPSRGYTNYNQKFKDKATLTTDKSSSTAYMQLSSLTSE

DSAVYYCARYYDDHYSLDYWGQGTTLTVSSGGGGSGGGGSGGG

GSQIVLTQSPAIMSASPGEKVTMTCSASSSVSYMNWYQQKSGTSP

KRWIYDTSKLASGVPAHFRGSGSGTSYSLTISGMEAEDAATYYCQ

QWSSNPFTFGSGTKLEIKGGGGSGGGGSGGGGSQEDERIVLVDNK

CKCARITSRIIRSSEDPNEDIVERNIRIIVPLNNRENISDPTSPLRTRFV

YHLSDLCKKCDPTEVELDNQIVTATQSNICDEDSATETCYTYDRN

KCYTAVVPLVYGGETKMVETALTPDACYPDGGGSEQKLISEEDLN

SAVDHHHHHH-
```

This construct has a molecular weight about 45 kD and able to bind to soluble epsilon chain of CD3 (Sino Biological), or T cells; and is able to bind to anti-myc monoclonal antibody 4A6 or other anti-myc antibodies.

ii. This construct is composed of a scFv of OKT3 (anti-CD3) fused with C-terminus of human J-chain (J-15 aa Linker-CD3scFv):

```
                                       (SEQ ID NO: 47)
QEDERIVLVDNKCKCARITSRIIRSSEDPNEDIVERNIRIIVPLNNREN

ISDPTSPLRTRFVYHLSDLCKKCDPTEVELDNQIVTATQSNICDEDS

ATETCYTYDRNKCYTAVVPLVYGGETKMVETALTPDACYPDGGG

GSGGGGSGGGGSQVQLQQSGAELARPGASVKMSCKASGYTFTRY

TMHWVKQRPGQGLEWIGYINPSRGYTNYNQKFKDKATLTTDKSS

STAYMQLSSLTSEDSAVYYCARYYDDHYSLDYWGQGTTLTVSSG

GGGSGGGGSGGGGSQIVLTQSPAIMSASPGEKVTMTCSASSSVSY

MNWYQQKSGTSPKRWIYDTSKLASGVPAHFRGSGSGTSYSLTISG

MEAEDAATYYCQQWSSNPFTFGSGTKLEIKEQKLISEEDLNSAVD

HHHHHH-
```

This J-CD3scFv construct has a molecular weight about 45 kD and is able to bind to soluble epsilon chain of CD3 (Sino Biological), or T cells; and is able to bind to anti-myc monoclonal antibody 4A6 or other anti-myc antibodies.

d. IgM Heavy Chain:

This heavy chain construct has a full length μ, chain for IGM-55.5 which binds CDIM on the surface of B-cells:

(SEQ ID NO: 3)
```
QVQLQQWGAGLLKPSETLSLTCAVYGGSFSGYYWSWIRQPPGKG

LEWIGEINHSGSTNYNPSLKSRVTISVDTSKNQFSLKLSSVTAADTA

VYYCARGRMAWGASVNFDYWGQGTLVTVSSGSASAPTLFPLVSC

ENSPSDTSSVAVGCLAQDFLPDSITFSWKYKNNSDISSTRGFPSVLR

GGKYAATSQVLLPSKDVMQGTDEHVVCKVQHPNGNKEKNVPLP

VIAELPPKVSVFVPPRDGFFGNPRKSKLICQATGFSPRQIQVSWLRE

GKQVGSGVTTDQVQAEAKESGPTTYKVTSTLTIKESDWLSQSMFT

CRVDHRGLTFQQNASSMCVPDQDTAIRVFAIPPSFASIFLTKSTKLT

CLVTDLTTYDSVTISWTRQNGEAVKTHTNISESHPNATFSAVGEAS

ICEDDWNSGERFTCTVTHTDLPSPLKQTISRPKGVALHRPDVYLLP

PAREQLNLRESATITCLVTGFSPADVFVQWMQRGQPLSPEKYVTS

APMPEPQAPGRYFAHSILTVSEEEWNTGETYTCVVAHEALPNRVT

ERTVDKSTGKPTLYNVSLVMSDTAGTCY
```

This heavy chain construct has a molecular weight about 64 kD and when co-expressed with light chain, the resultant IgM is able to bind to CDIM positive B cells.

e. Light Chain for IGM-55.5 Known as IGM-55.5, which Binds CDIM (Cell Death Inducing Molecule) on the Surface of B-Cells:

(SEQ ID NO: 5)
```
DIQMTQSPSSLSASVGDRVTITCRASQSISSYLNWYQQKPGKAPKL

LIYAASSLQSGVPSRFSGSGSGTDFTLTISSLQPEDFATYYCQQSYS

TPITFGQGTRLEIKRTVAAPSVFIFPPSDEQLKSGTASVVCLLNNFYP

REAKVQWKVDNALQSGNSQESVTEQDSKDSTYSLSSTLTLSKADY

EKHKVYACEVTHQGLSSPVTKSFNRGEC
```

The light chain construct has a molecular weight about 24 kD and when co-expressed with the appropriate heavy chain (SEQ ID NO 3) is able to bind to CDIM positive B cells.

2. Protein Expression, Purification and Characterization a. Transfection.

Heavy, Light and Modified J-chain DNA is transfected into CHO cells. DNA for expression vectors are mixed typically in 1:1:1 ratio with PEI and then added to CHO—S cells. PEI transfection with CHO—S cells is conducted according to established techniques (see "Biotechnology and Bioengineering, Vol 87, 553-545").

b. Immunoprecipitation i. Capture Select IgM (BAC, Thermo Fisher). IgM proteins from transfected CHO cell supernatants are partially purified by immuno-precipitation with Capture Select IgM affinity matrix according to manufacturers' protocol (GE Life Sciences). After incubation at room temperature for 2 hours, the affinity matrix is separated from the supernatant by centrifugation. The matrix is further washed with PBS for 3 times before the PBS is carefully removed. The captured protein is eluted from the matrix by incubating with NuPage LDS protein buffer (Life Technology) for 5 minutes.

ii. Anti-myc agarose affinity matrix (Sigma). IgM proteins from transfected CHO cell supernatants are partially purified by immunoprecipitation with anti-myc affinity matrix according to manufacturers' protocol. After incubation at room temperature for 2 hours, the affinity matrix is separated from the supernatant by centrifugation. The matrix is further washed with PBS for 3 times before the PBS is carefully removed after the final wash. The captured protein is eluted from the matrix by incubating with NuPage LDS protein buffer (Life Technology) for 5 minutes.

c. Gel Electrophoresis

Non-Reducing SDS PAGE.

Non-reducing SDS PAGE separates native IgM and its mutant forms according to size. Pentameric IgM, composed of homodimeric heavy and light chains, produces a protein band of approximately 1,000,000 molecular weight. NuPage LDS Sample Buffer (Life Technologies) is added to IgM protein samples at 25 C for 30 minutes before loading onto the gel. NativePage Novex 3-12% Bis-Tris Gel (Life Technologies) is used with Novex Tris-Acetate SDS Running Buffer (Life Technologies). Run gel until the dye front reaches the bottom of the gel.

Reducing SDS-PAGE.

NuPage LDS sample buffer (Life Technologies) and NuPage reducing agent dithiothreitol (Life Technologies) are added to IgM protein samples and heated to 80° C. for 10 minutes before loading on NuPage Novex 4-12% Bis-Tris Gel (Life Technologies). NuPage IVIES SDS Running Buffer (Life Technologies) is used for gel electrophoresis. Gels are run until the dye front reaches the bottom of the gel. After electrophoresis is complete, remove gel from apparatus and stain the gel using Colloidal Blue Staining (Life Technologies).

Western Blot Detection.

After electrophoresis is complete, remove gel from XCell SureLock Mini-Cell. Transfer to PVDF membrane at 30 volts for 1 hour (refer to Life Technologies' manual). Block with 20 ml 3% BSA in PBST at 25 C for 1 hour.

For anti-J-chain Western blot, add anti-J (SP105, Thermo Fisher) at 1:500 in 3% BSA in PBST overnight at 4° C. Wash with PBST four times at room temperature. Add HRP-Goat anti rabbit IgG (Jackson Immunology) at 1:5,000 in 3% BSA in PBST for 1 hour at room temperature. Wash with PBST 4 times at room temperature. Add 10 ml of HRP chemiluminescent substrate (Thermo Fisher) for 10 minutes before exposing the blot to film. Anti-J-chain antibody only reacts with IgM which is co-expressed with either unmodified J-chain (FIG. 6) or modified J-chain (FIG. 7).

For anti-myc western blot, add anti-myc (4A6, Millipore) at 1:200 in 3% BSA in PBST for overnight at 4° C. Wash with PBST four times at room temperature. Add HRP-Goat anti-mouse IgG (Jackson Immunology) at 1:5,000 in 3% BSA in PBST for 1 hour at room temperature. Wash with PBST 4 times at room temperature. Add 10 ml of HRP chemiluminescent substrate (Thermo Fisher) for 10 minutes before exposing the blot to film. Anti-myc antibody only reacts with modified J-chain with myc tag (FIG. 2).

3. Bi-Specific Functional Analysis a. FACS Analysis of Target Binding.

IGM-55.5 with CD3scFv-J or IGM-55.5 with J-CD3scFv binding to T cells is confirmed by binding of antibody to T cell line (Jurkat, CD3 positive cell line) and B cell line (Nalm6, negative control cell line). After washing, rhodamine labeled 4A6 is added to the cell suspension. The cell target binding is detected by MFI of both positive and negative control cells with or without CD3 antigen.

IGM-55.5 with CD3scFv-J or IGM-55.5 with J-CD3scFv binding to CDIM expressing cells is confirmed by binding of antibody to positive cell line (Daudi, positive cell line) and negative cell line (Peer). After washing, rhodamine labeled 4A6 is added to the cell suspension. The cell target binding is detected by MFI of both positive and negative control cells with or without CDIM antigen.

b. FACS Analysis of T-Cell Mediated B-Cell Killing in Co-Culture.

Raji, a CD19+CD20+ B cell line, was co-cultured with T-ALL, a CD8+ Cytolytic T cell line with CD20 IgM x J-wild-type or CD20 IgM x CD3-J chain for 24 hours at 37 degrees, 5% CO2. Cell were harvested and stained with fluorescent antibodies to CD3 (552852BD Biosciences) and CD19 (555413BD Biosciences) and analyzed by flow cytometry to assess viable B cells.

c. Complement Dependent Cytotoxicity of B-Cells.

Ramos, a CD20+ cell line was seeded in 96 well half area white plates at 25,000 cells/well. Antibody and human complement (5% final, Quidel) were added to initiate complement dependent cytotoxicity and the number of viable cells were measured using Cell Titer Glo and manufacturer's protocol. Luminescence was measured on an Envision multimode reader (Perkin Elmer) using 0.1 s integration time per well. Percent viable cells was calculated by normalizing the luminescence values (Relative luminescence units—RLU) versus wells with no added drug. Data were analyzed using GraphPad Prism and a four-parameter fit with top and bottom values fixed at 100 and 0% viability respectively.

Multi-specific binding and multi-specific functional analysis can be performed in a similar manner using techniques known in the art, such as those described above.

Example 2: Molecular Cloning, Expression and Purification of a Bispecific Anti-CD20 IgM Antibody with a Modified J-Chain Carrying an Anti-CD3 Binding scFv This example describes the preparation of the molecular cloning, expression and purification of a further IgM antibody targeting a different B-cell antigen (CD20) and a modified J-chain binding to CD3. The DNA corresponding to the heavy and light chain sequences below was prepared using the methods as described in Example 1.

```
SEQ ID NO: 48: IgM Light chain sequence of the
anti-CD20 antibody (rituximab)
MDMRVPAQLLGLLLLWLRGARCQIVLSQSPAILSASPGEKVTMTCRASSS

VSYIHWFQQKPGSSPKPWIYATSNLASGVPVRFSGSGSGTSYSLTISRVE

AEDAATYYCQQWTSNPPTFGGGTKLEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

SEQ ID NO: 49: IgM Heavy chain sequence of the
anti-CD20 antibody (rituximab)
MGWSYIILFLVATATGVHSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSSGSASAPTLFP

LVSCENSPSDTSSVAVGCLAQDFLPDSITFSWKYKNNSDISSTRGFPSVL

RGGKYAATSQVLLPSKDVMQGTDEHVVCKVQHPNGNKEKNVPLPVIAELP

PKVSVFVPPRDGFEGNPRKSKLICQATGFSPRQIQVSWLREGKQVGSGVT

TDQVQAEAKESGPTTYKVTSTLTIKESDWLSQSMFTCRVDHRGLTFQQNA

SSMCVPDQDTAIRVFAIPPSFASIFLTKSTKLTCLVTDLTTYDSVTISWT

RQNGEAVKTHTNISESHPNATFSAVGEASICEDDWNSGERFTCTVTHTDL

PSPLKQTISRPKGVALHRPDVYLLPPAREQLNLRESATITCLVTGFSPAD

VFVQWMQRGQPLSPEKYVTSAPMPEPQAPGRYFAHSILTVSEEEWNTGET

YTCVVAHEALPNRVTERTVDKSTGKPTLYNVSLVMSDTAGTCY
```

The DNA corresponding to these heavy and light chains as well as that corresponding to either the wild-type (wt) J-chain, 015J or J150 J-chain sequences described in Example 1 were co-transfected into HEK293 cells and proteins expressed and purified using the camelid resin as described before. As shown in FIG. 13, all four proteins express well. The anti-CD20 IgM hexamer without J-chain is clearly resolved from the J-chain containing pentamers for the IgM pentamer with the wild type J-chain as well as for the bispecific IgM's where the anti-CD3 scFv is linked to the J-chain in either orientation (015J or J150).

Example 3: Molecular Cloning, Expression and Purification of Bispecific Anti-CD20 IgM Antibody Comprising a Modified J-Chain Carrying a Different Anti-CD3 Binding scFv To establish that assembly of bispecific IgM is feasible with a modified J-chain carrying an anti-CD3 scFv of a different sequence than that used Examples 1 and 2, a J-chain carrying the variable regions from the antibody Visilizumab (Nuvion) was performed. Shown below are the sequences for two J-chains with the scFv corresponding to Visilizumab (V) fused to the J-chain through a linker containing 15 amino acids in two different orientations—V15J and J15V.

```
SEQ ID NO: 50: J chain sequence for V15J
MGWSYIILFLVATATGVHSQVQLVQSGAEVKKPGASVKVSCKASGYTFIS

YTMHWVRQAPGQGLEWMGYINPRSGYTHYNQKLKDKATLTADKSASTAYM

ELSSLRSEDTAVYYCARSAYYDYDGFAYWGQGTLVTVSSGGGGSGGGGSG

GGGSDIQMTQSPSSLSASVGDRVTITCSASSSVSYMNWYQQKPGKAPKRL

IYDTSKLASGVPSRFSGSGSGTDFTLTISSLQPEDFATYYCQQWSSNPPT

FGGGTKLEIKGGGGSGGGGSGGGGSQEDERIVLVDNKCKCARITSRIIRS

SEDPNEDIVERNIRIIVPLNNRENISDPTSPLRTRFVYHLSDLCKKCDPT

EVELDNQIVTATQSNICDEDSATETCYTYDRNKCYTAVVPLVYGGETKMV

ETALTPDACYPD

SEQ ID NO: 51: J-chain sequence for J15V
MKNHLLFWGVLAVFIKAVHVKAQEDERIVLVDNKCKCARITSRIIRSSED

PNEDIVERNIRIIVPLNNRENISDPTSPLRTRFVYHLSDLCKKCDPTEVE

LDNQIVTATQSNICDEDSATETCYTYDRNKCYTAVVPLVYGGETKMVETA

LTPDACYPDGGGGSGGGGSGGGGSQVQLVQSGAEVKKPGASVKVSCKASG

YTFISYTMHWVRQAPGQGLEWMGYINPRSGYTHYNQKLKDKATLTADKSA

STAYMELSSLRSEDTAVYYCARSAYYDYDGFAYWGQGTLVTVSSGGGGSG

GGGSGGGGSDIQMTQSPSSLSASVGDRVTITCSASSSVSYMNWYQQKPGK
```

```
APKRLIYDTSKLASGVPSRFSGSGSGTDFTLTISSLQPEDFATYYCQQWS

SNPPTFGGGTKLEIK
```

As described in Example 1, DNA corresponding to these sequences was synthesized and transfected into EIEK293 cells along with the heavy and light chains for anti-CD20 IgM to produce protein which was then purified using the camelid antibody affinity matrix specific for IgM. As shown in FIG. 13, J-chains fused to the new anti-CD3 scFv with the 15 aa linker are able to incorporate into the IgM and the pentameric form of bi-specific IgM with the corresponding J-chain is clearly distinguishable from the hexameric form without a J-chain.

Example 4: Molecular Cloning, Expression and Purification of an IgM Comprising an Anti-CD16 Camelid Modified J-Chain Versions of a Second Effector Cell Binding Domain—Anti-CD16 Camelid This example demonstrates that it is possible to link a binding moiety different from an scFv to a J-chain, which is directed to a different target on a different effector cell population. A camelid Vhh sequence shown below was used, that was selected for binding to the CD16 antigen on natural killer cells (NK cells). Once again, this sequence was linked to a J-chain using a flexible 15 aa linker to produce C15J. The bispecific IgM was expressed and purified as described in Example 1 and analyzed on hybrid gels. Formation of a pentameric species is clearly seen. Further, incorporation of the C15J J-chain into the pentameric IgM was established using western blot (FIG. 18).

```
SEQ ID NO: 52: J-chain sequence for C15J
MGWSYIILFLVATATGVHSEVQLVESGGELVQAGGSLRLSCAASG

LTFSSYNMGWFRRAPGKEREFVASITWSGRDTFYADSVKGRFTISR

DNAKNTVYLQMSSLKPEDTAVYYCAANPWPVAAPRSGTYWGQG

TQVTVSSGGGGSGGGGSGGGGSQEDERIVLVDNKCKCARITSRIIR

SSEDPNEDIVERNIRIIVPLNNRENISDPTSPLRTRFVYHLSDLCKKC

DPTEVELDNQIVTATQSNICDEDSATETCYTYDRNKCYTAVVPLV

YGGETKMVETALTPDACYPD
```

Example 5: Analysis of Complement Dependent Cytotoxicity for Family of IgM's with and without Incorporated J-Chains Complement dependent cytotoxicity is a key mechanism for cell killing by antibodies. IgM antibodies are known to have enhanced complement dependent cell killing (CDC) due to their multimeric form. A key aspect of this invention was to test if incorporation of modified J-chains, which carry scFv or camelid Vhh binders of effector cells at either their C- or N-termini, causes interference with binding of C1q—the key component of the complement pathway, and therefore may inhibit CDC. We measured the CDC activity of each of the IgM and bispecific IgM constructs. As shown in FIG. 14, we find that incorporation of the modified J-chain has, unexpectedly, no deleterious effect on the CDC activity of our bispecific IgM's, Moreover, with the linker lengths we tested, we find that the bispecific IgM's have CDC activity between 60-100-fold enhanced over the corresponding IgG on a molar basis (FIG. 14).

Example 6: Analysis of T-Cell Dependent B-Cell Killing by Bispecific IgM in In Vitro Co-Culture Engagement of effector T-cells by bispecific IgM antibodies with a modified J-chain is expected to greatly enhance killing of the target B-cell populations compared to the IgM carrying no J-chain or the wild type J-chain. To test cell killing in co-culture, we performed a cell killing assay as described in Example 1. Antibody at a single high concentration (100 ng/mL) incubated with CD20+ Raji cells and CD3+ effector T-ALL cells. As shown in FIG. 15, the bispecific IgM carrying a CD3 binding scFv on its J-chain is able to cause complete killing of B-cells. The same experiment done as a dose response shows that there is a greater than 300-fold improvement in B-cell killing compared to the IgM that carries no scFv capable of engaging T-cells. Complete killing of B-cells by bispecific IgM is observed at concentrations as low as 10 ng/mL.

Example 7: Demonstration of T-Cell Dependent B-Cell Killing In Vivo in NSG Mouse Model In order to test the bispecific IgM antibodies we made in an in vivo context, we performed experiments with humanized non-obese diabetic severe combined immune-deficient gamma null (NSG) mice. These mice have severely impaired immune function and lack mouse T- and B-lymphocytes. They are reconstituted with human CD34+ stem cells to create mice with essentially human lymphocyte populations. When CD20 IgM x CD3-J chain was dosed intravenously in these animals at 0.5 mg/kg and whole blood was obtained and analyzed by flow cytometry for circulating levels of human B cells, we observed a complete depletion of the B-cell population even with treatments as short as 6 hours (FIG. 17).

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. Various examples of changes, substitutions, and alterations are ascertainable by one skilled in the art and could be made without departing from the spirit and scope disclosed herein.

What is claimed is:

1. A polymeric antibody that specifically binds to an antigen, the polymeric antibody comprising at least two immunoglobulin monomers and a modified J-chain, wherein the modified J-chain comprises an extraneous binding moiety introduced into a native J-chain comprising SEQ ID NO: 1, wherein the extraneous binding moiety is introduced into the native J-chain at or within 10 residues from the C- or N-terminus of the native J-chain, and wherein each immunoglobulin monomer comprises (i) a Cμ4 and an IgM tail-piece (μtp) domain, or (ii) a Cα3 and an IgA tail-piece (αtp) domain.

2. The polymeric antibody of claim 1, wherein the extraneous binding moiety is introduced into the native J-chain by indirect fusion through a peptide linker.

3. The polymeric antibody of claim 2, wherein the peptide linker is located at or around the C- and/or N-terminus of the binding moiety.

4. The polymeric antibody of claim 2, wherein the extraneous binding moiety is introduced into the native J-chain at the C-terminus of the native J-chain.

5. The polymeric antibody of claim 2, wherein the extraneous binding moiety is introduced into the native J-chain at the N-terminus of the native J-chain.

6. The polymeric antibody of claim 2, wherein the peptide linker is about 10 to 20 amino acids long.

7. The polymeric antibody of claim 2, wherein the peptide linker is 15 amino acids long.

8. The polymeric antibody of claim 2, further comprising an additional extraneous binding moiety, wherein the additional extraneous binding moiety is a polypeptide introduced into the native J-chain by direct or indirect fusion.

9. The polymeric antibody of claim 1, wherein the extraneous binding moiety is selected from the group consisting of an antibody, an antigen-binding fragment of an antibody, an antibody-drug conjugate, an antibody-like molecule, an antigen-binding fragment of an antibody-like molecule, a soluble protein, a ligand, a receptor, a virus-like particle, a protein toxin, an enzyme, a darpin, a fibronectin domain, an adnectin, and a knottin.

10. The polymeric antibody of claim 9, wherein the extraneous binding moiety is an antigen-binding fragment of an antibody selected from the group consisting of an F(ab')2, an F(ab)2, an Fab', an Fab, an Fv, an scFv, and a single domain antibody.

11. The polymeric antibody of claim 10, wherein the antigen-binding fragment is an scFv.

12. The polymeric antibody of claim 1, wherein the extraneous binding moiety binds to an effector cell selected from the group consisting of a T-cell, a natural killer (NK) cell, a macrophage, and a neutrophil.

13. The polymeric antibody of claim 12, wherein the effector cell is a T-cell.

14. The polymeric antibody of claim 13, wherein the extraneous binding moiety binds to CD3ε on the T-cell.

15. The polymeric antibody of claim 13, wherein the extraneous binding moiety binds to CD3ε on a T-cell.

16. The polymeric antibody of claim 1, which comprises five immunoglobulin monomers to form a pentamer, wherein each immunoglobulin monomer comprises a μtp domain and a Cμ4 domain.

17. The polymeric antibody of claim 16, wherein each immunoglobulin monomer each further comprise a $C\mu 1$ domain, a $C\mu 2$ domain, and a $C\mu 3$ domain.

18. The polymeric antibody of claim 16, wherein each immunoglobulin monomer comprises one or more heavy chain constant region domains of a non-IgM isotype.

19. The polymeric antibody of claim 18, wherein the non-IgM isotype is IgG.

20. The polymeric antibody of claim 1, which comprises two immunoglobulin monomers to form a dimer, wherein each immunoglobulin monomer comprises an $\alpha tp$ domain and a $C\alpha 3$ domain.

21. The polymeric antibody of claim 20, wherein each immunoglobulin monomer further comprises a $C\alpha 1$ domain and a $C\alpha 2$ domain.

22. The polymeric antibody of claim 20, wherein each immunoglobulin monomer comprises one or more heavy chain constant region domains of a non-IgA isotype.

23. The polymeric antibody of claim 22, wherein the non-IgA isotype is IgG.

24. The polymeric antibody of claim 1, wherein the extraneous binding moiety is an scFv.

25. The polymeric antibody of claim 24, which comprises five immunoglobulin monomers to form a pentamer, wherein each immunoglobulin monomer comprises a $\mu tp$ domain and a $C\mu 4$ domain.

26. The polymeric antibody of claim 25, wherein each immunoglobulin monomer each further comprise a $C\mu 1$ domain, a $C\mu 2$ domain, and a $C\mu 3$ domain.

27. The polymeric antibody of claim 25, wherein each the immunoglobulin monomer comprises one or more heavy chain constant region domains of a non-IgM isotype.

28. The polymeric antibody of claim 27, wherein the non-IgM isotype is IgG.

* * * * *